(12) United States Patent
Mamo et al.

(10) Patent No.: US 8,628,465 B2
(45) Date of Patent: Jan. 14, 2014

(54) SYSTEMS, METHODS AND DEVICES RELATING TO IMPLANTABLE SUPPORTIVE SLINGS

(75) Inventors: George Mamo, Ellicott City, MD (US); Michael F. Weiser, Groton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2676 days.

(21) Appl. No.: 11/152,898

(22) Filed: Jun. 14, 2005

(65) Prior Publication Data

US 2006/0089525 A1   Apr. 27, 2006

Related U.S. Application Data

(60) Provisional application No. 60/579,534, filed on Jun. 14, 2004, provisional application No. 60/649,514, filed on Feb. 3, 2005.

(51) Int. Cl.
*A61F 2/02* (2006.01)

(52) U.S. Cl.
USPC ............................................... 600/37; 600/30

(58) Field of Classification Search
USPC .................... 600/37, 29–31; 606/1, 139, 314, 606/151–158
See application file for complete search history.

(56) References Cited

U.S. PATENT DOCUMENTS

| 3,003,155 | A | 7/1956 | Mielzynski et al. |
| 5,013,316 | A | 5/1991 | Goble et al. |
| 5,112,344 | A | 5/1992 | Petros et al. |
| 5,197,983 | A | 3/1993 | Berman et al. |
| 5,250,054 | A | 10/1993 | Li |
| 5,425,740 | A | 6/1995 | Hutchinson, Jr. |
| 5,439,470 | A | 8/1995 | Li |
| 5,439,474 | A | 8/1995 | Li |
| 5,443,472 | A | 8/1995 | Li |
| 5,449,366 | A | 9/1995 | Li |
| 5,464,189 | A | 11/1995 | Li |
| 5,500,000 | A | 3/1996 | Feagin et al. |
| 5,520,703 | A | 5/1996 | Essig et al. |
| 5,549,636 | A | 8/1996 | Li |
| 5,575,805 | A | 11/1996 | Li |
| 5,611,515 | A | 3/1997 | Benderev et al. |
| 5,643,266 | A | 7/1997 | Li |
| 5,645,589 | A | 7/1997 | Li |
| 5,649,937 | A | 7/1997 | Bito et al. |
| 5,690,649 | A | 11/1997 | Li |
| 5,697,931 | A | 12/1997 | Thompson |

(Continued)

FOREIGN PATENT DOCUMENTS

| AU | 4092199 | 12/1999 |
| CA | 2333121 | 11/1999 |

(Continued)

OTHER PUBLICATIONS

Kovac, Obstetrics & Gynecology, 89(4):624-627, (Apr. 1997).

(Continued)

*Primary Examiner* — John Lacyk
*Assistant Examiner* — Catherine E Burk

(57) ABSTRACT

The invention provides, in various embodiments, aspects of soft tissue anchors, adjustable length/tension slings, interconnects between slings and soft tissue anchors, delivery devices and systems for implanting supportive slings, and methods relating to anchoring, adjusting and implanting supportive slings.

15 Claims, 30 Drawing Sheets

(56) References Cited

U.S. PATENT DOCUMENTS

| | | |
|---|---|---|
| 5,702,215 A | 12/1997 | Li |
| 5,707,395 A | 1/1998 | Li |
| 5,715,942 A | 2/1998 | Li et al. |
| 5,741,300 A | 4/1998 | Li |
| 5,776,147 A | 7/1998 | Dolendo |
| 5,840,011 A | 11/1998 | Landgrebe et al. |
| 5,842,478 A | 12/1998 | Benderev et al. |
| 5,860,425 A | 1/1999 | Benderev et al. |
| 5,899,909 A * | 5/1999 | Claren et al. ............... 606/119 |
| 5,919,232 A | 7/1999 | Chaffringeon et al. |
| 5,922,026 A | 7/1999 | Chin |
| 5,935,138 A | 8/1999 | McJames, II et al. |
| 5,954,057 A | 9/1999 | Li |
| 6,022,373 A | 2/2000 | Li |
| 6,039,686 A | 3/2000 | Kovac |
| 6,039,761 A | 3/2000 | Li et al. |
| 6,042,534 A | 3/2000 | Gellman et al. |
| 6,042,592 A | 3/2000 | Schmitt |
| 6,096,060 A | 8/2000 | Fitts et al. |
| 6,099,538 A | 8/2000 | Moses et al. |
| 6,110,101 A | 8/2000 | Tihon et al. |
| 6,117,161 A | 9/2000 | Li et al. |
| 6,129,762 A | 10/2000 | Li |
| 6,149,669 A | 11/2000 | Li |
| 6,200,330 B1 | 3/2001 | Benderev et al. |
| 6,224,616 B1 | 5/2001 | Kugel |
| 6,273,852 B1 * | 8/2001 | Lehe et al. ............... 600/30 |
| 6,355,053 B1 | 3/2002 | Li |
| 6,406,423 B1 | 6/2002 | Scetbon et al. |
| 6,451,030 B2 | 9/2002 | Li et al. |
| 6,452,450 B1 | 9/2002 | Enriquez |
| 6,478,727 B2 | 11/2002 | Scetbon et al. |
| 6,491,703 B1 | 12/2002 | Ulmsten et al. |
| 6,506,190 B1 | 1/2003 | Walshe |
| 6,575,897 B1 | 6/2003 | Ory et al. |
| 6,582,443 B2 | 6/2003 | Cabak et al. |
| 6,592,515 B2 | 7/2003 | Thierfelder et al. |
| 6,599,323 B2 | 7/2003 | Melican et al. |
| 6,612,977 B2 | 9/2003 | Staskin |
| 6,638,211 B2 | 10/2003 | Suslian et al. |
| 6,641,524 B2 | 11/2003 | Kovac |
| 6,641,525 B2 | 11/2003 | Rocheleau et al. |
| 6,648,921 B2 | 11/2003 | Anderson et al. |
| 6,652,450 B2 | 11/2003 | Neisz et al. |
| 6,666,817 B2 | 12/2003 | Li |
| 6,685,629 B2 | 2/2004 | Therin et al. |
| 6,691,711 B2 | 2/2004 | Raz et al. |
| 6,695,855 B1 | 2/2004 | Gaston et al. |
| 6,786,861 B1 | 9/2004 | Pretorius et al. |
| 6,808,486 B1 | 10/2004 | O'Donnell |
| 6,808,487 B2 | 10/2004 | Migliari et al. |
| 6,852,330 B2 | 2/2005 | Bowman et al. |
| 6,884,212 B2 | 4/2005 | Thierfelder et al. |
| 6,884,428 B2 | 4/2005 | Binette et al. |
| 6,911,003 B2 | 6/2005 | Anderson et al. |
| 6,936,052 B2 * | 8/2005 | Gellman et al. ............ 606/99 |
| 6,960,160 B2 | 11/2005 | Browning |
| 6,971,252 B2 | 12/2005 | Therin et al. |
| 7,025,063 B2 | 4/2006 | Snitkin et al. |
| 7,070,556 B2 | 7/2006 | Anderson et al. |
| 7,083,568 B2 | 8/2006 | Neisz et al. |
| 7,121,997 B2 | 10/2006 | Kammerer et al. |
| 7,131,944 B2 | 11/2006 | Jacquetin et al. |
| 7,361,138 B2 | 4/2008 | Wagner |
| 2002/0078964 A1 | 6/2002 | Kovac et al. |
| 2002/0083820 A1 | 7/2002 | Greenhalgh |
| 2002/0091373 A1 | 7/2002 | Berger |
| 2002/0099258 A1 | 7/2002 | Staskin et al. |
| 2002/0099259 A1 | 7/2002 | Anderson et al. |
| 2002/0133236 A1 | 9/2002 | Rousseau |
| 2002/0138025 A1 | 9/2002 | Gellman et al. |
| 2002/0147382 A1 | 10/2002 | Neisz et al. |
| 2002/0156487 A1 * | 10/2002 | Gellman et al. ............ 606/139 |
| 2002/0161382 A1 * | 10/2002 | Neisz et al. ............... 606/151 |
| 2002/0183762 A1 | 12/2002 | Anderson et al. |
| 2002/0188169 A1 | 12/2002 | Kammerer et al. |
| 2003/0004399 A1 | 1/2003 | Belson |
| 2003/0004580 A1 | 1/2003 | Sump et al. |
| 2003/0004581 A1 | 1/2003 | Rousseau |
| 2003/0065246 A1 | 4/2003 | Inman et al. |
| 2003/0078468 A1 | 4/2003 | Skiba et al. |
| 2003/0078604 A1 | 4/2003 | Walshe |
| 2003/0114865 A1 | 6/2003 | Sater |
| 2003/0114866 A1 | 6/2003 | Ulmsten et al. |
| 2003/0130670 A1 | 7/2003 | Anderson et al. |
| 2003/0171644 A1 | 9/2003 | Anderson et al. |
| 2003/0176762 A1 | 9/2003 | Kammerer |
| 2003/0176875 A1 | 9/2003 | Anderson et al. |
| 2003/0191360 A1 | 10/2003 | Browning |
| 2003/0191480 A1 | 10/2003 | Ulmsten |
| 2003/0199732 A1 | 10/2003 | Suslian et al. |
| 2003/0212305 A1 | 11/2003 | Anderson et al. |
| 2003/0220538 A1 | 11/2003 | Jacquetin |
| 2004/0004600 A1 | 1/2004 | Yoneno et al. |
| 2004/0006353 A1 | 1/2004 | Bosley et al. |
| 2004/0015048 A1 | 1/2004 | Neisz et al. |
| 2004/0015057 A1 | 1/2004 | Rocheleau et al. |
| 2004/0039453 A1 | 2/2004 | Anderson et al. |
| 2004/0039456 A1 | 2/2004 | Davlin et al. |
| 2004/0087970 A1 * | 5/2004 | Chu et al. ............... 606/119 |
| 2004/0097974 A1 | 5/2004 | De Leval |
| 2004/0106847 A1 | 6/2004 | Benderev |
| 2004/0133217 A1 | 7/2004 | Watschke |
| 2004/0144395 A1 | 7/2004 | Evans et al. |
| 2004/0230092 A1 | 11/2004 | Thierfelder et al. |
| 2004/0243166 A1 | 12/2004 | Odermatt et al. |
| 2004/0249240 A1 | 12/2004 | Goldmann et al. |
| 2004/0249397 A1 | 12/2004 | Delorme et al. |
| 2004/0249473 A1 | 12/2004 | Delorme et al. |
| 2004/0267088 A1 | 12/2004 | Kammerer |
| 2005/0004424 A1 | 1/2005 | Raz et al. |
| 2005/0004426 A1 | 1/2005 | Raz et al. |
| 2005/0004427 A1 | 1/2005 | Cervigni |
| 2005/0004576 A1 | 1/2005 | Benderev |
| 2005/0021086 A1 | 1/2005 | DeLeval |
| 2005/0043820 A1 | 2/2005 | Browning |
| 2005/0065395 A1 | 3/2005 | Mellier |
| 2005/0070829 A1 | 3/2005 | Therin et al. |
| 2005/0080317 A1 | 4/2005 | Merade |
| 2005/0107834 A1 | 5/2005 | Freeman et al. |
| 2005/0245787 A1 | 11/2005 | Cox et al. |
| 2005/0250977 A1 | 11/2005 | Montpetit et al. |
| 2005/0267325 A1 | 12/2005 | Bouchier et al. |
| 2005/0278037 A1 | 12/2005 | Delorme et al. |
| 2006/0041185 A1 | 2/2006 | Browning |
| 2006/0058578 A1 | 3/2006 | Browning |
| 2006/0089525 A1 | 4/2006 | Mamo et al. |
| 2006/0205995 A1 | 9/2006 | Browning |

FOREIGN PATENT DOCUMENTS

| | | |
|---|---|---|
| CA | 2427882 | 4/2002 |
| EP | 0632999 | 1/1995 |
| EP | 0774240 | 5/1997 |
| EP | 0677297 | 12/2000 |
| EP | 1079740 | 3/2001 |
| EP | 0643945 | 3/2002 |
| EP | 1324705 | 7/2003 |
| EP | 1333776 | 8/2003 |
| EP | 1342454 | 9/2003 |
| EP | 1345550 | 2/2005 |
| EP | 1191902 | 3/2005 |
| FR | 2811218 | 1/2002 |
| GB | 2382993 | 6/2003 |
| WO | WO 95/18571 | 7/1995 |
| WO | WO-9713465 | 4/1997 |
| WO | WO-9716121 | 5/1997 |
| WO | WO 98/35632 | 8/1998 |
| WO | WO-9835632 | 8/1998 |
| WO | 99/56678 A1 | 11/1999 |
| WO | WO-9959477 | 11/1999 |
| WO | WO 00/40158 | 7/2000 |
| WO | WO-0074594 | 12/2000 |
| WO | WO-0074613 | 12/2000 |

(56) References Cited

FOREIGN PATENT DOCUMENTS

| WO | WO-0106951 | 2/2001 |
|---|---|---|
| WO | WO-0145588 | 6/2001 |
| WO | WO-0178609 | 10/2001 |
| WO | WO-0202031 | 1/2002 |
| WO | WO 02/19945 | 3/2002 |
| WO | WO 02/30293 A1 | 4/2002 |
| WO | WO-0226108 | 4/2002 |
| WO | WO-0228312 | 4/2002 |
| WO | WO-0230293 | 4/2002 |
| WO | WO 0230293 A1 * | 4/2002 |
| WO | WO-0239890 | 5/2002 |
| WO | 02/062237 | 8/2002 |
| WO | WO-02069781 | 9/2002 |
| WO | WO-02071953 | 9/2002 |
| WO | WO-02078548 | 10/2002 |
| WO | WO-02078568 | 10/2002 |
| WO | WO-03/002027 | 1/2003 |
| WO | WO 03/007847 | 1/2003 |
| WO | WO-03002029 | 1/2003 |
| WO | WO-03/028584 | 4/2003 |
| WO | WO-03032867 | 4/2003 |
| WO | WO-03073960 | 9/2003 |
| WO | WO-03075792 | 9/2003 |
| WO | WO03/086205 | 10/2003 |
| WO | WO-03086205 | 10/2003 |
| WO | WO03/096929 | 11/2003 |
| WO | WO-03096928 | 11/2003 |
| WO | WO-03096930 | 11/2003 |
| WO | WO 2004/004600 | 1/2004 |
| WO | WO-2004004600 | 1/2004 |
| WO | 2004/016196 | 2/2004 |
| WO | WO-2004/012626 | 2/2004 |
| WO | WO-2004/016196 | 2/2004 |
| WO | WO-2004012626 | 2/2004 |
| WO | WO-2004019786 | 3/2004 |
| WO | WO2004/045457 | 6/2004 |
| WO | WO-2004045457 | 6/2004 |
| WO | WO-2005007079 | 1/2005 |
| WO | WO2005/094721 | 10/2005 |
| WO | WO-2005/112842 | 12/2005 |
| WO | WO 2005/122721 A2 | 12/2005 |
| WO | WO2005/122954 | 12/2005 |
| WO | WO-2005112842 | 12/2005 |
| WO | WO-2007004613 | 1/2007 |

OTHER PUBLICATIONS

Dargent et al., "Pose d'un ruban sous uretral oblique par vole obturatrice dans le traitement de l'incontinence urinaire feminine," Gynecol Obstet Fertil, 30:576-582, (2002).

Delorme et al., "Transobturator Tape (Uratape®): A New Minimally-Invasive Procedure to Treat Female Urinary Incontinence," European Urology, 45:203-207, (2004).

"New Improvements in the Treatment of Female Stress Incontinence", European Association of Urologists, American Medical Systems (2003).

"The Confident approach to curing incontinence", Monarc™ subfascial hammock, American Medical Systems.

Dargent, D., et al, "Insertion of a suburethral sling through the obturating membrane in the treatment of female urinary incontinence", Gynécol Obstét Fertil, 30:576-82, (2002).

Dargent, D., et al, "Pose d'un ruban sous urétral oblique par voie obturatrice dans le traitement de l'incontinence urinaire féminine", Gynécol Obstét Fertil, 30:576-82, (2002).

de Leval, J., "Novel Surgical Technique for the Treatment of Female Stress Urinary Incontinence: Transobturator Vaginal Tape Inside-Out", European Urology 44:724-730 (2003).

Delorme, E, et al, "Transobturator Tape (Uratape®): A New Minimally-Invasive Procedure to Treat Female Urinary Incontinence", European Urology 45:203-207 (2004).

Delorme, E., "La bandelette trans-obturatrice: un procédé mini-invasif pour traiter l'incontinence urinaire d'effort de la femme", Progrés en Urologie, 11, 1306-1313 (2001).

Delorme, E., "The transobdurator band: a minimmaly invasive procedure for treatment of urinary stress incontinence in women", Progress in Urology, 11, 1306-1313 (2001).

Hermieu, J., et al, "Les bandelettes sous-urétrales synthétiques dans le traitement de l'incontinence urinaire d'effort féminine", Progrés en Urologie, 13, 636-647 (2003).

Ingelman-Sundberg, A., et al, "Surgical Treatment of Female Urinary Stress Incontinence", Contr. Gynec Obstet, vol. 10, pp. 51-69 (1983).

Nickel, R.F., "Transpelvic Sling Urethroplasty with and without Colpususpension for the Treatment of Complicated Urinary Incontinence in Bitches", Third Annual Scientific meeting (ECVS), Riccione, Jun. 23-26, 1994.

Palma, P. C.R. et al, Safyre™: "A Readjustable Minimally Invasive Sling for Female Urinary Stress Incontinence", International Journal of the Brazilian Society of Urology, vol. 29 (4):353-359 (2003).

Siegel, Andrew L., "Vaginal Mesh Extrusion Associated with use of Mentor Transobturator Sling", Elsevier, Inc., Adult Urology, 995-999 (2005).

* cited by examiner

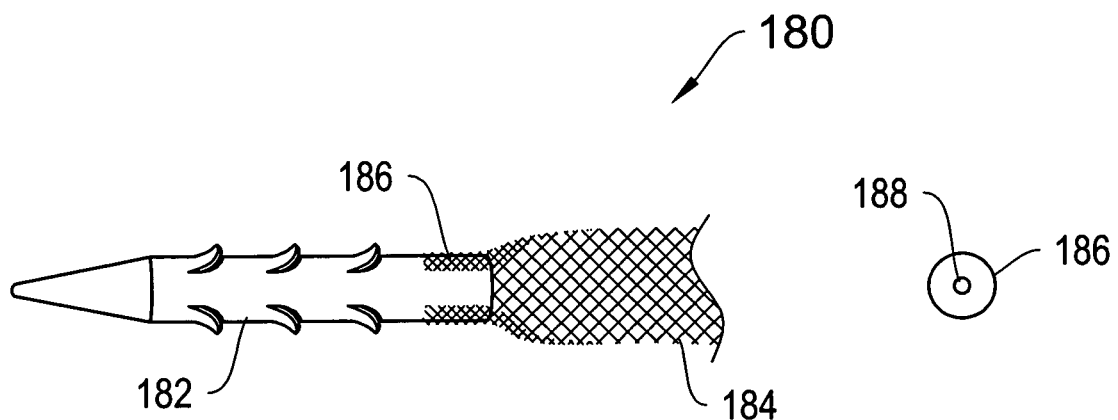
Figure 3B
Figure 3A
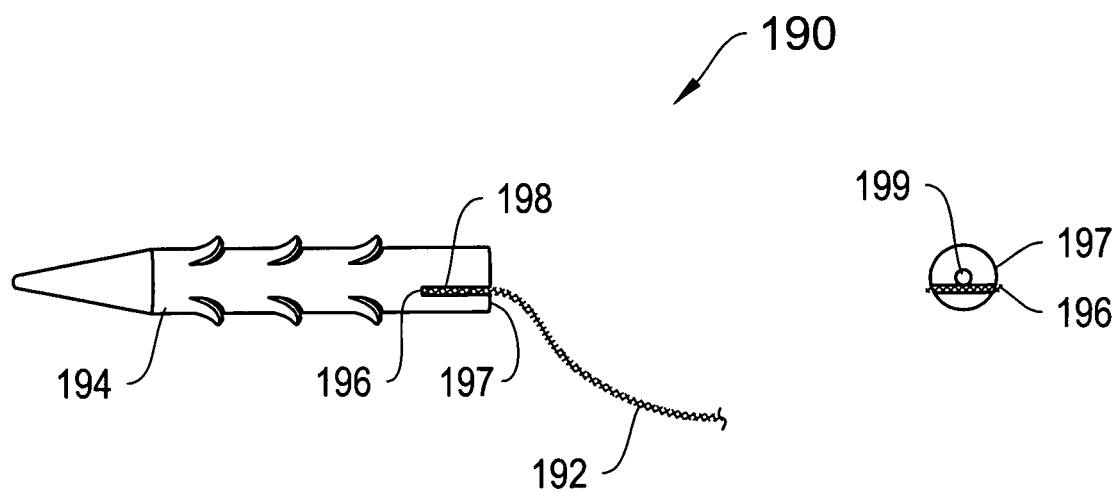
Figure 4B
Figure 4A

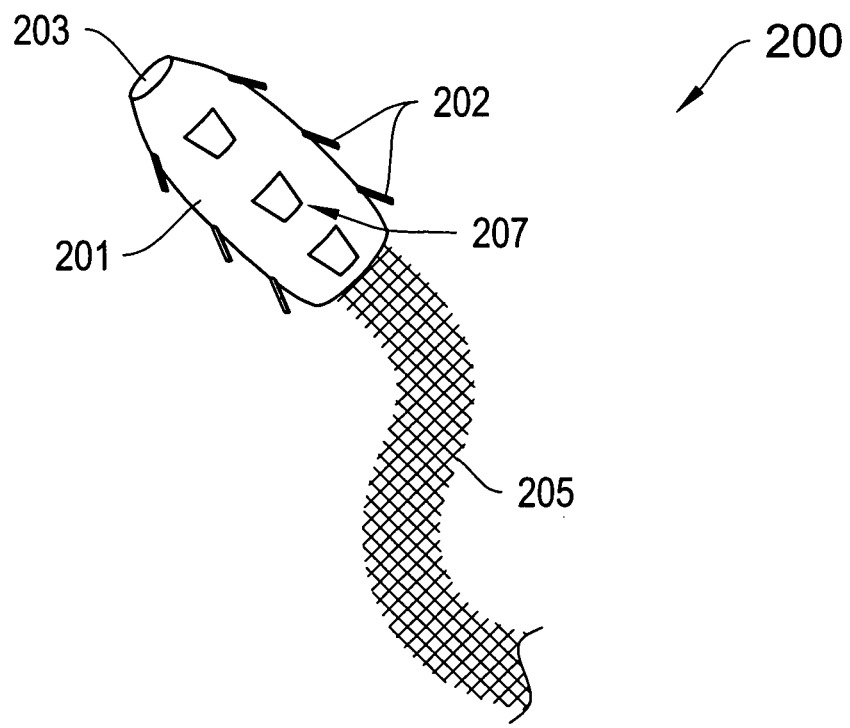
Figure 5A
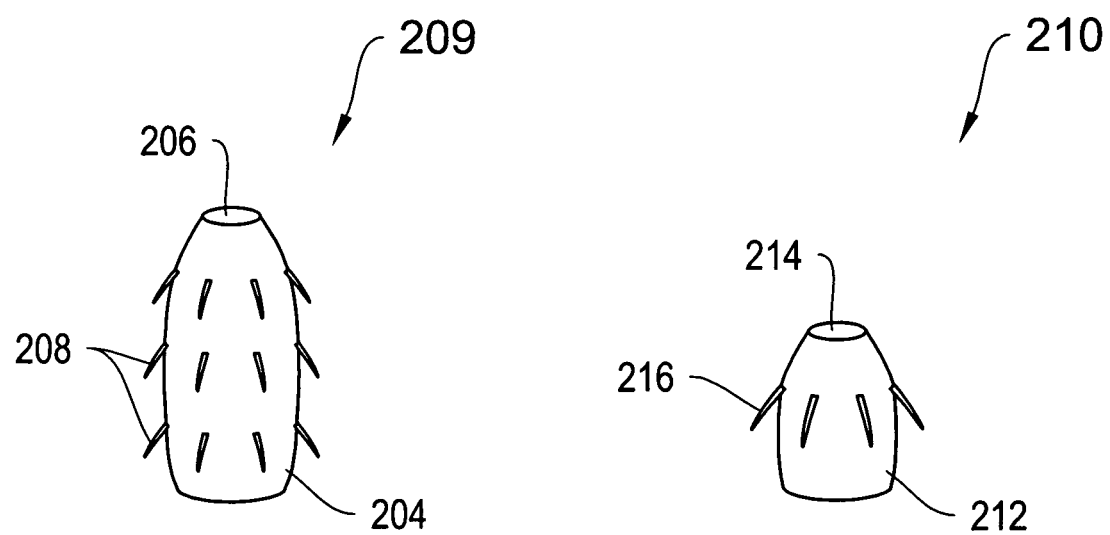
Figure 5B
Figure 5C

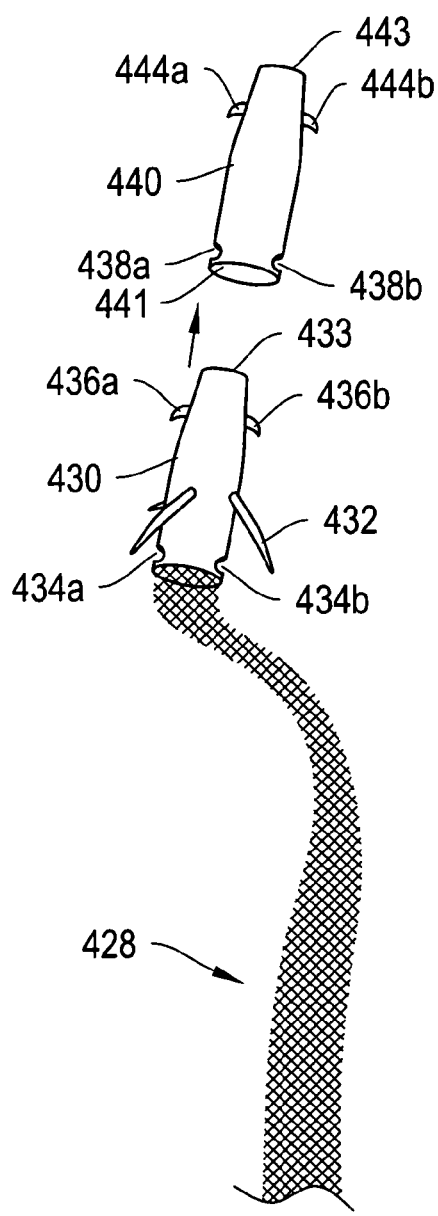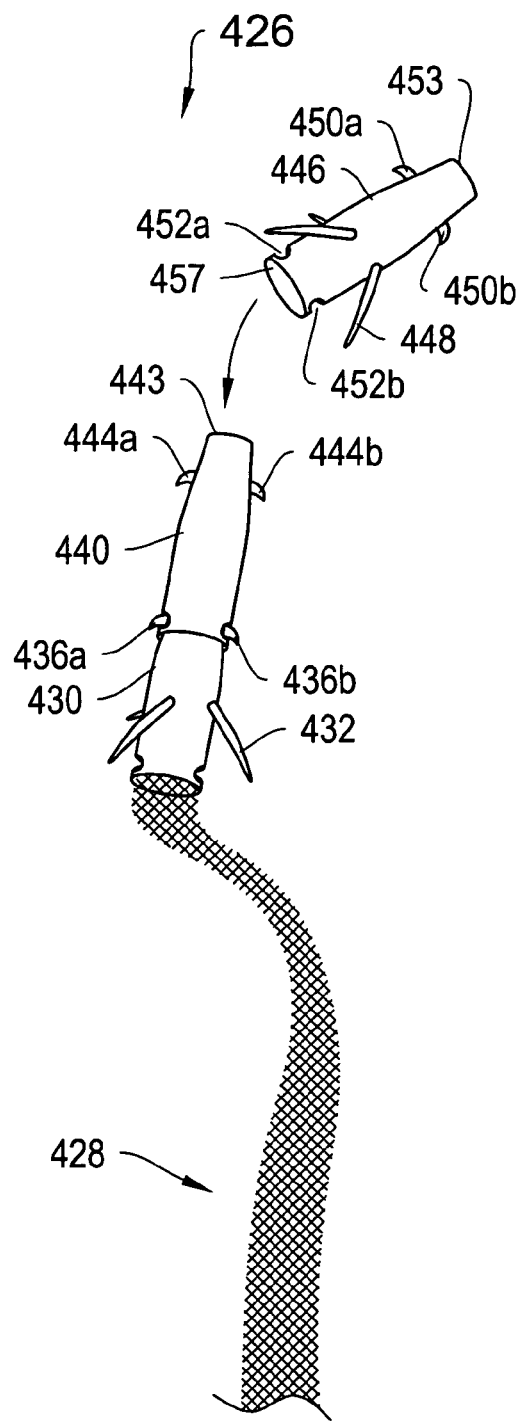
Figure 14A
Figure 14B

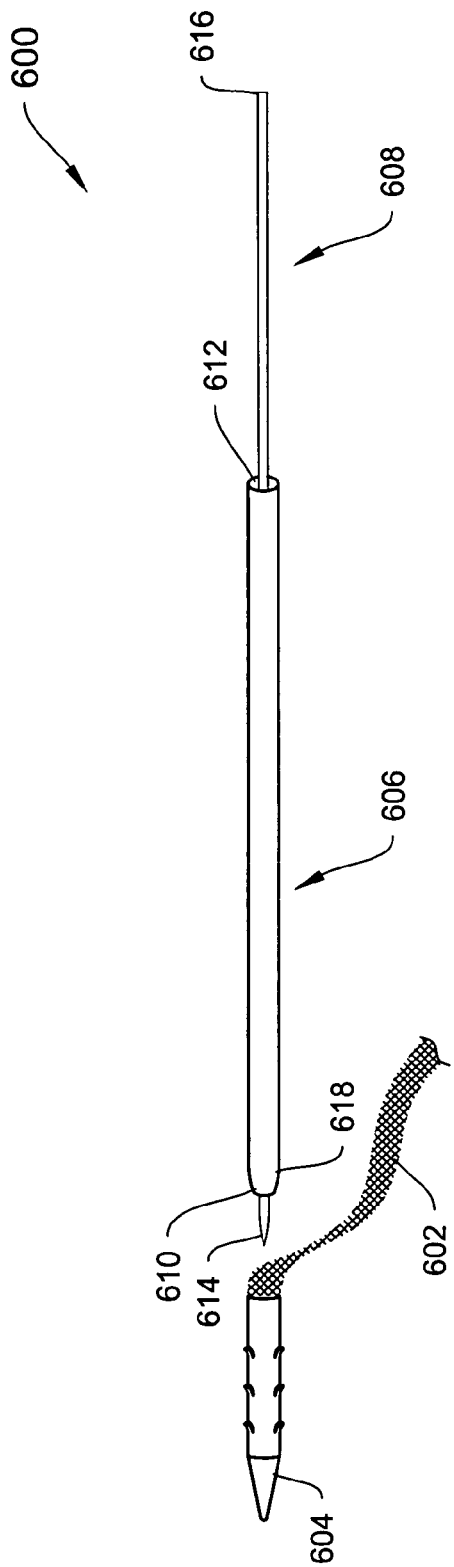
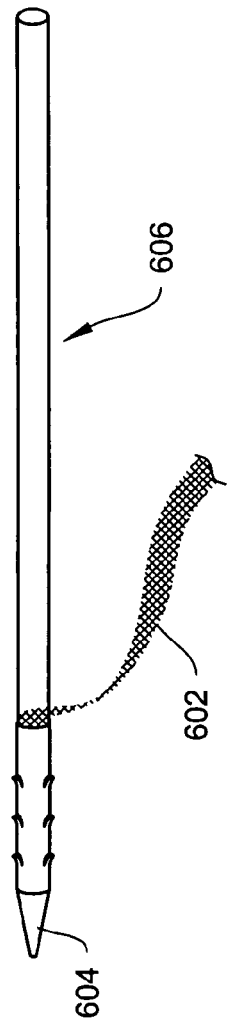
Figure 19A
Figure 19B

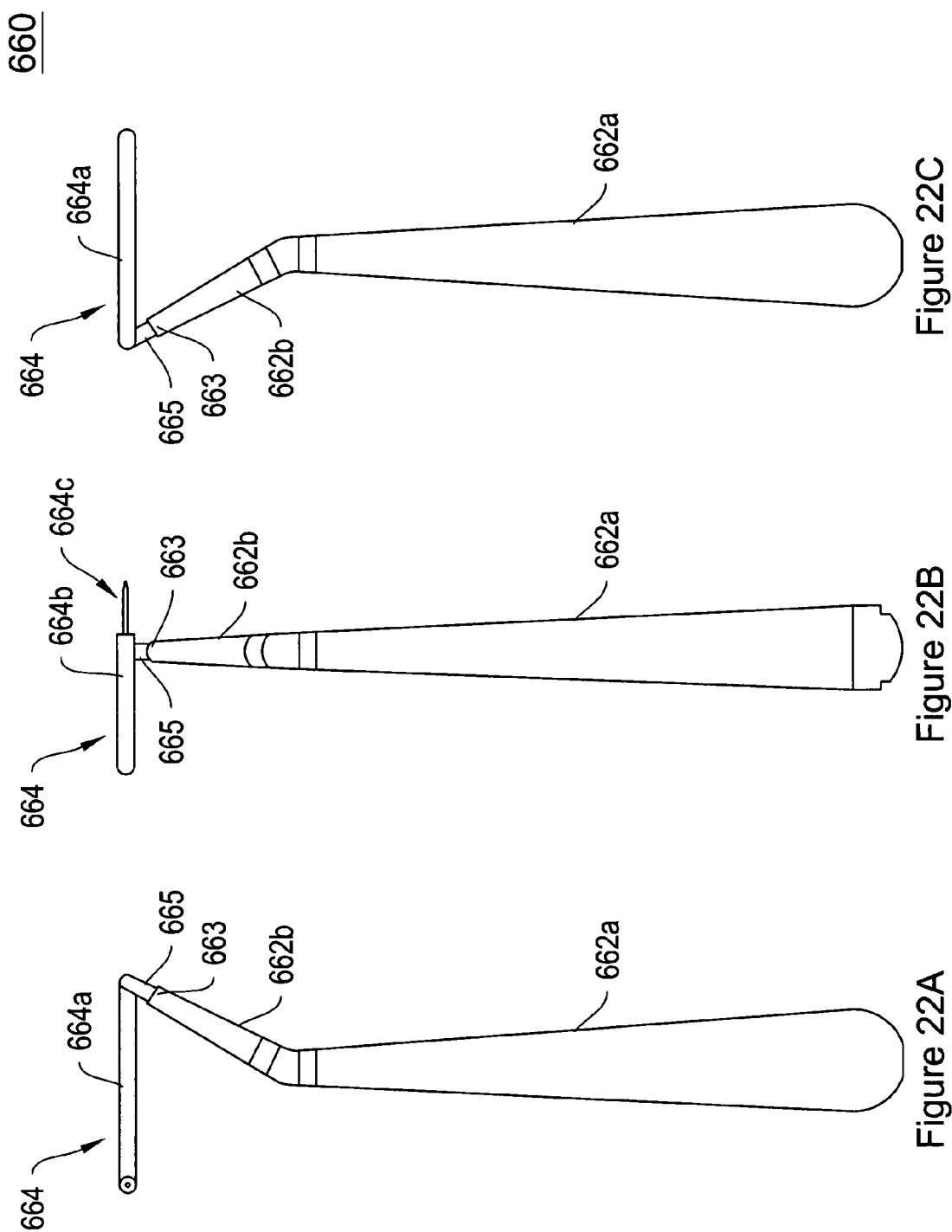

SYSTEMS, METHODS AND DEVICES RELATING TO IMPLANTABLE SUPPORTIVE SLINGS

REFERENCE TO RELATED APPLICATIONS

This application claims priority to and the benefit of U.S. Provisional Patent Application Ser. No. 60/579,534, filed on Jun. 14, 2004 and entitled "Urethral Sling Device for Female Stress Urinary Incontinence," to George Mamo, and U.S. Provisional Patent Application Ser. No. 60/649,514, filed on Feb. 3, 2005 and entitled "Systems and Methods Relating to Anchoring a Medical Implant to Tissue," to George Mamo and Michael Weiser, the entire contents of both of which are incorporated herein by reference.

FIELD OF THE INVENTION

The invention relates generally to implantable supportive slings. More particularly, in various embodiments, the invention is directed to aspects of soft tissue anchors, adjustable length/tension slings, interconnects between slings and soft tissue anchors, delivery devices and systems for implanting supportive slings, and methods relating to anchoring, adjusting and implanting supportive slings.

BACKGROUND OF THE INVENTION

Urinary incontinence occurs in both men and women. Various types of incontinence are caused by different conditions and call for different treatments. For example, stress urinary incontinence (SUI) is known to be caused by at least two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvis floor is distended, weakened or damaged, causing the bladder neck and proximal urethra to rotate and descend in response to increases in intra-abdominal pressure (for example, due to sneezing, coughing, straining, etc.). As a result, the patient's response time becomes insufficient to promote urethral closure and, consequently, the patient suffers from urine leakage and/or flow.

A popular treatment of SUI uses a surgical sling placed under the bladder neck or the mid-urethra to provide a urethral platform. Placement of the sling limits the endopelvis fascia drop. One disadvantage of prior art approaches is that certain mid-urethral sling stabilization procedures typically require incisions in addition to those made in the vaginal wall. By way of example, some procedures require abdominal incisions, while others require groin incisions.

Accordingly, there is a need for improved systems, devices and methods for treating urinary incontinence.

SUMMARY OF THE INVENTION

The invention addresses the deficiencies in the prior art by, in various embodiments, providing improved systems, devices and methods relating to urinary incontinence. More particularly, in some embodiments, the invention provides improved sling assemblies that make it easier for a medical operator to adjust the length and thus, the tension of the sling during implantation. In other embodiments, the invention provides improved soft tissue anchors for affixing supportive slings at a desired anatomical location. In further embodiments, the invention provides dilators sized similarly to tissue anchors, which are used to deliver sling ends to an anatomical location, such as into or through the obturator membrane, but subsequently dissolve, leaving only the sling end embedded in the obturator membrane to hold the sling in place. In additional embodiments, the invention provides improved mechanisms for attaching or otherwise associating soft tissue anchors and/or anchor sized dilators to the ends of sling assemblies to further facilitate sling length/tension adjustment. In further embodiments, the invention provides improved delivery devices, systems and methods for implanting supportive slings and their associated soft tissue anchors and/or anchor sized dilators to desired anatomical sites.

According to one aspect, the invention is directed to an improved implantable supportive sling for treating urinary incontinence. According to one embodiment, the supportive sling of the invention includes a pocket formed at a first end. The pocket is sized and shaped for receiving a distal end of a delivery device shaft. According to a further embodiment, the supportive sling includes a second pocket formed at a second end, also sized and shaped for receiving a distal end of a delivery device shaft. In one implementation, a medical operator may insert a distal end of a shaft into the first end of the sling, and then insert the distal end of the delivery device shaft and sling end into the body of a patient, for example, via an incision in the vaginal wall, to deliver the first end of the sling to a desired anatomical location. The medical operator may deliver the second end of the sling to another anatomical location, for example, on a contralateral side of the patient's body, with the same or a second delivery device using the same or a similar approach, to implant the sling under a location to be supported, such as a mid-urethral location.

The sling may be made from any suitable material, and may include portions having smooth or tanged edges or a combination of smooth and tanged edges. In one configuration, the sling is formed from a mesh material. The sling assemblies are generally short, e.g., from about 5 cm to about 20 cm long. According to one construction, the sling end pockets are formed by folding over the sling material onto itself and sealing the edges. In some configurations, the entire edges of the pockets are sealed. However, in other configurations, only a portion of one or both edges is sealed. According to one feature, portions of the sling ends are left unsealed to allow for tabs to be inserted at the entrance to each end pocket.

According to another aspect, the invention provides a plurality of anchor sized tissue dilators, which may dissolve subsequent to implantation. In other aspects, the invention provides a plurality of soft tissue anchor configurations. In some embodiments, the tissue anchors of the invention have relatively smooth outer surfaces and rely, for example, on orientation and/or features on a sling for anchoring within the tissue. In some such embodiments, these tissue anchors are used primarily as tissue dilators during implantation, and subsequently dissolve, leaving just the sling ends or other tissue ingrowth sites along the sing to hold the sling in place.

In other embodiments, the tissue anchors of the invention include barbs projecting from anchor bodies and are oriented for passing the anchors into tissue and for resisting backing the anchors out of tissue. In some embodiments, the barbs project radially from discrete locations along the anchor bodies. In other embodiments, the barbs are formed as rings projecting radially around the entire circumference of the anchors. In some configurations, one or more of the barbs substantially aligns axially. In other configurations, one or more of the barbs substantially aligns radially along a common circumference. In further configurations, the barbs are arranged so as not to align axially or radially, but instead to be staggered in both directions. In some configurations, the anchors include only a single row of barbs substantially radially aligned along a circumference of the anchor. According to some embodiments, the barbs are formed by building up material onto the outer body of an anchor. In other embodiments, the barbs are molded into the anchor. In further embodiments, the barbs are carved into the outer body of the anchor. In some embodiments, the barbs are formed from pealing back portions of an outer surface of the anchor.

According to some configurations, the barbs are narrow and bristle-like. In some such configurations, the bristles are relatively short (e.g., less than about 2 millimeters in length). However, in other such configurations, the barbs are longer (e.g. between about 2 millimeters and about 5 millimeters in length). According to some embodiments, the barbs have pointed tips. However, in other configurations, the barbs may have rounded tips. According to some embodiments, the barbs are relatively narrow (e.g., less than about 1 millimeter in width/diameter). In other embodiments, the barbs are relatively wide (e.g., between about 1 millimeter and about 2 millimeters in width/diameter).

According to one feature, the soft tissue anchors and/or anchor sized dilators of the invention include an aperture sized and shaped for interfitting over a distal tip of a delivery device shaft. In some configurations, the aperture extends axially from a proximal end of the anchor part way to a distal end of the anchor. In other configurations, the anchor and/or anchor sized dilator includes a through-passage extending axially between the proximal and distal ends of the anchor thus forming a hollow anchor.

According to various embodiments, the anchors and anchor sized dilators of the invention are generally elongated. In some configurations, they are between about 1 centimeter and about 4 centimeters long. According to one configuration, they are between about 2.5 centimeters and about 3.5 centimeters long. According to other embodiments, they have an outside diameter (not including the barbs) of between about 2 millimeters and about 4 millimeters. However, in some embodiments, they have an outside diameter (not including the barbs) of less than about 2 millimeters.

According to other embodiments, the distal tips of the anchors and/or anchor sized dilators may have any suitable configuration. In some embodiments, the distal tips are sharp enough to pierce human tissue. However, in other embodiments, the tips may be rounded. According to some configurations, the distal ends are tapered into a conical shape to provide for tissue dilation during sling implantation.

The anchors and/or anchor sized dilators of the invention may attach to sling ends by any suitable mechanism. In some configurations, the proximal end is, for example, glue-, heat- or shrink tube-bonded to each end of a sling. In other configurations, a proximal portion includes a slot for interfitting with a sling end. Each sling end may be suitably bonded into a proximal slot of a respective anchor or anchor sized dilator. In some configurations, the slot extends distally from the proximal end of the anchor or anchor sized dilator along a cross-sectional diameter of the anchor or anchor sized dilator. According to various constructions, the slings to which the anchors or anchor sized dilators attach are between about 5 centimeters and about 8 centimeters long. In one embodiment, they are about 6 centimeters long. According to a further construction, the total (i.e., anchor/dilator tip to opposite anchor/dilator tip) sling assembly length is between about 8 centimeters and about 14 centimeters. In one embodiment, the total sling assembly length is about 12 centimeters.

According to some aspects, the tissue anchors/dilators of the invention are configured for attaching to a sling end in a sling length/tension adjustable manner. For example, in one embodiment, an anchor/dilator includes a radial aperture in a side wall near its proximal end. A first end of a filament threads through the aperture and a second end of the filament threads through an aperture in a sling end. The aperture in the sling may be, for example, a gap in a mesh or may be separately formed, and optionally reinforced. The length of the filament, and thus the overall length of the sling assembly (i.e., from anchor/dilator distal tip to opposite anchor/dilator distal tip), may be adjusted by pulling on the filament terminal ends and securing them. In some configurations, the filament terminal ends may be secured together, for example, by clipping, tying, gluing or other suitable mechanism. By way of example, in one configuration, the filament ends are tied together in a one-way slip knot, which easily slides to be tightened, but not to be loosened.

According to one embodiment, the filament threads through the aperture or other suitable structure in the anchor/dilator. Then, each end of the filament threads through a separate aperture in the sling end. The further the filament ends are drawn through the sling end apertures, the closer to the sling end the anchor is drawn, once again adjusting the overall length of the sling assembly. As in the prior example, the filament ends may be secured together to hold the sling assembly length constant. The filament ends may be secured, for example, by tying, tying in a one-way slip knot, glued, clipped, or passed through a one-way adjustable holder.

In a further embodiment, the anchor/dilator attaches to a sling end, and the filament ends thread through respective apertures in the sling end. Then, each of the filament ends interweaves with the sling material along at least a partial length of the sling. In one configuration, one filament end interweaves with the sling material along one long edge of the sling, and the other filament end interweaves with the sling material along the other long edge of the sling material. In response to pulling on the terminal ends of the filament, the sling material accordions to reduce its effective length. In some configurations, the interwoven filament is employed only at one end of a sling assembly, with the other end remaining at a fixed location. In some such embodiments, the filament-interwoven, and thus accordionable sling section extends for substantially the entire length of the sling. In other embodiments, the filament is interwoven with half or less of the length of the sling. In further embodiments, the sling assembly employs such interwoven filaments at both ends. In some constructions, the interwoven filaments pass first through an aperture or other suitable structure on an anchor, for example, to attach the anchor/dilator to the sling.

According to alternative embodiments, a tissue anchor/dilator of the invention includes a loop, for example, extending from a proximal end. A sling end may slidably interfit within the loop and the anchor/dilator may be placed at any desired location along the length of the sling. Once placed, the anchor/dilator may be secured in position. The anchor/dilator may be secured in place, for example, with a vascular or any other suitable clip, a suture, or a staple. In the case of the clip or staple, they may be placed on a sling-end side of the anchor to stop the anchor/dilator from sliding in a lengthening direction or sliding off the sling altogether. In some configurations, the loop may include angled spikes or teeth that are oriented to enable the loop, and thus the anchor/dilator, to slide onto the sling, but not allow it to slide in an opposite (e.g., lengthening) direction. In other configurations, a portion of the sling may include one-way bristles or spikes that are oriented to enable the sling end to be inserted into the anchor/dilator loop, but inhibit sliding the anchor/dilator back off the sling in a sling-lengthening direction. In a variation of this configuration, the sling assembly includes an elongated, anchor-like element attached to the sling end. This element includes the directionally oriented spikes, bristles or other projections positioned to slide into the anchor/dilator loop and to impede sliding out of the anchor/dilator loop. The anchor/dilator may be slid along the length of this anchor-like attachment to adjust the overall (anchor/dilator distal tip to anchor/dilator distal tip) length of the sling assembly.

In other configurations, the sling assembly may include a one way buckle, such as that employed on backpacks, for passing the sling end through and adjusting the sling length/tension. In some configurations, the buckle may be, or may be attached to, the anchor/dilator loop. Alternatively, the buckle may be formed into the body of the anchor/dilator. In other configurations, the buckle is located on the sling end, independent from the sling end passing through a loop or other suitable structure on the anchor/dilator. In further configurations, the one way buckle may be placed at any suitable location along the length of the sling.

In another embodiment, an anchor/dilator of the invention includes a hollow portion extending axially from a proximal end at least part way to a distal end of the anchor/dilator, and a bar or other structure extending radially across the hollow portion inside the anchor/dilator. In this embodiment, a sling end may pass into the hollow portion via a proximal opening in the anchor/dilator, then loop around the bar and back out of the proximal end of the anchor/dilator. In some configurations, the bar may include spikes, bristles or other projections for allowing the sling end to pass through the hollow portion in a sling shortening direction, but impeding the sling from passing in an opposite sling-lengthening direction. In other configurations, the sling end may be secured, for example, by way of a clip, staple or suture, outside the anchor/dilator subsequent to the anchor/dilator being placed at a desired location along the sling length. As in all of the described embodiments, excess sling-end material may be trimmed off.

In some embodiments, sling assemblies of the inventions are formed in two sections. In various configurations, one end of each section includes a tissue anchor/dilator and the other end of each section may be affixed together to achieve a desired sling assembly length. In one implementation, one or both of the non-anchor/dilator ends of the two sling assembly sections are cut to length and then attached, for example, by way of suturing, tying, clipping, stapling or heat melting/bonding. In another implementation, the anchor/dilator end of one of the sections is passed through an aperture near the non-anchor/dilator end of the other section. The anchor/dilator is pulled through to a desired length and is then secured in place near the aperture. In some configurations, the sling assembly section being passed through the aperture includes projections for resisting that section from being pulled back out of the aperture in the opposite direction.

According to another aspect, the invention is directed to stackable tissue anchors/dilators. In one embodiment, a first tissue anchor/dilator attaches to a sling end. Then, a second tissue anchor/dilator may slidably interfit over a distal end of the first anchor/dilator to effectively create a longer anchor/dilator with a new distal end. By stacking anchors/dilators in this fashion, the overall (anchor/dilator distal tip to anchor/dilator distal tip) length of the sling assembly may be increased. Previously stacked anchors/dilators may be unstacked to reduce the length of the sling assembly. According to one feature, each anchor/dilator one or more radially extending apertures in its side wall near a proximal end, and one or more corresponding radial projections in its side wall near a distal end. The distal radial projections of the first anchor/dilator snap fit into the proximal radial apertures of the second anchor/dilator to hold the two anchors/dilators together when stacked. Any number of anchors/dilators may be stacked in this fashion.

In other aspects, the invention provides devices and/or systems for delivering a sling assembly to anatomical locations within the body of a patient. Delivery systems include, for example, a sling assembly having at least one tissue anchor/dilator, along with a suitable delivery device. According to one embodiment, a delivery device of the invention includes a handle and a shaft extending distally from a distal end of the handle. A distal end of the shaft may, for example, be sharp enough for piercing tissue, conical in shape for tunneling, or rounded blunt. The shaft may have one or more substantially straight sections and/or one or more curved sections. The shaft may be formed substantially in a single plane, substantially in two planes, or in more than two planes. In one configuration, the delivery device is sized and shaped for delivering sling ends (and tissue anchors/dilators) transvaginally to a suprapubic location (e.g. on the posterior/bladder side of the pubic bone). In other configurations, the delivery device is sized and shaped for delivering the sling ends (and tissue anchors/dilators) transvaginally to a prepubic location (e.g. a location between the pubic bone and the abdominal wall on the anterior side of the pubic bone). This approach has the advantage that there is considerably less risk of inadvertently puncturing the bladder during placement. In further configurations, the delivery device is sized and shaped for delivering the sling ends (and tissue anchors/dilators) transvaginally near, into or through the obturator membrane. In a variation of this configuration, the delivery devices may be sized and shaped for initiating this procedure by inserting a distal end of the delivery device into the patient's body via a vaginal wall incision, or alternatively, via an inner thigh incision.

According to one embodiment, a delivery device of the invention includes a narrowed distal end configured for interfitting with an aperture, a hollow through passage or other suitable feature on a tissue anchor/dilator. Optionally, a shoulder is formed near the distal end of the shaft. When inserted into the anchor/dilator, the shoulder of the delivery device shaft abuts the proximal end of the anchor/dilator. In various configurations, the narrowed distal portion is between about 2 centimeters and about 4 centimeters long. In other configurations it is between about 1 centimeter and about 3 centimeters long. In further configurations, the narrowed distal portion has an outside diameter of between about 0.03 inch and about 0.05 inch. In one embodiment, it has an outside diameter of about 0.04 inches. According to other configurations, the portion of the shaft forming the shoulder has an outside diameter of between about 0.07 inch and about 0.1 inch. In one implementation the outside diameter of this portion of the shaft is about 0.09 inch. According to one configuration, the total shaft length is between about 7 centimeters and about 20 centimeters. In other configurations, the total length of the shaft is between about 8 centimeters and about 12 centimeters.

According to a further embodiment, the delivery device includes an inner shaft and an outer cannula. In one configuration, a distal end of the outer cannula forms a radially extending shoulder around the inner shaft. Additionally, the narrow inner shaft extends distally from the outer cannula (similar to the above described narrowed distal shaft portion) with the outer cannula in a retracted position. According to some embodiments, the delivery device includes a pusher near a distal end of the handle for sliding the outer cannula axially over the inner shaft. In operation, with the pusher retracted, an anchor/dilator is interfitted over the narrowed distal portion of the shaft. Subsequent to anchor/dilator placement, the medical operator slides the pusher distally to push the anchor/dilator off of the narrowed distal portion, and withdraws the delivery device from the patient.

In an alternative embodiment, outer cannula remains fixed and the inner shaft is slidable. More particularly, the delivery device of the invention includes a slidable shaft actuator located on the handle, for enabling an operator to alternatingly extend and retract the distal portion of the shaft from the distal end of the cannula. In operation of this embodiment, an operator extends the distal portion of the shaft to insert it into the tissue anchor/dilator. Subsequent to anchor/dilator placement, the operator retracts the distal portion of the shaft to disengage it from the anchor/dilator, and withdraws the delivery device from the patient.

According to another embodiment, a delivery device of the invention includes a dilator, a pusher and a guide member. In operation a dilator is inserted through an incision in the vaginal wall until its distal tip reaches a location at or near to where an anchor/dilator is to be implanted. The guide member, optionally a guide wire, is inserted axially through the dilator until it extends out of the distal tip of the dilator. The dilator is then slid proximally along the guide wire to remove the dilator from the patient's body. A hollow anchor/dilator of a sling assembly is then slid over a proximal end of the guide wire and slid distally along the guide wire. A pusher is then slid over the proximal end of the guide wire and also slid distally along the guide wire to advance the tissue anchor/dilator along the wire until it reaches a desired location within the body of the patient. The pusher and the guide wire are then removed to leave the tissue anchor/dilator in place.

In another embodiment, a delivery device of the invention includes a hollow insertion shaft and a push wire. In this embodiment, a tissue anchor/dilator of a sling assembly interfits over a distal end of the insertion shaft. The distal end of the shaft with the anchor/dilator so interfitted is inserted into the body of the patient via a vaginal incision. The shaft is advanced distally until the anchor/dilator is located at the desired site of implantation. The push wire is then inserted into a proximal end of the shaft and advanced distally until a distal end of the push wire abuts the tissue anchor/dilator. The push wire is then further advanced distally to push the anchor/dilator off of the insertion shaft to implant the anchor/dilator at the desired location. The insertion shaft and the push wire are then removed from the patient.

As mentioned above, according to some embodiments, the methods of the invention deliver a tissue anchor/dilator of a sling assembly to the obturator foramen. In one approach, the anchor/dilator is delivered to a location in front of the obturator membrane. In another approach, the anchor/dilator is delivered into the obturator membrane. The anchor/dilator may also be fixed to the obturator membrane. In a further approach, the anchor/dilator is delivered through the obturator membrane. In some practices, the anchor/dilator is delivered through the obturator membrane to about 2.5 centimeters into the obturator foramen. In other practices, the anchor/dilator is delivered through the obturator membrane about 1 centimeter to about 2.5 centimeters into the obturator formen.

These and other features, embodiments and aspects of the invention will be further understood with reference to the description of the illustrative embodiments.

BRIEF DESCRIPTION OF THE DRAWINGS

Illustrative embodiments of the invention are described below with reference to the appended drawings, in which like parts have like reference designations and in which the various depicted parts may not be drawn to scale. The depicted embodiments are to be understood as illustrative of the invention and not as limiting in any way.

FIGS. 3A-3B depict an approach for affixing a sling end to a soft tissue anchor/dilator according to an alternative illustrative embodiment of the invention.

FIGS. 4A-4B depict an approach for affixing a sling end to a soft tissue anchor/dilator according to another alternative illustrative embodiment of the invention.

FIGS. 5A-5G depict various hollow soft tissue anchors/dilators according to illustrative embodiments of the invention.

FIGS. 14A-14B depict an arrangement of interlocking stackable soft tissue anchors/dilators for providing adjustable sling assembly length/tension according to another embodiment of the invention.

FIGS. 19A-19B show a delivery system for implanting a sling assembly including a soft tissue anchor/dilator to an anatomical site according to another illustrative embodiment of the invention.

FIGS. 22A-22C show various views of a delivery device having a halo shaft for delivering a sling assembly, for example, transobturally according to another illustrative embodiment of the invention.

ILLUSTRATIVE DESCRIPTION

As described above in summary, the invention addresses deficiencies in the prior art by, in various illustrative embodiments, providing improved systems, methods and devices related to implanting supportive slings within the human body. In particular illustrative embodiments, the systems, methods and devices of the invention are particularly sized, shaped and adapted for delivering a sling to periurethral tissue to provide urethral, bladder, and/or bladder neck support for treating urinary incontinence. As described below in further detail, some of the illustrative embodiments are directed to improved sling and sling assemblies. Other illustrative embodiments are directed to improved tissue anchors, such as soft tissue anchors, for anchoring one or both ends of a sling or sling assembly at a desired anatomical location. Further illustrative embodiments, are directed to anchor sized dilators, which in various implementations may be sized and shaped like any of the described anchors, except with substantially smooth outer surfaces. In some of these illustrative embodiments, the dilator/anchor relies on dilator/anchor orientation, rather than barbs for anchoring. In other illustrative embodiments, the anchor/dilator dissolves and is bioabsorbed, leaving only the sling ends or other locations along the sling itself to hold the sling in place. In some illustrative embodiments, the improved anchors/dilators include, for example, improved anchoring structures, improved interfittings with delivery devices, improved features for attaching the anchors to the sling assembly in a length/tension adjustable manner, and the like. Additional illustrative embodiments are directed to improved delivery devices and sling delivery systems. The illustrative delivery systems include, for example, a sling assembly along with a delivery device.

Other illustrative embodiments describe exemplary procedures for implanting a supportive sling employing features of the invention.

Figure 1A:
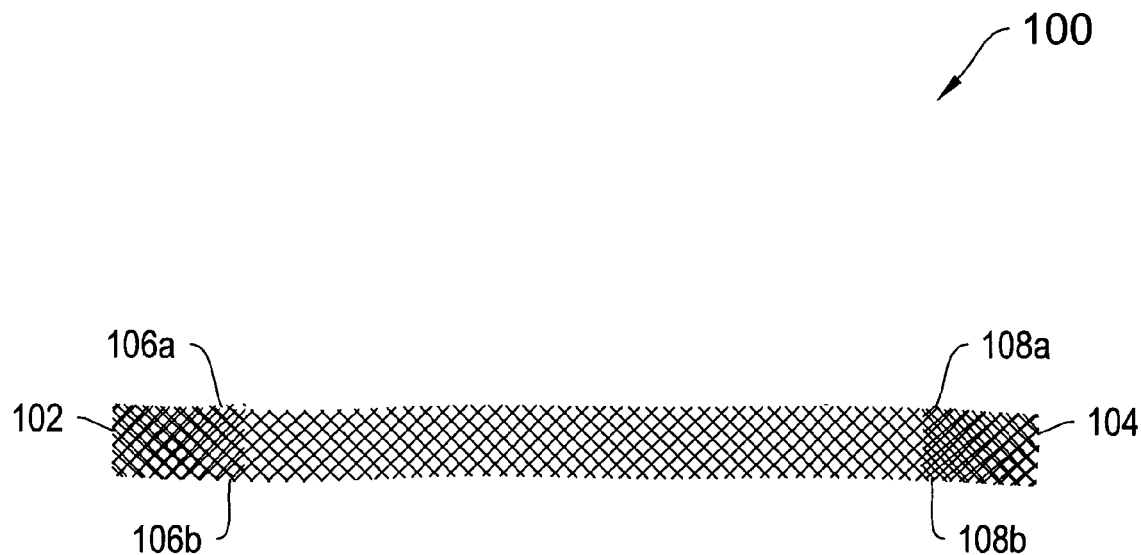
FIGS. 1A-1B depict different views of a mesh sling including end pockets according to an illustrative embodiment of the invention.
Figure 1B:
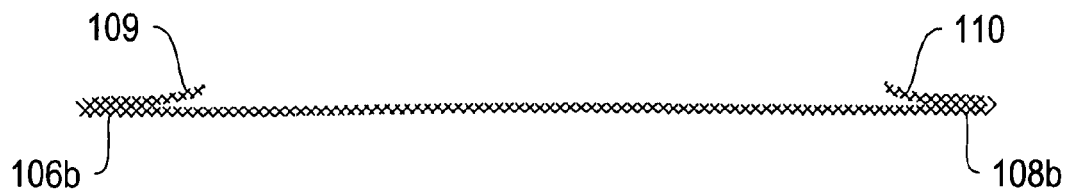

Turning to the depicted illustrative embodiments, FIGS. 1A and 1B depict top and side views, respectively, of a sling 100 including end pockets 102 and 104. The end pockets 102 and 104 are formed by folding a short length of an end of the sling, e.g., about 0.5 inches to about 1.0 inches, over onto itself and closing the edges. For example, the edges 106a and 106b are closed to form the pocket 102 and the edges 108a and 108b are closed to form the pocket 104. The edges may be closed, for example, by way of suturing, gluing or heat sealing. The edge closures may extend for the entire length of the folded over portions, or as most clearly shown in FIG. 1B, a portion 109 and 110 of the respective folder over portions may be left without its edges closed to provide for free tabs at the entrance to the pockets 102 and 104.

In certain illustrative embodiments, the pockets 102 and 104 of the sling 100 may be coated or otherwise treated with a material to stiffen and/or strengthen them. According to the illustrative embodiment, the sling 100 is between about 5 centimeters and about 20 centimeters long. According to a feature of the sling 100, a distal end of a delivery device shaft may be inserted into either pocket 102 or 104 and then inserted through a vaginal incision to deliver a sling end to an anatomical site. With the delivery device removed, either or both of the pockets 102 and 104 may employed as a soft tissue anchor. By way of example, the pocket 102 and/or 104 may be implanted into or through a obturator membrane or other tissue, muscle, ligament or suitable anatomical structure. The folded over sling material then resists the pulling of the end pocket back out of the membrane or other structure to anchor the sling end in place.

The sling 100 may be formed from any suitable materials and configurations. For example, the sling 100 may be formed from an omnidirectional material, a material that has equivalent tensile strength from any direction, such as pericardium or dermis. Alternatively, the material may be an oriented material, a material that has a single direction where the tensile strength of the material is the highest. Oriented materials may include rectus fascia and/or facia lata.

The edge or other regions of the sling 100 can be configured differently depending on their intended placement in the body of the patient. For example, a middle section of the sling 100 is typically located where an anatomical site, such as a midurethral or bladder neck location in the periurethral tissue, needs to be supported. In one illustrative embodiment, a middle section of the sling 100 has smooth or rounded edges, hereinafter also referred to as "non-tanged." According to a further illustrative embodiment, other sections of the sling 100 may include tangs (e.g., sharp projections or frayed edges). The tangs are generally useful for anchoring the sling 100 and encouraging tissue growth into the sling 100. Anchoring the sling 100 in this manner generally obviates the need for additional sutures to hold the sling 100 in place. Anchoring the sling 100 via its tangs is especially useful for anchoring the sling 100 on a tissue and facilitating the removal of the sleeve according to the invention by pulling on the center tab of the sleeve while the sling 100 stays in place, without the need for additional incisions in order to hold the sling 100 external to the body while the sleeve is being removed through pulling.

The tanged and non-tanged edges of the sling 100 may be formed in a plurality of ways. For example, the sling 100 can be cut from a woven sheet, in which case the edges would be initially tanged along the entire length of the sling 100. One or more non-tanged sections may be formed by any process that smoothes, rounds or removes the sharp edges of the tangs. For example, the tangs may be heat-smoothed by burning or melting the tangs. Providing one or more non-tanged sections, which may be in close proximity to a sensitive anatomical site in the patient, can enhance the comfort level of the patient and reduce the potential for the edges of the tangs to erode or irritate the urethra. Alternatively, the sling 100 can be produced from a woven tape having the approximate finished width of the sling 100. The smooth sides of the tape can then be trimmed off to produce the tanged sections.

The sling 100 used with the invention may be fabricated from any suitable material(s), preferably biocompatible materials. In certain illustrative embodiments, the material may include, for example, synthetic mesh or other synthetic material; it may also or alternatively include non-synthetic material, such as cadaver, human or animal tissue; it may also include any combinations thereof. In examples employing synthetic material for the sling 100, it may be derived from any suitable synthetic material. Such material could include, for example, polymeric material such as, for example, as Polytetrafluorethylene (Goretex), polypropylene (Marlex), polyethylene (Mersiline), silastic, or impregnated collagen matrix (Protegen). In certain illustrative embodiments, one or more suitable materials for the sling 100 may include, for example, nylon, polyethylene, polyester, polypropylene, fluoropolymers, copolymers thereof, combinations thereof, or other suitable synthetic material(s). The material may be, for example, a synthetic material that is absorbable by the patient's body. Suitable absorbable synthetic materials can include polyglycolic acid, polylactic acid, and other suitable absorbable synthetic materials. The sling 100 material may be fabricated from one or more yarns, which yarns may be made from one or more materials.

Alternatively, the materials for the sling 100 may employ non-synthetic or natural materials, for example materials from human fascia, cadaveric fascia or skin mammalian tissue(s). Human tissues may be used in certain embodiments and may be derived, for example, from human cadaveric or engineered human tissue. Animal tissues may be derived, for example, from porcine, ovine, bovine, and equine tissue sources. In certain embodiments the materials for the sling 100 may include a combination of non-synthetic (e.g., mammalian tissue(s)) and synthetic material(s).

According to a further illustrative embodiment, any or all of the sling 100 may be configured to be biodegradable/bioabsorbable. According to another feature, at least a portion of the sling 100 is biodegradable and may also dissolve and/or be absorbed into the patient's tissues. For example, in some embodiments, only a section of the sling 100 is biodegradable/bioabsorbable, such as, for example, an intermediate portion. Examples of biodegradable/bioabsorbable materials that may be used for the sling 100 include, without limitation, polylactic acid (PLA), polyglycolic acid (PGA), poly-L-lactic acid (PLLA), human dermis and decellularized animal tissue.

Exemplary biodegradable/bioabsorbable materials, in addition to those listed above, which may be employed for the sling 100 include, but are not limited to, polylactic acid, polyglycolic acid and copolymers and mixtures thereof, such as poly(L-lactide) (PLLA), poly(D,L-lactide) (PLA), polyglycolic acid [polyglycolide (PGA)], poly(L-lactide-co-D,L-lactide) (PLLA/PLA), poly(L-lactide-co-glycolide) (PLLA/PGA), poly(D,L-lactide-co-glycolide) (PLA/PGA), poly (glycolide-co-trimethylene carbonate) (PGA/PTMC), poly (D,L-lactide-co-caprolactone) (PLA/PCL), and poly (glycolide-co-caprolactone) (PGA/PCL); polyethylene oxide (PEO); polydioxanone (PDS); polypropylene fumarate; polydepsipeptides, poly(ethyl glutamate-co-glutamic acid), poly(tert-butyloxy-carbonylmethyl glutamate); polycaprolactone (PCL), poly(hydroxy butyrate), polycaprolactone co-butylacrylate, polyhydroxybutyrate (PHBT) and copolymers of polyhydroxybutyrate; polyphosphazenes, poly(phosphate ester); maleic anhydride copolymers, polyiminocarbonates, poly[(97.5% dimethyl-trimethylene carbonate)-co-(2.5% trimethylene carbonate)], cyanoacrylate, hydroxypropylmethylcellulose; polysaccharides, such as hyaluronic acid, chitosan and regenerate cellulose; poly(amino acid) and proteins, such as gelatin and collagen; and mixtures and copolymers thereof.

According to a further illustrative embodiment, the sling 100 may incorporate or be coated with one or more agents to provide a therapeutic effect, for example, to reduce discomfort, to reduce the chance of infection and/or to promote tissue growth. The sling 100 may be treated or coated with any suitable material. For example, in some illustrative embodiments, suitable treatment materials may include bioabsorbable/dissolvable materials which may include, but are not limited to, alginates, sugar based formulations, starches, gelatins, cellulose, polyvinyl alcohol, polyglycolic acid (PGA), polylactic acid (PLA), polydioxinone (PDO), and/or other synthetic or natural polymers including combinations thereof. The treatment materials are preferably biocompatible, and the biocompatible protective treatment may cover any portion or all of the sling 100. In one particular configuration, the protective treatment encapsulates or substantially encapsulates at least portion of the sling 100. According to one feature, the protective treatment is formed from lubricious material and reduces the friction between the sling 100 and the patient's periurethral tissues. In this way, the protective treatment can provide a relatively smooth tissue contact surface to otherwise tanged or ragged sling edges to reduce the likelihood of the sling 100 irritating the patient's tissues during implantation.

The protective treatment may be applied to the sling 100 by any suitable approach, for example, by way of spraying, brushing or dipping the portion of the sling 100 to be treated. According to another illustrative embodiment, the protective treatment is formed as a sheet of material that can be affixed to the portion of the sling 100 to be treated. According to another feature, the protective treatment may be configured to dissolve within a particular time range. The protective treatment may be configured, for example, to substantially absorb into the patient's tissues within about 30, 15, 10 or 5 minutes from the time the sling 100 is implanted. Alternatively, the protective treatment may be configured to substantially absorb into the patient's tissues over a time span of hours, days, weeks, or months.

According to another illustrative feature, the sling 100 may also include an agent for release into the patient's tissues. One illustrative agent promotes, when applied to the patient's tissues in a pharmaceutically acceptable amount, well-organized collagenous tissue growth, such as scar tissue growth, preferably, in large quantities. According to one feature, the agent may or may not block or delay the dissolvability of the protective treatment. This may be controlled by selecting differing methods for loading the agent onto the sling 100. The tissue growth factor may include natural and/or recombinant proteins for stimulating a tissue response so that collagenous tissue such as scar tissue growth is enhanced. Exemplary growth factors that may be used include, but are not limited to, platelet-derived growth factor (PDGF), fibroblast growth factor (FGF), transforming growth factor-beta (TGF-beta), vascular endothelium growth factor (VEGF), activin/

TGF and sex steroid, bone marrow growth factor, growth hormone, insulin-like growth factor 1, and combinations thereof. The agent may also include a hormone, including but not limited to estrogen, steroid hormones, and other hormones to promote growth of appropriate collagenous tissue such as scar tissue. The agent may also include stem cells or other suitable cells derived from the host patient. These cells may be fibroblast, myoblast, or other progenitor cells to mature into appropriate tissues.

In various illustrative embodiments, the agent may include one or more therapeutic agents. The therapeutic agents may be, for example, anti-inflammatory agents, including steroidal and non-steroidal anti-inflammatory agents, analgesic agents, including narcotic and non-narcotic analgesics, local anesthetic agents, antispasmodic agents, growth factors, gene-based therapeutic agents, and combinations thereof.

Exemplary steroidal anti-inflammatory therapeutic agents (glucocorticoids) include, but are not limited to, 21-acetoxyprefnenolone, alclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methyolprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Exemplary non-steroidal anti-inflammatory therapeutic agents include, but are not limited to, aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid; carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as $\epsilon$-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Exemplary narcotic analgesic therapeutic agents include, but are not limited to, alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof.

Exemplary non-narcotic analgesic agents that may be combined with the sling 100 include, but are not limited to, aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide o-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Exemplary local anesthetic therapeutic agents include, but are not limited to, ambucaine, amolanone, amylocaine hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Exemplary antispasmodic therapeutic agents include, but are not limited to, alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n-trimethyl-3, 3-diphenyl-propylamine, tropenzile, trospium chloride, xenytropium bromide, and pharmaceutically acceptable salts thereof.

The agent may be associated with the sling 100 in a variety of manners. For example, the agent may be chemically or physically attached to the surface of the sling 100. In one illustrative embodiment, the surface of the sling 100 and the agent, for example, in solution, have complementary ionic charges. As such, when placed on the sling 100, the agent ionically bonds to its surface. In another illustrative embodiment, before application of the agent, the protective treatment is applied to the sling 100. According to another illustrative embodiment, the protective treatment and the agent are mixed to form a single treatment and then applied to the sling 100 in a one step process. According to the invention, any suitable process may be employed for associating the agent with the sling 100, such that the agent can leach to tissue in the region of the implanted sling 100 and/or the protective treatment can dissolve and/or leach into the tissue in the region of the implanted sling 100.

FIGS. 2A-2E show tissue anchors/dilators according to various illustrative embodiments of the invention. It should be noted that any of the anchoring structures described herein with radial projections for anchoring, may also be implemented without such projections or with such projections, rounded, smoothed or otherwise reduced in side, so as to accentuate tissue dilation as opposed to tissue anchoring. Thus, although features of the invention may be described below with regard tissue anchors, all such features may be employed with similarly sized tissue dilators. As also mentioned below, any of the illustrative anchors/dilators may be configured to be bioabsorbable/biodegradable, so that they dissolve subsequent to implantation into a patient, leaving only the sling ends, or other portions of the sling to hold itself in place. Similarly, as also mentioned below, portions of the sling may also be bioabsorbable/biodegradable so it dissolves subsequent to implantation, leaving scar tissue in its place as a naturally formed sling/platform.

According to various configurations, the below described anchors/dilators are generally elongated. In some configurations, the anchors/dilators are between about 1 centimeter and about 4 centimeters long. According to other configurations, the illustrative anchors/dilators are between about 2.5 centimeters and about 3.5 centimeters long. According to additional configurations, the illustrative anchors/dilators have an outside diameter (not including the barbs) of between about 2 millimeters and about 4 millimeters. However, in some configurations, the illustrative anchors/dilators of the invention have an outside diameter (not including the barbs) of less than about 2 millimeters.

As described below, in some of the illustrative embodiments, the tissue anchors/dilators of the invention have relatively smooth outer surfaces, and rely on orientation and/or features on an attached sling for anchoring within the patient's tissues. However, in other illustrative embodiments, the anchors of the invention include radial projections for resisting removal from a patient's tissue once implanted. The radial projections may have any of a plurality of configurations. According to some configurations, the projections form barbs (also referred to as tines) that are narrow and bristle-like. In some of these configurations, the bristles are relatively short (e.g., less than about 2 millimeters in length). However, in other such configurations, the barbs are longer (e.g. between about 2 millimeters and about 5 millimeters in length). According to some embodiments, the radial projections have pointed tips. However, in other configurations, the projections may have rounded tips. According to some illustrative embodiments, the projections are relatively narrow (e.g., less than about 1 millimeter in width/diameter). In other illustrative embodiments, the projections are relatively wide (e.g., between about 1 millimeter and about 2 millimeters in width/diameter). In some instances, the radial projections are wide enough to extend all the way around a circumference of the anchor.

Figure 2A:
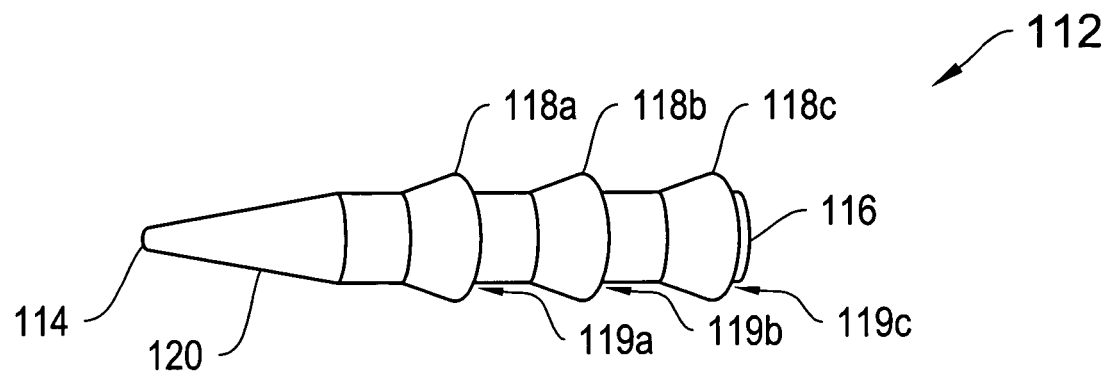
FIGS. 2A-2E each depict various soft tissue anchors/dilators according to illustrative embodiments of the invention.

Turning now to the drawings, FIG. 2A depicts a tissue anchor 112 having distal 114 and proximal 116 ends. The anchor 112 includes an aperture at the proximal end 116 for receiving a distal end of a delivery device shaft. The aperture may or may not extend through-lumen all the way through to the distal end 114. The anchor 112 includes a plurality of radial projections 118a-118c. In this particular embodiment, the projections 118a-118c are formed as a build up of a polymer material onto an original anchor body. Each of the projections 118a-118c circumscribes the circumference of the anchor 112, and is curved/oriented to facilitate insertion into tissue, but each also includes a respective proximally facing surface 119a-119c (oriented substantially normal to the long axis of the anchor 112) for resisting removal from the tissue. The distal end 114 may have any suitable shape, including being sharpened to pierce tissue or being rounded blunt. As shown in FIG. 2A, the anchor 112 includes a conical shaped distal end 120 for providing tissue dilation during insertion.

As is the case with any of the anchors/dilators described herein, the anchor 112 may be inserted into any suitable soft tissue in a patient, including ligaments, muscles, cartilage, fibro-fatty tissue, organs, and soft portions of bones or bone coatings. As is also the case with any of the tissue anchors/ dilators of the invention, the anchor 112 may be formed from any suitable biocompatible material, such as any suitable polymer material. As described below in more detail, the anchors/dilators may also be coated or otherwise treated with any suitable material, and may be partially or entirely biodegradable/bioabsorbable.

Figure 2B:
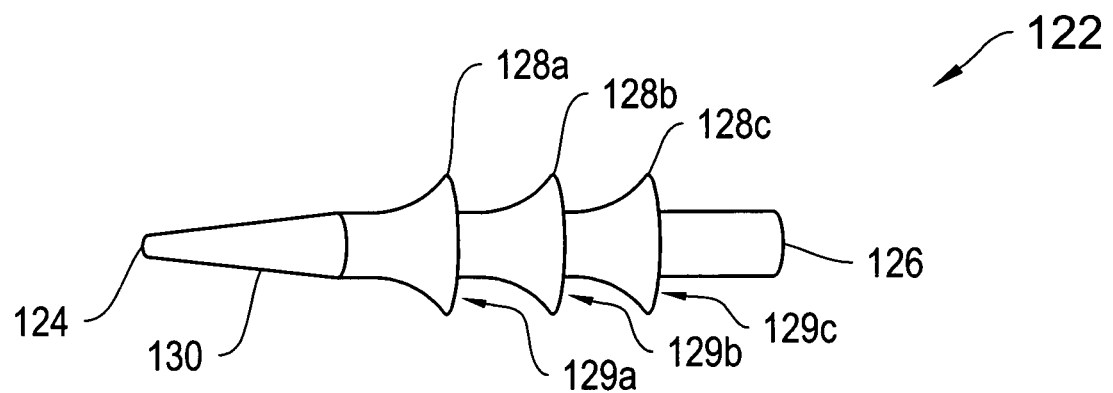

FIG. 2B shows an alternative tissue anchor 122. As in the case of the anchor 112, the anchor 122 includes distal 124 and proximal 126 ends, and an aperture at the proximal end 126 for receiving a distal end of a delivery device shaft. As is the case with all of the anchors of FIGS. 2A-2E, the aperture may or may not extend as a through-lumen all the way through to the distal end 124. The anchor 122 includes a plurality of radial projections 128a-128c, which are similar in configuration to the radial projections 118a-118c, in that they are sloped/oriented to facilitate insertion into tissue and include proximally facing surfaces 129a-129c for resisting removal from the tissue. In contrast to the radial projections 118a-118c, the radial projections 128a-128c are molded into the body of the anchor 122. Each of the projections 128a-128c also circumscribes the circumference of the anchor 122. The distal end 126 has a similar conical shape to that of the anchor 112.

Figure 2C:
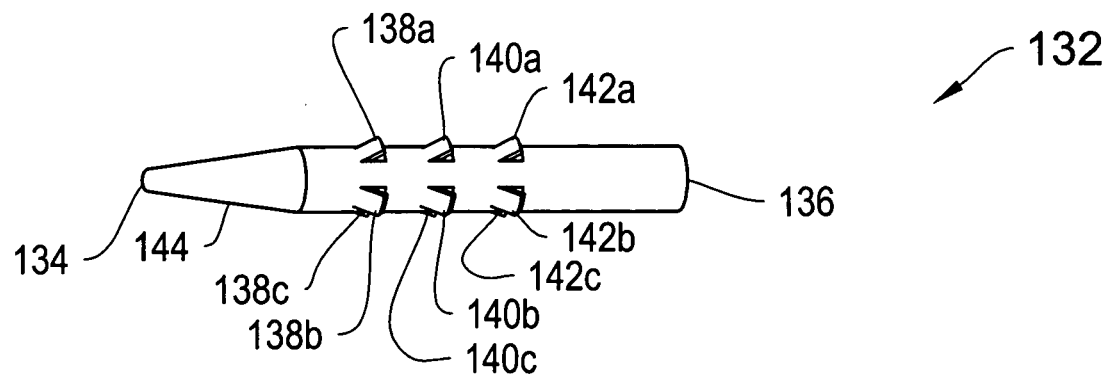

FIG. 2C shows another illustrative tissue anchor 132 having all of the described properties of the anchors 112 and 122, but having an alternative barb configuration. More specifically, the anchor 132 includes distal 134 and proximal 136 ends configured similarly to those of the anchors 112 and 122. The anchor 123 also includes a conical distal tip 144. However, the anchor 132 includes three radially aligned rows of discrete radially projecting barbs. Specifically, the anchor 136 includes a first row of radial projecting barbs 138a-138c, a second row of radially projecting barbs 140a-140c, and a third row of radially projecting barbs 142a-142c. According to one feature of this illustrative embodiment, the barbs also substantially align axially. For example, the barbs 138a, 140a and 142a all substantially align axially. Similarly, the barbs 138b, 140b, and 142b also substantially align. The same is the case for the barbs 138c, 140c and 142c. The barbs of this embodiment have squared edges and relatively flat surfaces. Their tips are formed as blunt flat surfaces. As in the prior examples, they are sloped to facilitate insertion into tissue and to resist removal from the tissue.

Figure 2D:
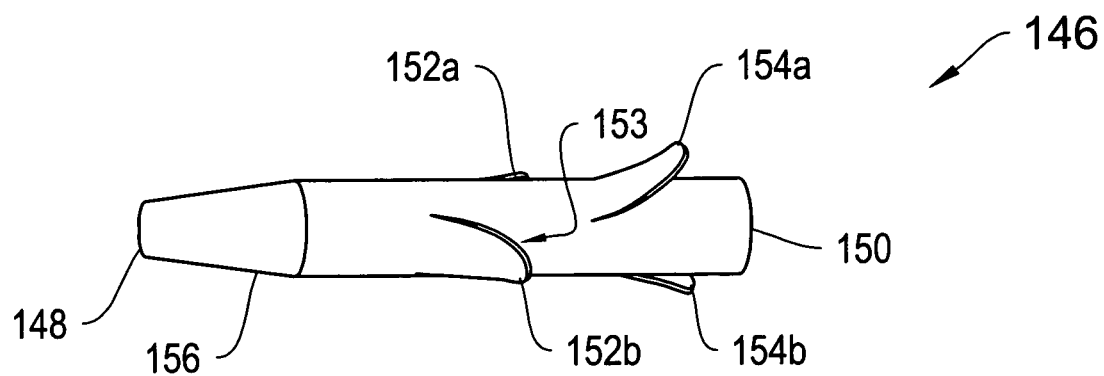

FIG. 2D shows a further illustrative tissue anchor 146. As in the prior examples, the anchor 46 includes distal 148 and proximal 150 ends and a conical tip 156. However in this illustrative embodiment, the anchor 146 includes two axial rows of barbs as opposed to three, and each row includes two barbs; 152a and 152b in the first row and 154a and 154b in the second row. Another difference in this embodiment is that the barbs 152a and 154a do not align axially. Instead they are rotationally offset from each other. The same is true for the barbs 152b and 154b. According to the particular illustrative embodiment, the first and second rows of barbs are offset from each other by about 90°, but other rotational offsets may be employed. Another feature of the anchor 146 is that the barbs are cut away and peeled back from the body of the anchor 146. For example, the barb 152b is cut away from the anchor body at location 153.

Figure 2E:
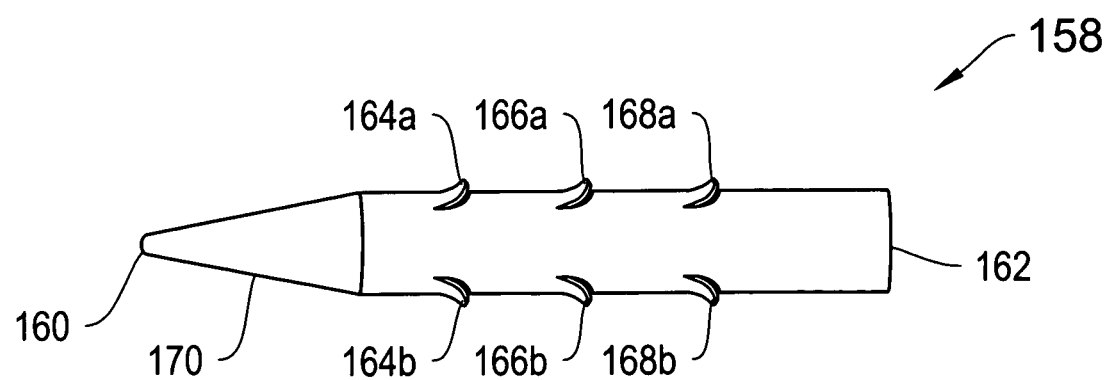

FIG. 2E shows another illustrative tissue anchor 158. The anchor 158 is similar to the anchor 146 in that it includes distal 160 and proximal 162 ends and a conical tip 170. It also includes barbs 164a, 164b, 166a, 166b, 168a, and 168b, which are cut away and peeled back from the body of the anchor 146. However, in the configuration of FIG. 2E, the peeled back barbs align both in radially and axially extending rows. For example, barbs 164a and 164b align radially along a circumference of the anchor 158, and the barbs 164a, 166a, and 168a all align axially.

In certain illustrative embodiments, any materials described above for use with the sling 100 may also be used for any of the anchors/dilators. For example, any or all of the anchors/dilators may be configured from synthetic materials, non-synthetic materials, or both. The anchors/dilators may also be configured to be bioabsorbable/biodegradable, either in whole or in part, and such configurations may employ any of the materials referenced above in reference to materials used for the sling 100. Moreover, the anchors/dilaors may be prepared to include a protective coating or treatment, as described above in reference to the sling 100, and may also be configured to contain an agent for release into the patient's tissues, again as described above in reference to the sling 100. Any of such configurations may adopt any of the materials suitable for the sling 100 for use with the anchors/dilators of the invention.

FIGS. 3A-4B show alternative approaches for attaching a sling end to a proximal end of an anchor/dilator, such as the tissue anchors described above with regard to FIGS. 2A-2E, those described below with respect to other illustrative embodiments, and their smooth surfaced dilator counterparts. FIG. 2A shows an exemplary sling assembly end 180 including a sling end 184 and an exemplary tissue anchor 182. As shown, the mesh end 184 wraps around and affixes to a proximal end 186 of the anchor 182. Such affixation may, for example, be by way of gluing, heat bonding, shrink tubing, or any other suitable mechanism. As shown in the cross-sectional view of FIG. 3B, the anchor 184, like the anchors of FIGS. 2A-2E, includes an aperture 188 in its proximal end 186 for receiving a distal end of a delivery device shaft. In the alternative illustrative embodiment of FIGS. 4A and 4B, the anchor 194 includes a slot 196 extending distally from its proximal end 197. As shown in the cross sectional view of FIG. 4B, the slot 196 extends radially across the entire width of the anchor 194 to enable the end 198 of the sling 192 to slidably interfit within the slot 196. The slot 196 may be configured to be tight enough to capture the sling end 198. Alternatively, it may include one or more textured surfaces or include projections for capturing the sling end 198. In other illustrative embodiments, the sling end 198 may be affixed within the slot 196, for example, by way of gluing, heat bonding, shrink tubing, or any other suitable mechanism. As shown in FIG. 4B, the anchor 194 also includes an aperture 199 in its proximal end 197 for receiving a delivery device.

Figure 5D:
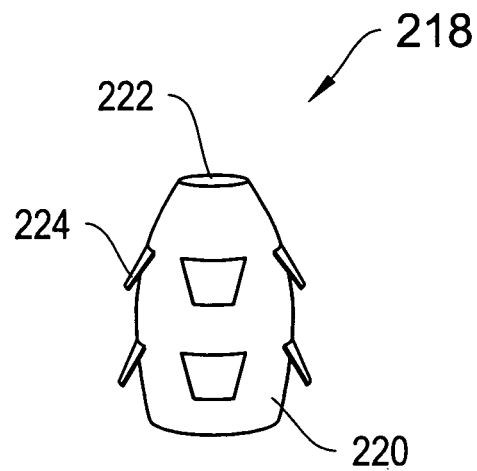

FIGS. 5A-5E depict additional illustrative tissue anchors according to the invention. Although they are depicted as having hollow bodies (e.g., a through lumen extending axially from a proximal end to distal end), this need not be the case. Each of the anchors of FIGS. 5A-5E may include any of the operable properties of any other anchors described herein and may be similarly sized to those of FIGS. 2A-2E. Turning to the drawings, FIG. 5A shows a hollow anchor 200 including a body 201 and various types of barbs 202, which in the illustrated embodiment include spikes and bristles 202. The anchor 200 includes a through-passage 203 extending between proximal and distal ends and may attach to a sling, such as the depicted sling 205 by any suitable mechanism. The barbs 202 of the anchor 200 are both axially and radially aligned, in a similar fashion to those described above with regard to FIGS. 2A-2E. The barbs 202 are relatively short (e.g., less than about 2 millimeters in length) and relatively wide (e.g., between about 1 millimeter and about 2 millimeters in width/diameter). Additionally, they have relatively flat (as opposed to pointed) terminal ends 207. According to another feature, the barbs 202 are flexible enough and oriented to compress against the body 201 of the anchor 200 during insertion, and are oriented to lift up and extend radially from the body 201 to resist removal from the tissue.

FIG. 5B shows a tissue anchor 209 according to another illustrative embodiment of the invention. In a similar fashion to the anchor 200, the anchor 209 includes an axially extending through passage 206. It also includes radially projecting barbs 208, which are oriented relative to the body 204 in a similar fashion to the way the projections 202 are oriented relative to the body 201 of the anchor 200. As in the case of the projections 202, the projections 208 are also flexible enough to deflect/compress against the body 204 of the anchor 209 during insertion into tissue and to lift up and resist reverse movement out of the patient's tissue. The projections 208 are of similar length as, but much narrower than the projections 202, being for example less than about a millimeter in diameter/width. As in the case of the anchor 200, the projections 208 align both axially and radially.

FIG. 5C shows an anchor 210 according to a further illustrative embodiment of the invention. As shown, the anchor 210 includes a through-aperture 214, a body 212, and a single row of axially projecting bristles 216 of the type shown at 208 in FIG. 5B. In this illustrative embodiment, the anchor 210 is but one-third the length of the anchors 200 and 209. More particularly, according to the illustrative embodiment, the anchor 210 is less than about 1.5 centimeters in length.

FIG. 5D shows an anchor 218 according to an alternative embodiment of the invention. In this embodiment, the anchor 218 includes a through-aperture 222, a body 220 and two rows of radial projections 224. The radial projections 224 have the same deflection and tissue engagement properties as those discussed with regard to FIGS. 5A-5D and, like the projections 202 of FIG. 5A, are relatively short (e.g., less than about 2 millimeters in length) and relatively wide (e.g., between about 1 millimeter and about 2 millimeters in width/diameter).

Figure 5E:
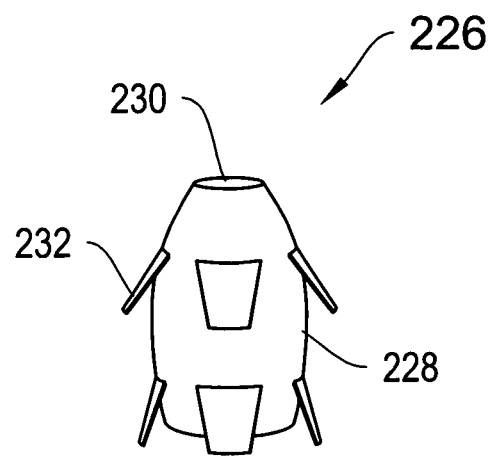

FIG. 5E shows an anchor 226 according to another alternative embodiment of the invention. As shown, the anchor 226 also includes a through aperture 230, a body 228 and two rows of radial projections 232. The only difference between this embodiment and the embodiment of FIG. 5D is that the projections 232 are relatively long (e.g., greater than or equal to about 2 millimeters in length) and relatively wide (e.g., between about 1 millimeter and about 2 millimeters in width/diameter).

Figure 5F:
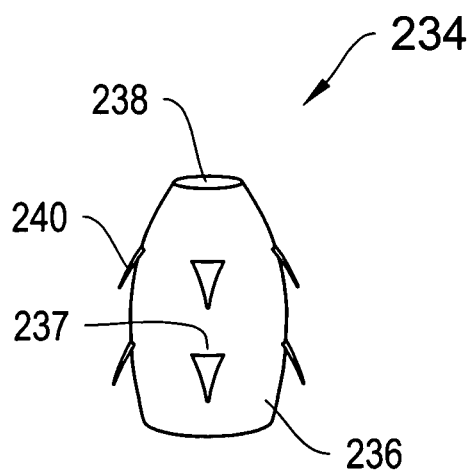

FIG. 5F shows an anchor 234 according to a further illustrative embodiment of the invention. As shown, the anchor 234 includes a body 236, an axially extending through-aperture 238 and radial projections 240. The anchor 234 has substantially the same properties as the anchors 218 and 226 of FIGS. 5D and 5E, respectively, except that the radial projections 240 are pointed rather than being squared-off like the projections 202, 224, and 232. According to the illustrative embodiment, the projections have an initial width at a base 237 comparable to the width of the projections 224 and 232, and have a length similar to that of the projections 224. The pointed tips of the projections 240 further facilitate the projections 240 engaging with tissue to oppose being pulled out of the patient's tissue once implanted.

Figure 5G:
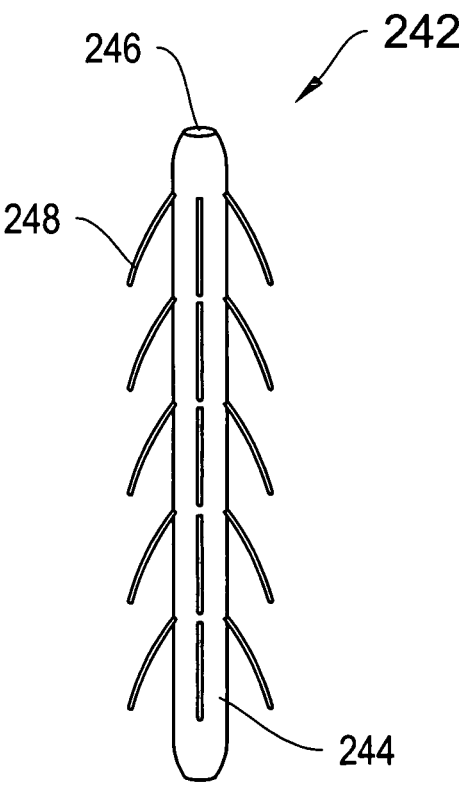

FIG. 5G shows another illustrative anchor 242, in which the anchor includes a relatively long (e.g., between about 2.5 centimeters and about 3.5 centimeters) body 244 and five rows of relatively long (e.g., greater than about 5 millimeters) radial projections 248. As in the case of the above described examples, the anchor 242 includes a radially extending through-passage 246.

Figure 6A:
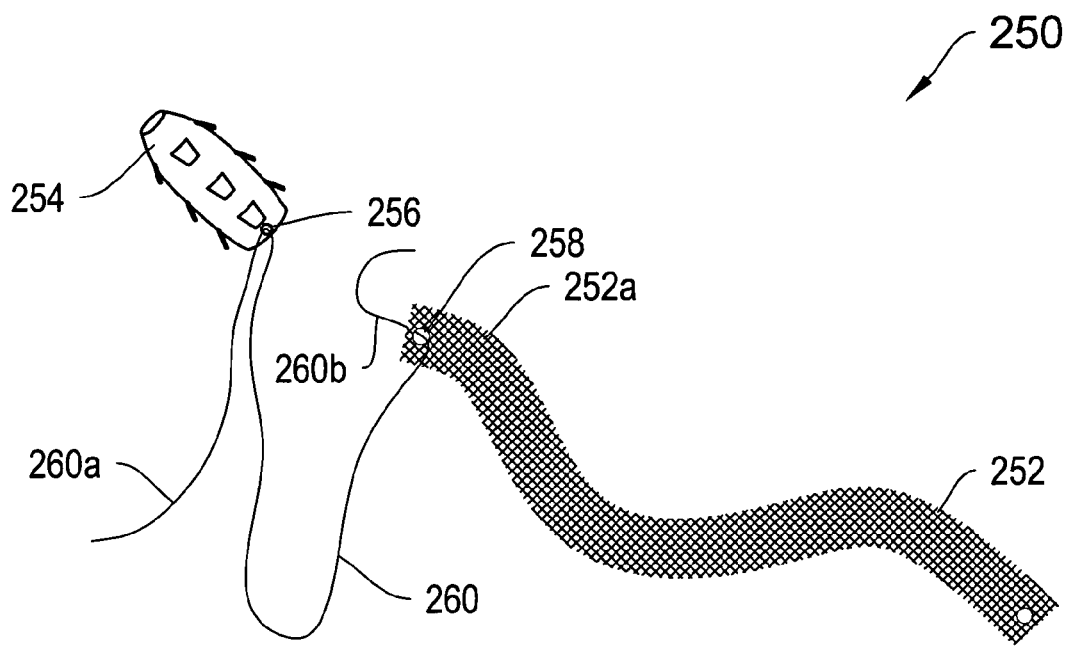
FIGS. 6A-6D depict approaches for affixing a soft tissue anchor/dilator to a sling end in such a way as to provide for sling assembly length/tension adjustment according to various illustrative embodiments of the invention.

Having described various illustrative tissue anchor configurations, FIGS. 6A-6D show approaches for affixing a soft tissue anchor/dilator to a sling end in such a way as to provide for sling assembly length/tension adjustment according to various illustrative embodiments of the invention. More specifically, FIG. 6A shows a sling assembly 250 including a sling 252 and an anchor 254. The anchor 254 includes a radial aperture 256, or other suitable aperture, in its side wall near its proximal end. A first end 260a of a filament 260 threads through the aperture 256, and a second end 260b of the filament 260 threads through an aperture 258 in the sling end 252a. The aperture 258 in the sling end 252a may be, for example, a gap in a mesh or may be purposefully formed and optionally reinforced. The length of the filament 260, and thus the overall length of the sling assembly 250 (i.e., from anchor/dilator distal tip to anchor/dilator distal tip) may be adjusted by pulling on the filament terminal ends 260a and 260b and securing them. In some configurations, they may be secured together, for example, by clipping, tying, gluing or applying another suitable mechanism. By way of example, in one configuration, the filament ends 260a and 260b are tied together in a one-way slip knot, which easily slides to reduce the length of the section of the filament 260 extending between the sling end 252 and the anchor 254, but not to extend the length of that section.

Figure 6B:
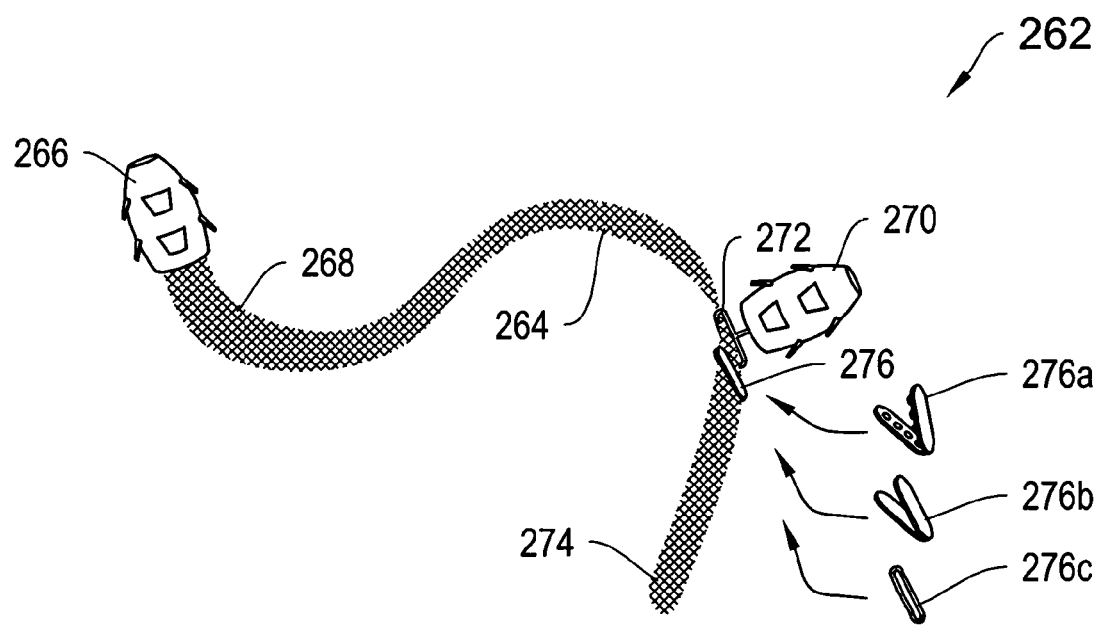

FIG. 6B shows an adjustable-length sling assembly 262 according to another illustrative embodiment of the invention. In this illustrative embodiment, the sling assembly 262 includes a sling 264 and first 266 and second 270 tissue anchors. The first tissue anchor 266 affixes to a first end 268 of the sling 264 in any suitable manner. The second tissue anchor 270 includes a loop 272 at its proximal end. In operation, the second end 274 of the sling 264 is inserted through the loop 272 and the anchor 270 is slid into a desired position along the length of the sling 264. Once the anchor is in position, the anchor 270 may be secured in place, for example, with: a snap-fit clip 276a having, for example, a textured inner surface projection from its inner surface; a vascular clip 276b; or a staple 276c. As shown, the clip 276a or 276b, or the staple 276c, may be placed on the sling 264 next to the anchor 270 on the sling-end 274 side of the anchor 270 to stop the anchor 270 from sliding along the sling 264 in a lengthening direction and/or from sliding off the sling 264 altogether. In other configurations, the loop 272 may be sutured, glued or otherwise secured in place on the sling 264. Once the anchor 270 is secured, the excess sling material may be trimmed from the sling end 274.

Figure 6C:
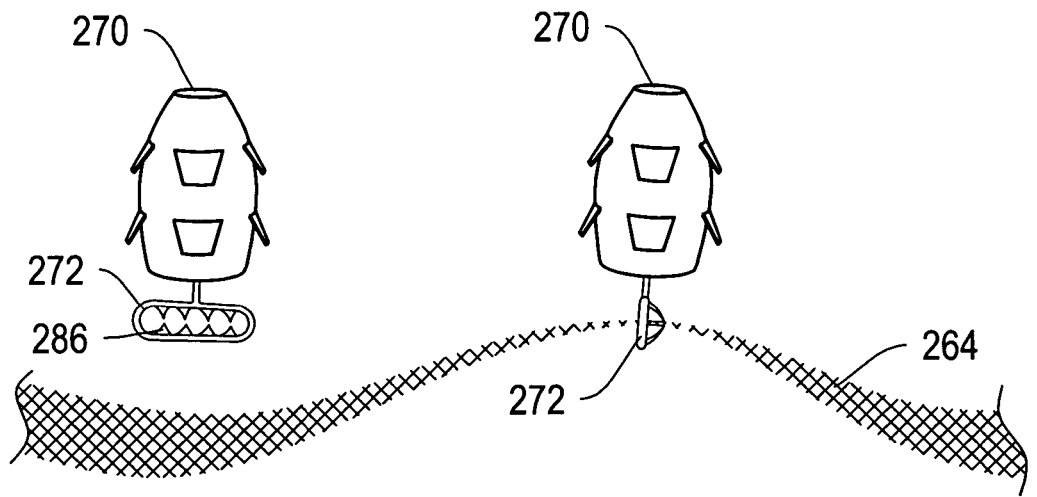

As shown in FIG. 6C, the loop 272 may include angled spikes or teeth 286 that are oriented and sized to enable the loop 272, and thus the anchor 270, to slide onto the sling 264, but not allow the loop 272 to slide in an opposite (e.g., a lengthening) direction.

Figure 6D:
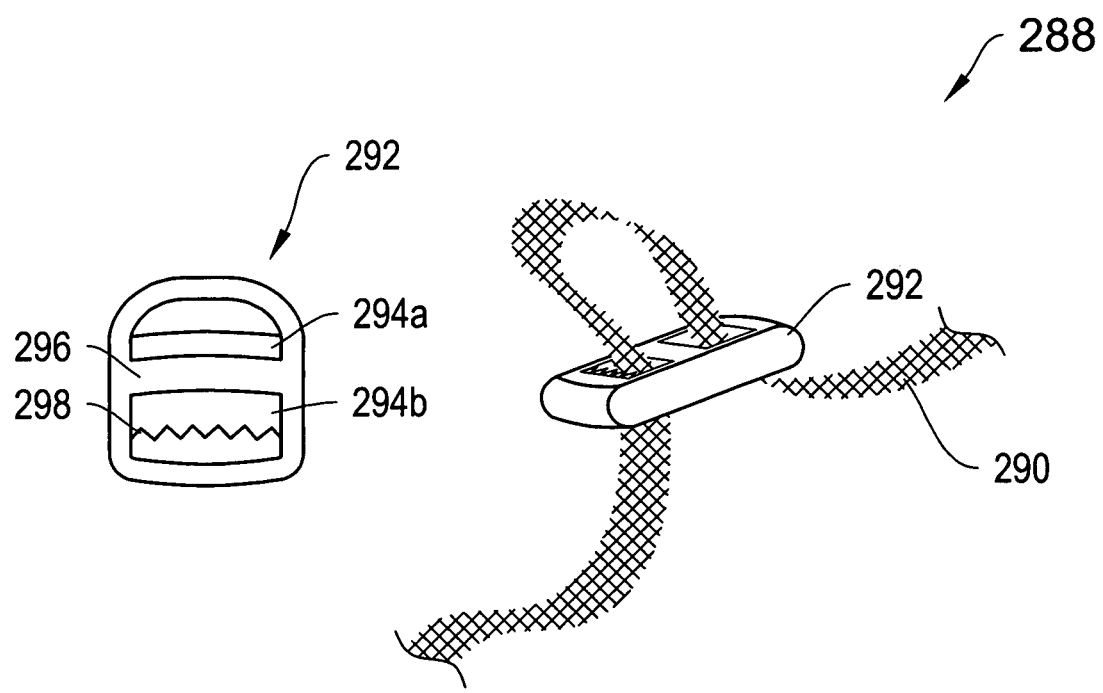

FIG. 6D shows another alternative assembly 288 in which a one-way buckle 292 is employed to adjust the length/tension of a sling 290. The buckle 292 may be similarly shaped to those employed on backpacks, but sized-reduced for the sling 290. As depicted, the buckle 292 includes first 294a and second 294b slots, defined by a cross bar 296. The surfaces forming the first slot 294a are substantially smooth, while the slot 294b includes a serrated surface 298. In operation, a sling end 290 passes into the slot 294b from the bottom of the buckle 292 over the cross bar 296 and down into the slot 294a. According to the illustrative embodiment, the buckle 292 may be, or may be attached to, the anchor loop 272. Alternatively, the buckle 292 may be formed integrally with or otherwise attached to the body of an anchor/dilator such as anchor 270, or its projectionless/projection reduced dilator counterpart. In other configurations, the buckle 292 is located on a sling end, such as the sling end 290, independent from the sling end 290 passing through a loop 272 or other suitable structure on the anchor 270. In further configurations, the one-way buckle 292 may be placed at any suitable location along the length of a sling.

Figure 7A:
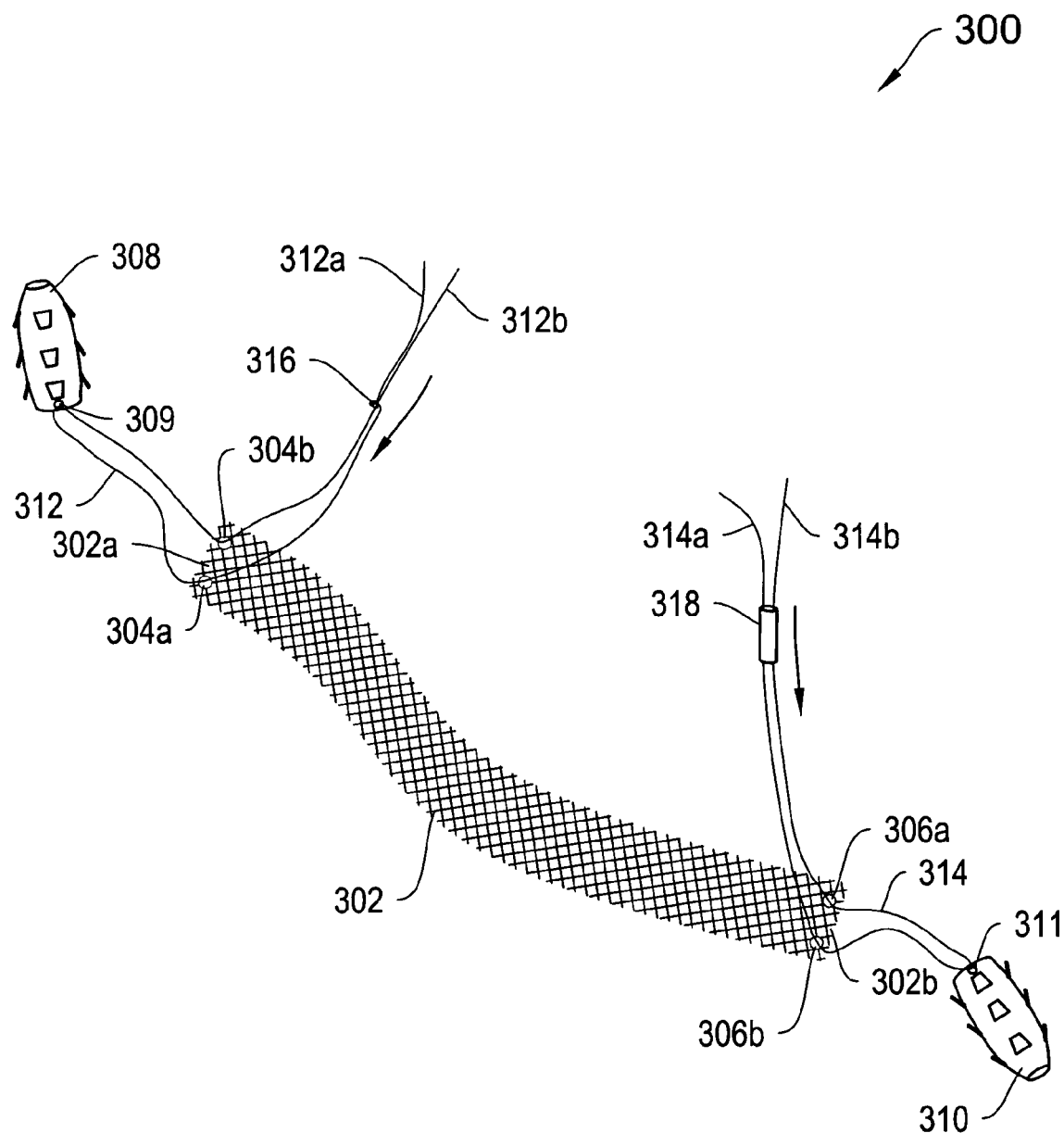
FIGS. 7A-7C depict approaches for length/tension adjusting an implantable sling assembly using filaments, for example, tied in one way knots and/or interwoven with the sling material according to illustrative embodiments of the invention.
Figure 7B:
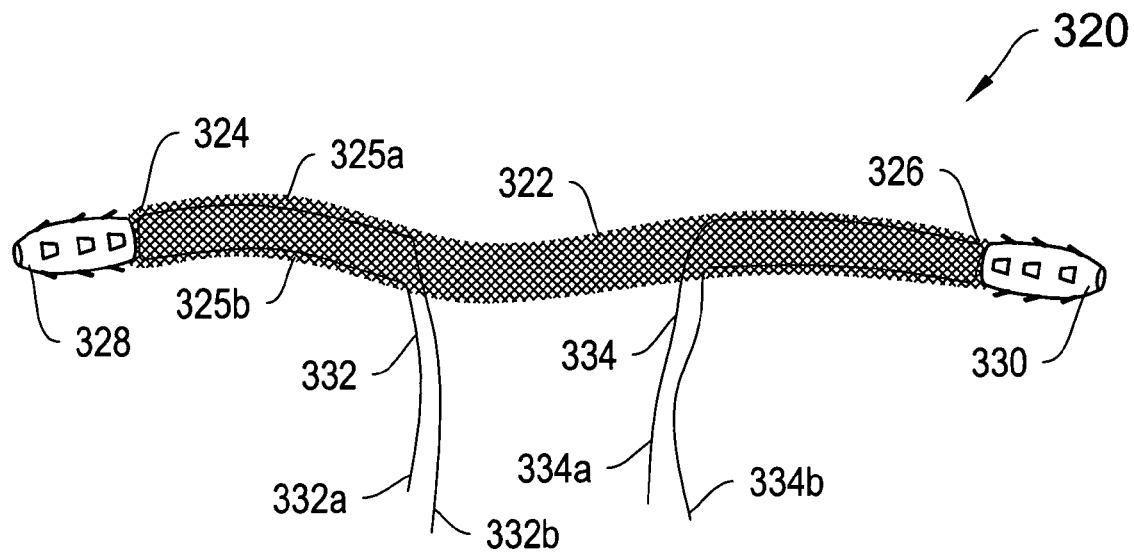
Figure 7C:
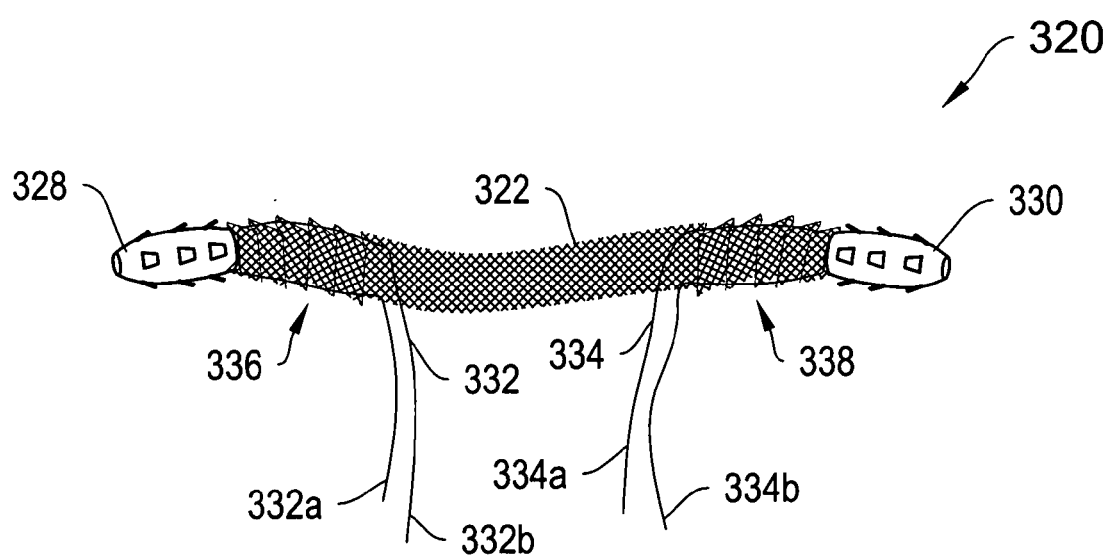

FIGS. 7A-7C depict approaches for length/tension adjusting of an implantable sling assembly using filaments, for example, tied in one-way knots and/or interwoven with the sling material according to illustrative embodiments of the invention. More particularly, FIG. 7A shows a sling assembly 300 including a sling 302, two tissue anchors 308 and 310, and two filaments 312 and 314. As shown, according to the illustrative embodiment, the filament 312 threads through an aperture 309 or other suitable structure in the anchor 308. Each end 312a and 312b of the filament 312 threads through a respective aperture 304a and 304b in the sling end 302a. The further the filament ends 312a and 312b are drawn through the sling end apertures 304a and 304b, the closer to the sling end 302a the anchor 308 is drawn, once again adjusting the overall (e.g., anchor tip to anchor tip) length of the sling assembly 300. As in the prior example, the filament ends 312a and 312b may be secured together to hold the length of sling assembly 300 constant. The filament ends 312a and 312b may be secured, for example, by tying, tying in a one-way slip knot (shown at 316), gluing, clipping, crimping, or passing through a one-way adjustable holder, such as the holder 318 or through another suitable mechanism. The anchor 310 may be affixed directly to the sling end 302b in any suitable manner or, as shown, tethered to the sling end 302b in a similar fashion to the anchor 308. More specifically, the filament 314 may be passed through the aperture 311 of the anchor 310. The filament ends 314a and 314b may then be passed through respective sling end apertures 306a and 306b and secured through the one-way suture holder 318. Once the filament lengths have been adjusted, excess filament may be trimmed off. Any suitable filament may be employed, including any suitable suture material. According to one illustrative embodiment, the sling assembly 300 employs a 3-O prolene suture for the filaments 312 and 314.

FIGS. 7B and 7C show a sling assembly 320 in a first elongated state and in a second accordioned state, respectively. Referring first to FIG. 7B, the assembly 320 includes a sling 322, two tissue anchors 328 and 330, and two filaments 332 and 334. As shown, each anchor 328 and 330 attaches to a respective sling end 324 and 326 by any suitable mechanism. The filament ends 332a and 332b thread through respective apertures (which may be openings in a mesh sling material or may be specifically formed for that purpose) in the sling end 324. Similarly, the filament ends 334a and 334b thread through corresponding respective apertures in the sling end 326. The filament end 332a interweaves with the sling material toward the second sling end 326 along at least a portion of the length of the sling 322 near a first sling edge 325a. Similarly, the filament end 332b interweaves with the sling material toward the second sling end 326 along at least a portion of the length of the sling 322 near a second sling edge 325b. The filament 334 similarly interweaves with the sling material in a direction from the second sling end 326 toward the first sling end 324.

Referring also to FIG. 7C, in response to pulling on the terminal ends 332a and 332b of the filament 332, a section 336 of the sling 322 accordions to reduce the length of the sling 322. Similarly, in response to pulling on the terminal ends 334a and 334b of the filament 334, a section 338 of the sling 322 accordions to further reduce the length of the sling 322. The filament ends may be secured by any suitable mechanism, including any of those described herein once a desired sling length is achieved. In some applications, the sling assembly 320 is inserted into the body in the expanded state of FIG. 7B, and shortened to a desired length subsequent to placement. In other applications, the sling assembly is inserted into the body in the accordioned state of FIG. 7C, and lengthened to a desired length during placement. In other applications, a combination of lengthening and shortening is employed during sling placement.

In some configurations, an interwoven filament is employed in only one end of the sling assembly 320, with the other end remaining at a fixed location. In some such embodiments, the filament-interwoven, and thus accordionable sling section may extend for substantially the entire length of the sling 322. In other illustrative embodiments, the filament is interwoven with half or less of the length of the sling 322. In some illustrative embodiments, the interwoven filaments pass first through an aperture or other suitable structure on an anchor/dilator, for example, to attach the anchor 328 or 330 to the sling.

Figure 8A:
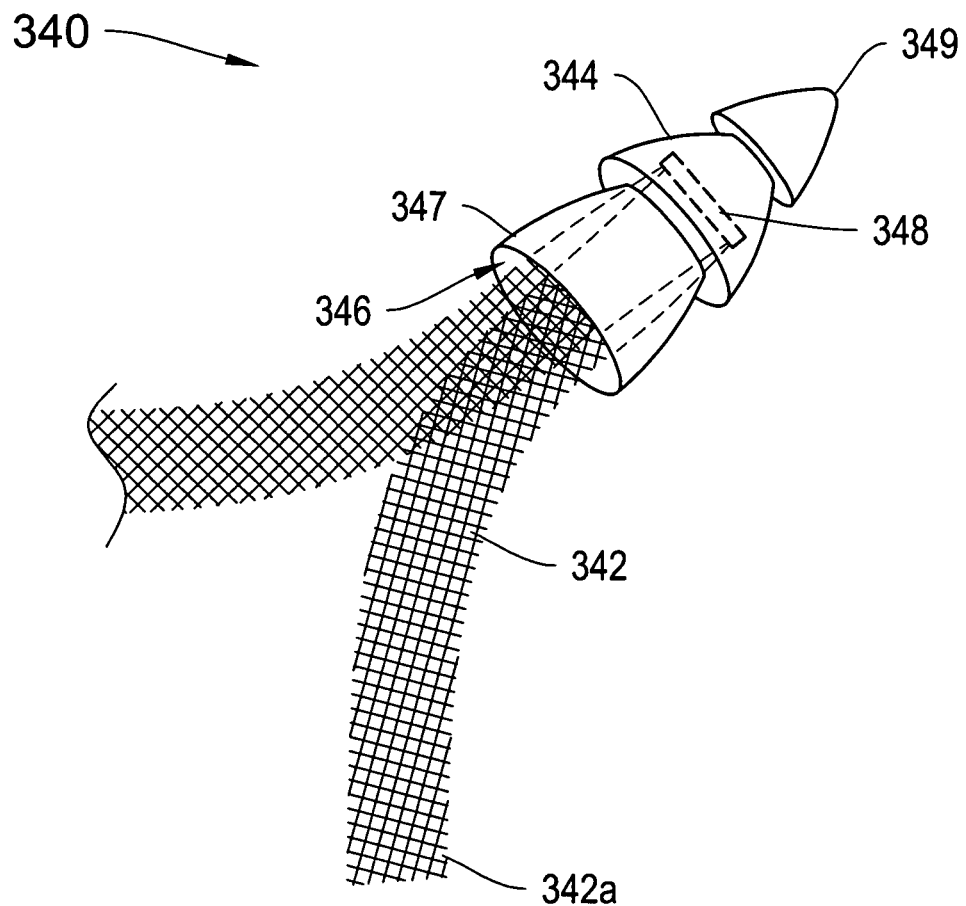
FIGS. 8A-8B are perspective and side views, respectively, of a sling assembly end including a soft tissue anchor/dilator with an internal bar about which sling length/tension may be adjusted according to an illustrative embodiment of the invention.
Figure 8B:
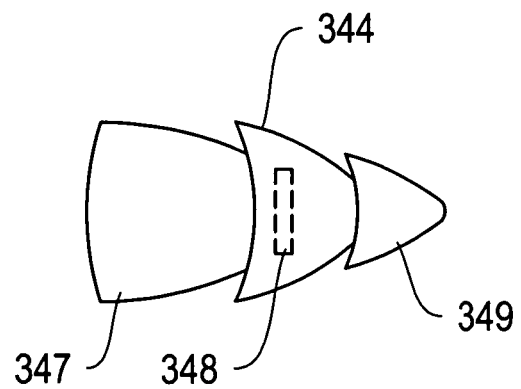

FIGS. 8A-8B show perspective and side views, respectively, of a sling assembly 340 including a soft tissue anchor 344 with an internal bar 348 about which the length/tension of the sling 342 may be adjusted according to an illustrative embodiment of the invention. As shown, an anchor 344 includes a hollow inner portion 346 extending axially from a proximal end 347 at least part way to a distal end 349 of the anchor 344, and a bar 348 or other structure extending radially across the hollow portion 346 inside the anchor 344. In this embodiment, a sling end 342a passes into the hollow portion 346 via a proximal opening in the anchor 344, loops around the bar 348 and back out of the proximal end 347 of the anchor 349. In some configurations, the bar 348 may include spikes, bristles or other projections, such as those described above, for allowing the sling end 342a to pass through the hollow portion 346 in a sling shortening direction, but impedes the sling 342 from passing in an opposite sling lengthening direction. In other configurations, the sling end 342 may be secured, for example, by way of a clip, staple or suture, outside the anchor 344 (e.g., in a similar fashion to that discussed with reference to FIG. 6B) subsequent to the anchor 344 being placed at a desired location along the length of the sling 342. As in the other illustrative embodiments, excess sling material may be trimmed off subsequent to securing the position of the anchor 344.

Figures 9A, 9B:
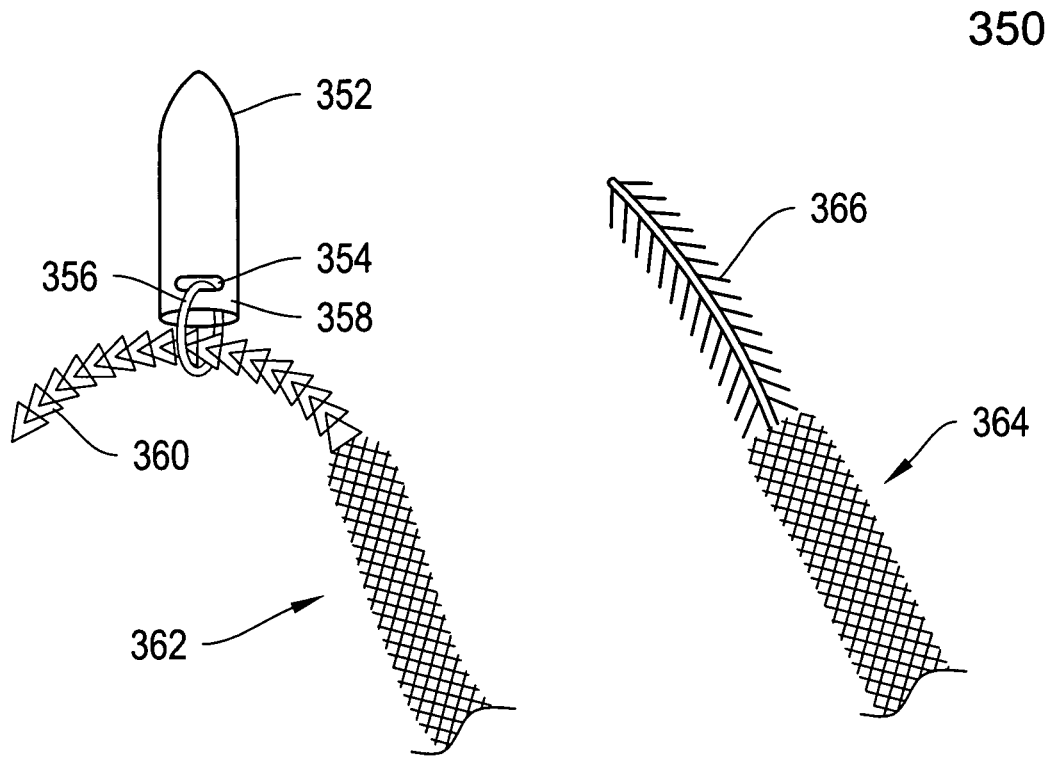
FIGS. 9A-9B show a soft tissue anchor/dilator having a loop for receiving a ridged/jagged element attached to an end of a sling for providing sling length/tension adjustment according to another illustrative embodiment of the invention.

FIGS. 9A-9B shows an end of a sling assembly 350, including soft tissue anchor/dilator 352 having a loop 356 for receiving an elongated ridged/jagged element 360 or 366 attached to an end of a sling 362 or 364 for providing sling length/tension adjustment according to another illustrative embodiment of the invention. As mentioned above and as shown in FIGS. 9A and 9B, the structure 352 need not have any radial projections, and may instead either rely on orientation for anchoring, or dissolve altogether to leave the sling ends to hold the sling in place. According to this illustrative embodiment, the elements 360 and 366 may have any anchor-like configuration, for example, including directionally oriented spikes, bristles or other projections positioned to slide into the anchor loop 356, and to impede sliding out of the loop 356. The anchor/dilator 352 may be slid along the length of the anchor-like element 360 or 366 to adjust the overall (anchor/dilator distal tip to anchor/dilator distal tip) length of the sling assembly 350. The elements 360 and 366 may attach to the respective slings 362 and 364 by way of any suitable mechanism, such as any of those employed to attach a tissue anchor/dilator to a sling end.

Figure 10:
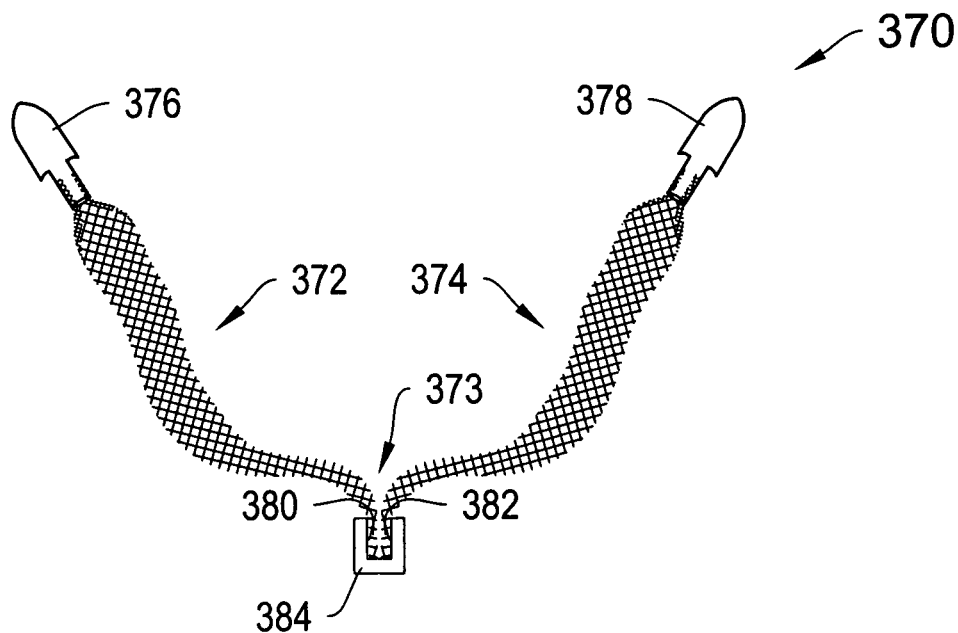
FIG. 10 shows a sling assembly including two sections attached together at an intermediate location to provide for adjustable sling/tension according to another illustrative embodiment of the invention.

FIG. 10 shows a sling assembly 370 including two sling assembly sections 372 and 374 attached together at an intermediate location 373 to provide for adjustable sling/tension according to another illustrative embodiment of the invention. According to the illustrative embodiment, the assembly section 372 includes an anchor/dilator end 376 and a free end 380. Similarly, the assembly section 374 includes an anchor/dilator end 378 and a free end 382. One or both of the free ends 380 and 382 may be cut to a desired length, and then attached, for example, by way of the clip 384. In other illustrative embodiments, the free ends 380 and 384 are attached, for example, by way of suturing, tying, stapling, gluing or heat melting/bonding, or other suitable mechanism.

Figure 11:
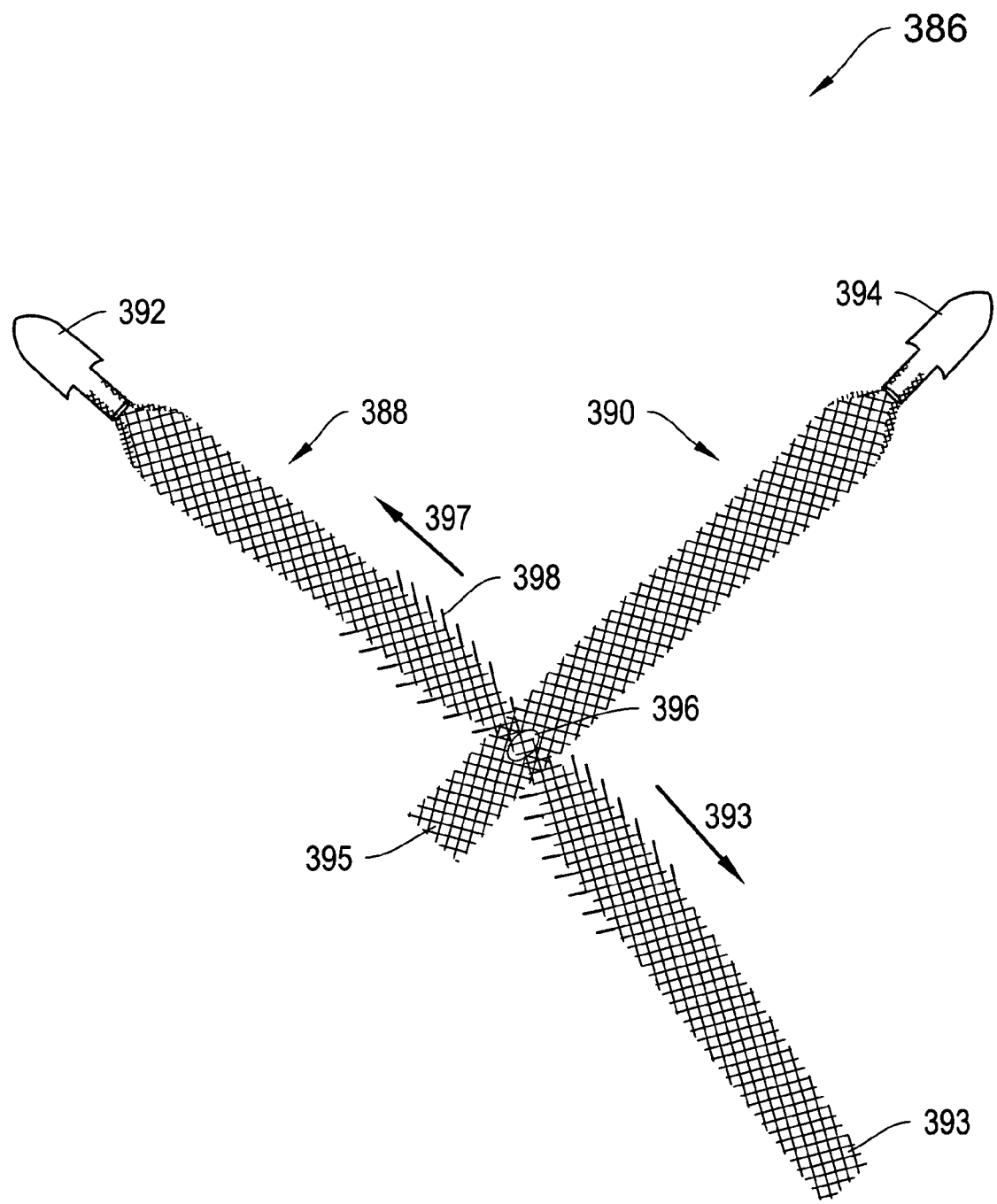
FIG. 11 shows another two section sling assembly adapted for adjustably interfitting at an intermediate location to provide for adjustable sling length/tension according to a further illustrative embodiment of the invention.

FIG. 11 shows another two-section adjustable length/tension sling assembly 386. As in the case of the illustrative embodiment of FIG. 10, the assembly section 388 includes an anchor/dilator end 392 and a free end 393, and the assembly section 390 includes an anchor/dilator end 394 and a free end 395. The assembly section 388 also includes bristles, spikes or tangs 398 extending from its edges along at least a portion of its length. The bristles may be formed, for example, from sling mesh filaments, which optionally are treated to stiffen them. In other embodiments, the bristles may be bonded to the edges of the sling assembly section 388. The assembly section 390 includes an aperture 396 near its free end 395. The aperture 396 may be, for example, a gap between filaments of a mesh sling material or may be purposefully formed, and optionally reinforced.

In operation, the anchor/dilator end 392 interfits through the aperture 396. The aperture 396 is sized to be large enough to pass the anchor/dilator end 392 but small enough to engage the projections 398. The projections 398 are oriented for and flexible enough to pass through the aperture 396 behind the anchor/dilator end 392 in the direction of the arrow 397, but inhibit the assembly section 388 from sliding back through the aperture 396 in the direction of the arrow 399.

Figure 12A:
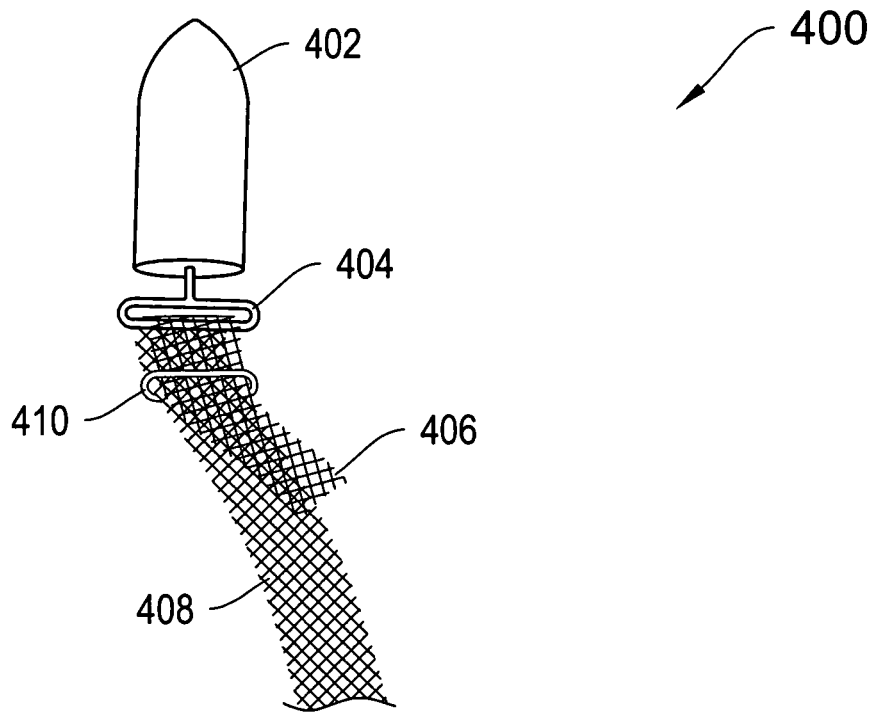
FIGS. 12A-12B show adjustable length/tension sling assemblies having an end clip for affixing a sling end to a soft tissue anchor/dilator at a desired sling length according to another illustrative embodiment of the invention.
Figure 12B:
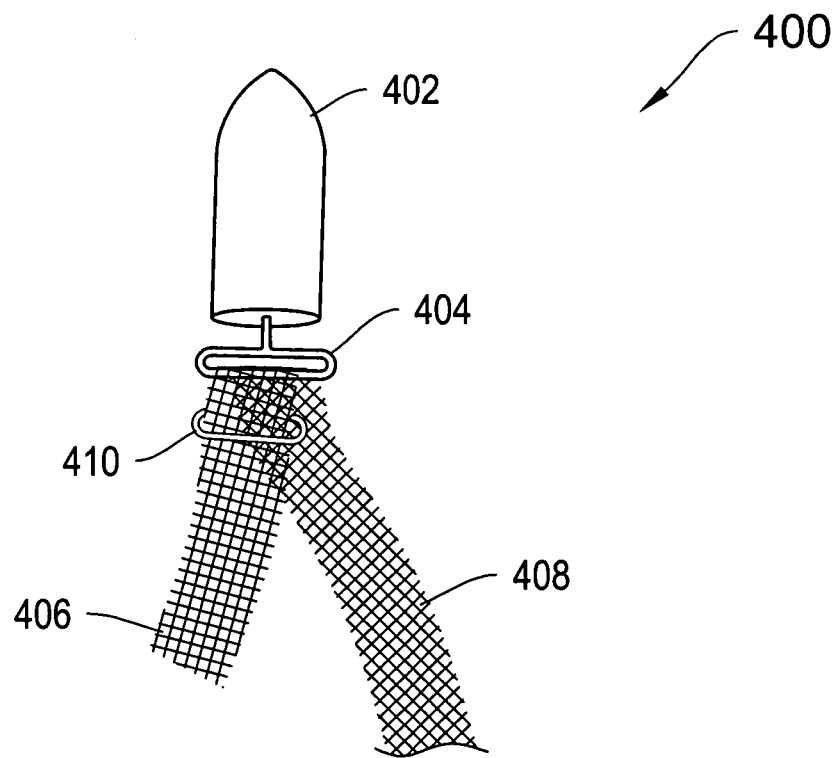

FIGS. 12A-12B show an end of an adjustable length/tension sling assembly 400, including a sling 408 having an end 406 and employing a soft tissue anchor/dilator 402 with a loop section 404 according to another illustrative embodiment of the invention. As shown in FIG. 12B, the sling 408 may be secured within the loop 404 by placing any suitable securing mechanism 410 next to the loop 404 on the free end 406 side of the anchor/dilator 402, in a similar fashion to that described with regard to FIG. 6B. However, as shown in the alternative embodiment of FIG. 12A, the clip 410 may be placed around both the sling 408 and the end section 406. In some implementations, the securing mechanism of FIG. 12A may be a suitably-sized elastic band or O-ring. In this way, the fastener 410 need not be a permanent fastener and may continue to allow for sling length adjustment even after the fastener 410 is slid into place, in much the same way as a buckle arrangement would allow.

Figure 13A:
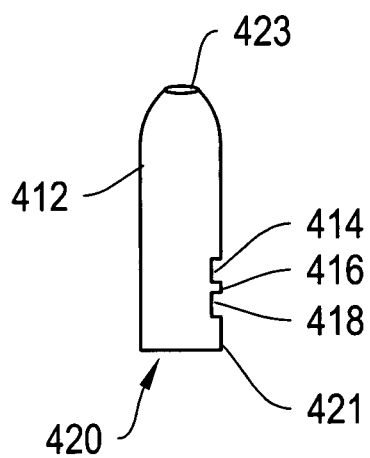
FIGS. 13A-13B depict soft tissue anchor/dilator having a buckle in a side wall for interthreading with a sling end to provide for adjustable sling length/tension according to an additional embodiment of the invention.
Figure 13B:
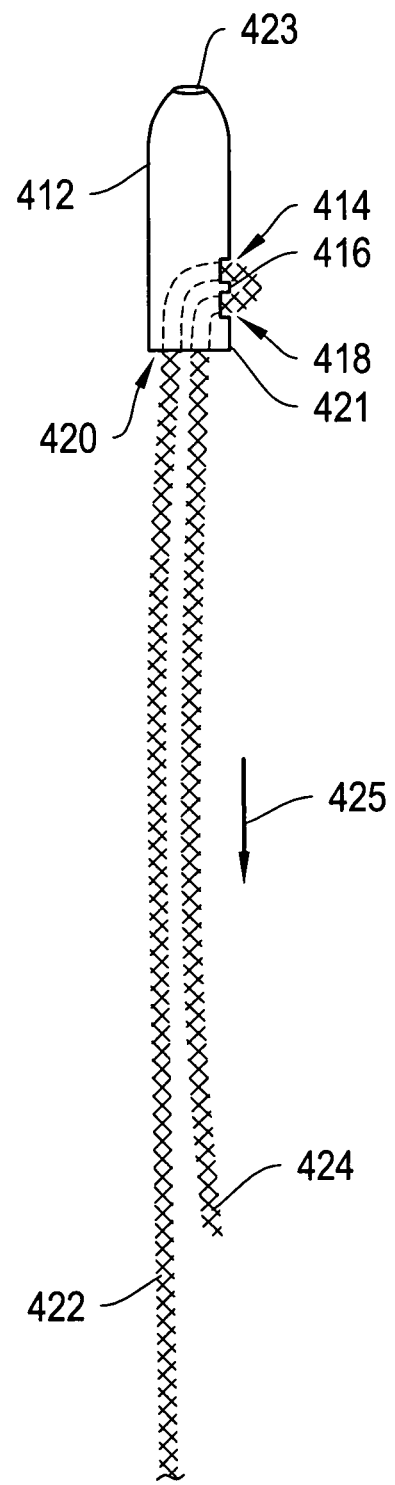

FIGS. 13A-13B depict soft tissue anchor/dilator 412 having a buckle formed in a side wall for interthreading with an end of a sling, such as the end 424 of the sling 422, to provide for adjustable sling length/tension according to an additional illustrative embodiment of the invention. As shown in FIGS. 13A and 13B, the anchor 420 includes a through-passage 420 extending between proximal 421 and distal 423 ends of the anchor/dilator 412. The anchor/dilator 412 also includes two substantially rectangular through-apertures 414 and 418 in the wall of the anchor/dilator 412. The apertures 414 and 418 are separated by a cross bar 416. As shown in FIG. 13B, the sling end 424 threads into the through-passage 420 at the proximal end 421 of the anchor/dilator 412. It then exits the through-passage 420 through the aperture 414, loops over the cross bar 416, and re-enters the through-passage 420 through the aperture 418. By pulling on the sling end 424 in the direction of the arrow 425, the length of the sling 422 may be shortened. Similarly, by feeding the end 424 in an opposite direction, the sling 422 may be lengthened. The buckle structure of FIGS. 13A and 13B may also include any of the operable features described above with regard to FIG. 6D. Additionally, although the passage 420 is depicted and described as a through-passage, this need not be the case.

FIGS. 14A-14B depict a sling assembly 426 employing an arrangement of interlocking, stackable soft tissue anchors/dilators 430, 440 and 446 for providing adjustable sling assembly length/tension according to another embodiment of the invention. As shown in FIG. 14A, a first tissue anchor/dilator 430 attaches to an end of a sling 428 in any suitable manner and includes opposing apertures 434a and 434b in its side wall near a proximal end. It also includes small radially extending barbs 436a and 436b in its side wall near a distal end 433. The anchor/dilator 430 also includes tissue engaging projections 432 of the type described above. Similarly, the anchor/dilator 440 includes opposing apertures 438a and 438b in its side wall near its proximal end 441, axially extending barbs 444a and 444b in its side wall near its distal end 443. As may be the case with any of the anchor/dilator structures discussed herein, the anchor/dilator 440 includes no tissue engaging projections. In operation, the proximal end 441 of the anchor/dilator 440 interfits over the distal end 433 of the anchor/dilator 430, with the barbs 436a and 436b snap fitting into the apertures 438a and 438b. In this way the two anchors/dilators 430 and 440 may be stacked to extend the overall length of the sling assembly 426.

In a similar fashion, the anchor/dilator 446 includes apertures 452a and 452b in its side wall near its proximal end 457 and radially projecting barbs 450a and 450b in its side wall near its distal end 453. It also includes tissue-engaging barbs 448. In operation, the proximal end 457 of the anchor/dilator 446 can interfit over the distal end 443 of the anchor/dilator 440, with the proximal apertures 452a and 452b snap fitting onto the radial projections 444a and 444b to further extend the anchoring/dilating mechanism and further increase the overall length of the sling assembly 426. According to another feature, the anchors/dilators 446 and/or 440 may also be removed from the anchor/dilator 430 to shorten the sling assembly 426. According to one illustrative embodiment, each of the anchors/dilators 430, 440 and 446 may be between about 2 centimeters and about 4 centimeters long. Additionally, they may be of differing sizes to provide for differing increments by which to adjust the sling-assembly length. The same or similar anchor/dilator configuration may be employed at the other end of the sling assembly 426, or alternatively, the other end of the sling assembly may employ a fixed length configuration.

Figures 15A, 15B:
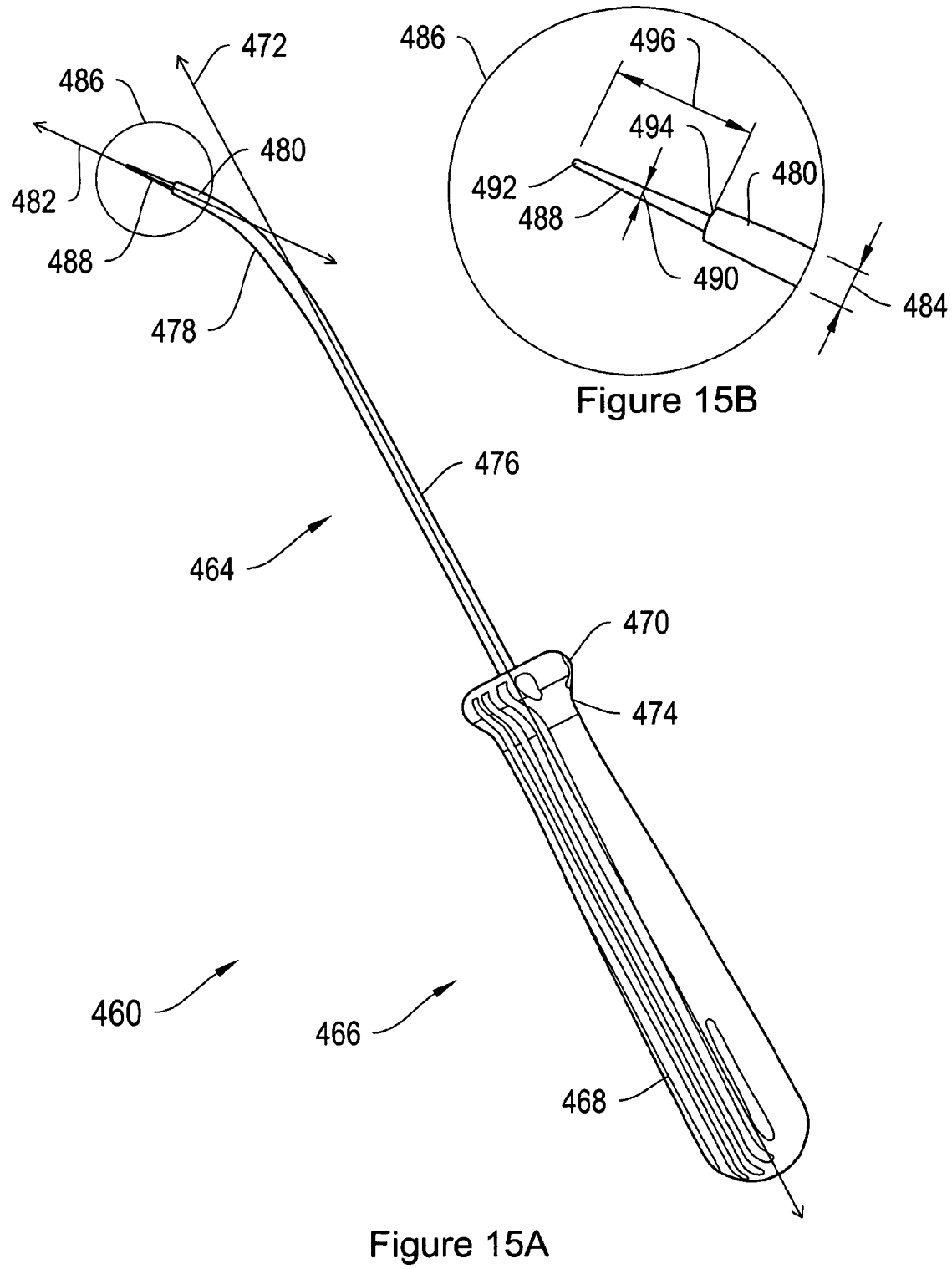
FIGS. 15A-15B show a delivery device including a shaft having a narrowed distal tip for interfitting with a soft tissue anchor/dilator of a sling assembly according to an illustrative embodiment of the invention.

FIGS. 15A-15B show a delivery device 460 for delivering a sling to an anatomical site within the body of a patient. The illustrative delivery device 460 includes a handle 466 and a shaft 464. The handle 466 includes a proximal end 468 and a distal portion 470 and extends substantially along an axis 472. The handle 466, as depicted, is substantially straight and tapers inward from the proximal end 470 to a distal location 474. The distal portion 470 of the handle 466 tapers outward from the distal location 474 to help prevent a medical operator's hand from slipping distally while using the device by grasping the handle 466. The shaft 464, as depicted, includes a first substantially straight proximal portion 476 attached to and extending distally from the distal end 470 of the handle 466, substantially along the axis 472. The illustrated shaft 464 also includes a curved portion 478 that extends distally from and curves away from the substantially straight proximal portion 476, and a second substantially straight portion 480 extending distally from the curved portion 478 and substantially along an axis 482. In illustrative embodiments, the axis 472 and 482 form a non-orthogonal angle relative to each other and lie substantially in a single plane. However, this need not be the case, and any suitable angle may be employed with the invention.

In certain embodiments, the shaft 464 may be, for example, substantially straight or may include one or more curved sections. Additionally, the shaft 464 may lie substantially in one plane or may be shaped to lie in multiple planes. The shaft 464 may be of substantially constant outside diameter 484 or may include portions of differing outside diameters. In various embodiments, the shaft 464 may include hooked and/or helical portions. The shaft may also be configured in various ways and/or include various features as described in the patents and patent applications mentioned and incorporated by reference herein.

FIG. 15B shows a magnified view of the distal section 486 of the shaft 464. The distal section 486 includes part of the substantially straight section 480 having an outside diameter 484, and a reduced diameter distal section 488 extending distally from the section 480 and having an outside diameter 490. The distal section 488 terminates in a distal tip 492. In illustrative embodiments, the diameter 490 is substantially smaller than the diameter 484, forming a radially extending shoulder 494 between the section 488 and the section 480. According to one feature, the shoulder 494 inhibits or impedes a tissue anchor/dilator located at the end of a sling assembly slidably engaged or associated with the section 488 from sliding proximally along the curved section 478 and first straight section 476 of the shaft 464 during implantation of the sling assembly. The distal tip 492 may be sharp enough to pierce tissue, or alternatively, relatively blunt. Additionally, the distal tip 492 may have a conical or any other suitable shape.

In one configuration, the shoulder 494 extends around the entire circumference of the shaft 464. In other configurations, the shoulder 494 extends around only a portion of the circumference. In both cases, the shoulder 494 extends far enough to provide a protuberance of sufficient size to impede the sling assembly end from sliding proximally along a substantial portion of the length of the shaft 464.

In alternative illustrative embodiments, the portion 488 may taper towards the distal end 492, or may have constant outside diameter 490, except, for example, for a conical tip. In other embodiments, the portion 486 may have an outside diameter that gradually decreases distally, instead of an abrupt decrease in outside diameter, such as the abrupt decrease between diameters 484 and 490 depicted in FIG. 1B.

According to various illustrative embodiments, the length 496 of the section 488 is between about 2 centimeters and about 4 centimeters long. In other illustrative embodiments, it is between about 1 centimeter and about 3 centimeters long. In further illustrative embodiments, the narrowed distal portion 488 has an outside diameter 490 of between about 0.03 inches and about 0.05 inches. In one illustrative embodiment, it has an outside diameter 490 of about 0.04 inches. According to other configurations, the portion 480 of the shaft 464 forming the shoulder 494 has an outside diameter 484 of between about 0.07 inches and about 0.1 inches. In one implementation, the outside diameter 484 of this portion 480 of the shaft is about 0.09 inches. According to one configuration, the total length of the shaft 464 is between about 7 centimeters and about 20 centimeters. In other configurations, the total length of the shaft 464 is between about 8 centimeters and about 12 centimeters.

Figure 16:
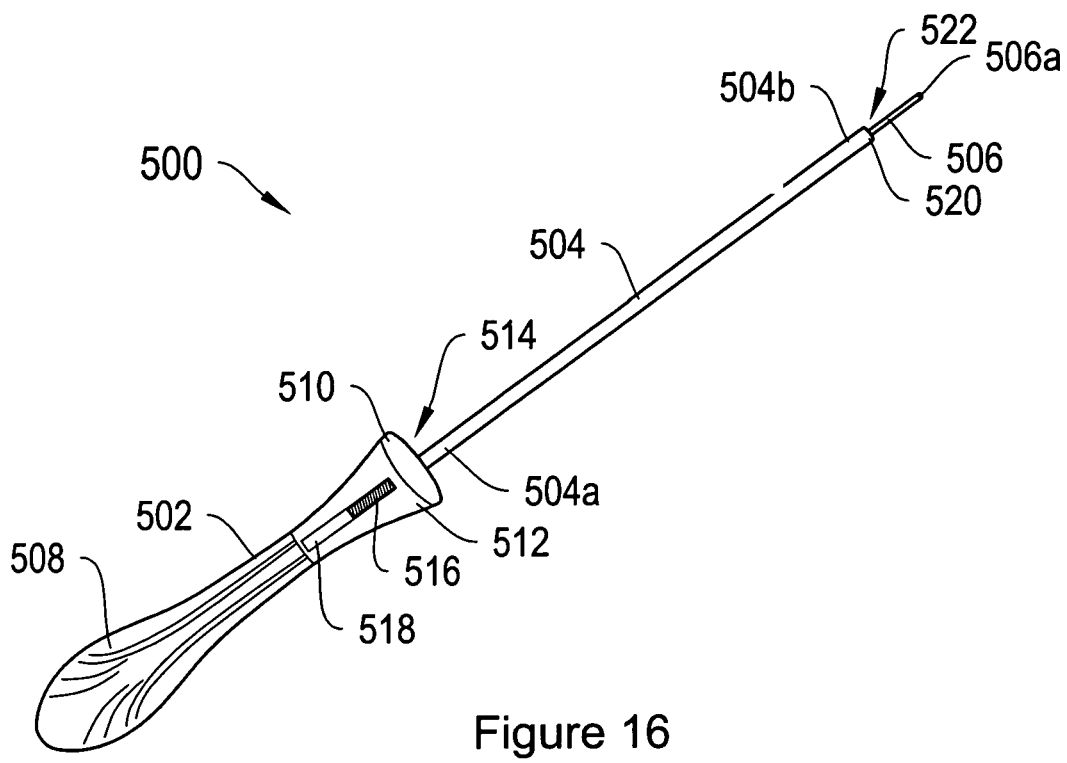
FIG. 16 shows a delivery device having a slidable inner shaft for engaging with a soft tissue anchor/dilator of a sling assembly according to an illustrative embodiment of the invention.

FIG. 16 shows a delivery device 500 for delivering a sling assembly to an anatomical location in the body of a patient according to another illustrative embodiment of the invention. The illustrative delivery device 500 includes a handle 502, a fixed position cannula 504 and a movable shaft 506. The handle 502 includes a proximal end 508 and a distal portion 510. The handle 502, as depicted, is substantially straight and tapers inward from the proximal end 508 to a distal location 512. The distal portion 510 of the handle 502 tapers outward from the distal location 512 to help prevent a medical operator's hand from slipping distally while grasping the handle 502. The cannula 504 has a proximal end 504*a* and distal end 504*b*, and extends distally from a distal most end 514 of the handle 502. The cannula 504 is substantially straight, but this need not be the case. In alternative embodiments, it may include any combination of curved sections and straight sections, and may extend into one, two or more planes. The shaft 506 interfits within the cannula 504 and mechanically couples at a proximal end to a slider 516 on the handle 502. An operator may slide the slider 516 axially within the slot to retract and extend the shaft 505 in and out of the cannula 504. With the shaft 506 extended, a distal most end 520 of the cannula 504 forms a shoulder 522 similar to the shoulder 494 formed between the shaft sections 480 and 488 of FIGS. 15A and 15B. According to some embodiments, the distal end of the shaft 506 may be sized and shaped similarly to the shaft section 488, while the cannula 504 may be sized and shaped similarly to any of the shaft sections 476, 478 and 480.

In operation, a tissue anchor/dilator of a sling assembly of the type described above interfits onto the distal end of the shaft 506 with the slider 516, and thus the shaft 506, in an extended position. The distal end of the delivery device 500, with a tissue anchor/dilator so interfitted may then be inserted into the body of a patient, for example, by way of an incision in the vaginal wall. The delivery device is advanced until the interfitted anchor/dilator is placed at a desired location. The slider 512 is then retracted to retract the shaft 506 into the cannula 504 and out of the tissue anchor/dilator. The delivery device is then removed from the patient to leave the tissue anchor/dilator and sling-assembly end placed at the desired location within the patient. The procedure may be employed with the other end of the sling assembly on the contralateral side of the body with the same or a different delivery device.

According to the illustrative embodiment, in an extended position, the exposed distal section of the shaft 506 is between about 2 centimeters and about 4 centimeters long. In other illustrative embodiments, it is between about 1 centimeter and about 3 centimeters long. In further illustrative embodiments, the narrowed distal section of the shaft 506 has an outside diameter of between about 0.03 inches and about 0.05 inches. In one illustrative embodiment, it has an outside diameter of about 0.04 inches. According to other configurations, the outside diameter of the cannula 504 at the distal end 520 is between about 0.07 inches and about 0.1 inches. In one implementation, the outside diameter of this portion of the cannula is about 0.09 inches. According to one configuration, the total distance from the distal end 514 of the handle 502 to the distal most tip 506*a* of the shaft 506, with the shaft extended is between about 7 centimeters and about 20 centimeters. In other configurations, the total distance is between about 8 centimeters and about 12 centimeters.

Figure 17:
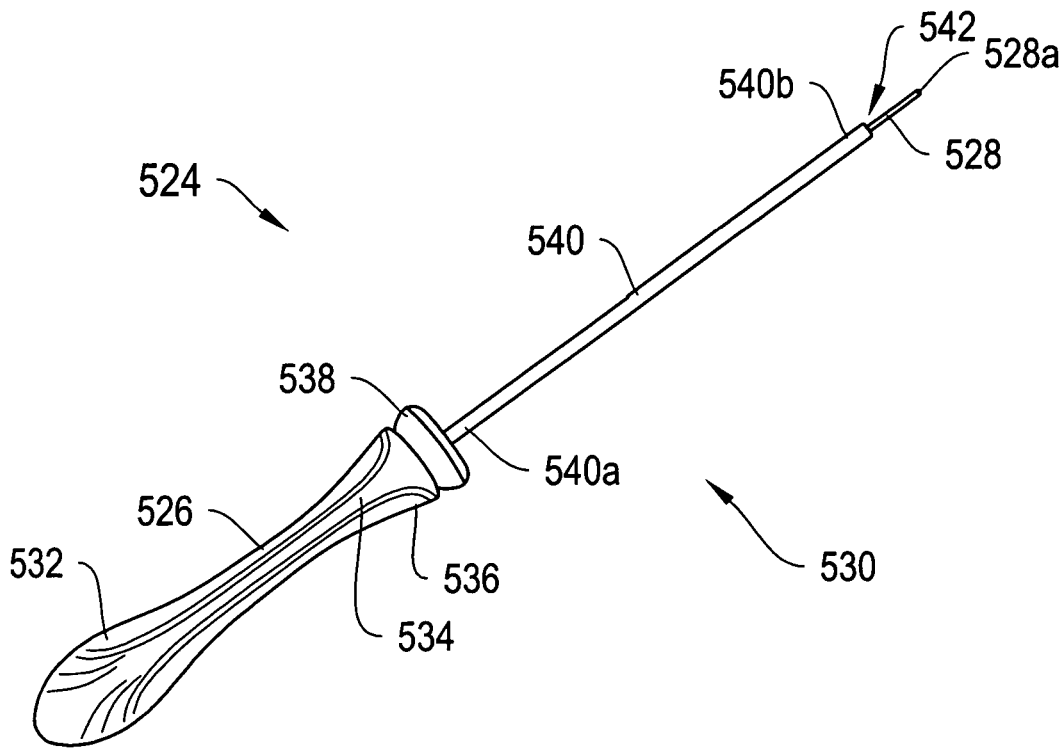
FIG. 17 shows a delivery device having a slidable outer cannula and a narrowed inner shaft for engaging with a soft tissue anchor/dilator of a sling assembly according to an illustrative embodiment of the invention.

FIG. 17 shows a delivery device 524 for delivering a sling assembly to an anatomical location in the body of a patient according to another illustrative embodiment of the invention. The illustrative delivery device 524 includes a handle 526, a fixed position shaft 528 and a movable pusher assembly 530. The handle 526 includes a proximal end 532 and a distal portion 536. The handle 526 is substantially straight and tapers inward from the proximal end 532 to a distal location 534. The distal portion 536 of the handle 526 tapers outward from the distal location 534 to help prevent a medical operator's hand from slipping distally while grasping the handle 525.

The pusher assembly 530 includes a user actuator 538 and to a cannula 540 extending distally from the user actuator 538 and over the shaft 528. The cannula 540 has a proximal end 540a and a distal end 540b, and is substantially straight, but this need not be the case. In alternative embodiments, the cannula 540 and the shaft 528 many include any combination of curved sections and straight sections, and may extend into one, two or more planes. An operator may slide the pusher actuator 538 axially to extend and retract the cannula 540 over the shaft 528 to alternatingly cover and uncover the distal end 528a of the shaft 528. With the cannula 540 retracted, a distal-most end 540b of the cannula 540 forms a shoulder 542 similar to the shoulder 494 formed between the shaft sections 480 and 488 of FIGS. 15A and 15B. According to some embodiments, the distal end of the shaft 528 may be sized and shaped similarly to the shaft section 488, while the cannula 540 may be sized and shaped similarly to any of the shaft sections 476, 478 and 480.

In operation, a tissue anchor/dilator of a sling assembly of the type described above interfits onto the distal end of the shaft 528 with the pusher actuator 538, and thus the cannula 540, in a retracted position. The distal end of the delivery device 524, with a tissue anchor/dilator so interfitted may then be inserted into the body of a patient, for example, by way of an incision in the vaginal wall. The delivery device is then advanced until the interfitted anchor/dilator is placed at a desired location. The pusher actuator 538 is then slid distally along the shaft 528 to cause the shoulder 542 of the cannula 540 to abut a proximal end of the anchor/dilator and push it off the distal end of the shaft 528. The delivery device 524 is then removed from the patient to leave the tissue anchor/dilator and sling-assembly end placed at the desired location within the patient. The procedure may be employed with the other end of the sling assembly on the contralateral side of the body with the same or a different delivery device.

According to the illustrative embodiment, with the pusher assembly 530 in a retracted position, the exposed distal section of the shaft 528 is between about 2 centimeters and about 4 centimeters long. In other illustrative embodiments, the exposed distal section of the shaft 528 is between about 1 centimeter and about 3 centimeters long. In further illustrative embodiments, the narrowed distal section of the shaft 506 has an outside diameter of between about 0.03 inches and about 0.05 inches. In one illustrative embodiment, it has an outside diameter of about 0.04 inches. According to other configurations, the outside diameter of the cannula 540 at the distal end 540b is between about 0.07 inches and about 0.1 inches. In one implementation, the outside diameter of this portion of the cannula is about 0.09 inches. According to one configuration, the total distance from the distal end of the cannula 540 to the distal most tip 528a of the shaft 528, with the pusher assembly 530 retracted is between about 7 centimeters and about 20 centimeters. In other configurations, the total distance is between about 8 centimeters and about 12 centimeters.

Figure 18:
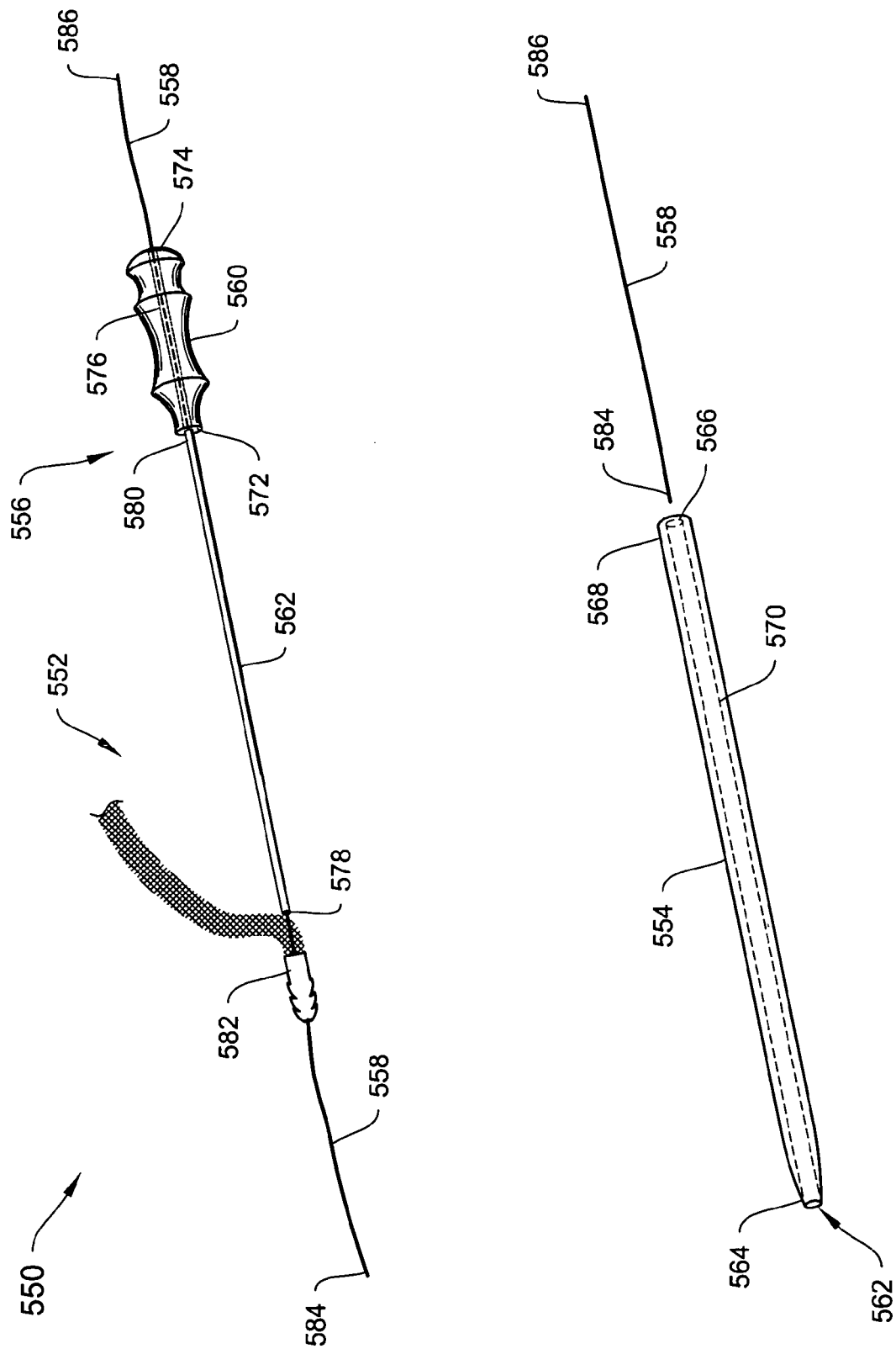
FIG. 18 shows a delivery system for implanting a sling assembly including a hollow soft tissue anchor/dilator to an anatomical site according to an illustrative embodiment of the invention.

FIG. 18 shows a delivery system 550 for implanting a sling assembly 552 at an anatomical location within the body of a patient according to another illustrative embodiment of the invention. The delivery system 550 includes a dilator 554, a pusher 556, and a guide member 558. The dilator 550 is a hollow tube having an aperture 562 at a distal end 564, an aperture 566 at a proximal end 568 and through-lumen 570 extending therebetween. The depicted dilator is substantially straight, yet this need not be the case. In alternative embodiments, it may include any combination of curved and/or straight sections, and may extend into one, two or more planes. As depicted, the dilator 554 has a conical distal end 564 for dilating tissue during tunneling and terminating in a tip that is sharp enough to pierce tissue. However, in other embodiments, the distal end may be dulled or have any other suitable configuration. The dilator 554 may be substantially rigid or flexible. Preferably, it is rigid enough to tunnel through tissue without bending or otherwise deflecting. The guide member 558 is sized and shaped to interfit with and axially pass through the dilator lumen 570. The guide member 558 may be substantially rigid or flexible enough to accommodate any curves or bends in the dilator 554.

The pusher 556 includes a handle 560 and a cannula 562. The handle 560 includes a distal end 572, a proximal end 574 and a through-lumen 576 extending axially there between. The cannula 562 extends axially from the distal end 572 of the handle 560, and includes a distal end 578, a proximal end 580, and a through-lumen extending therebetween. The through-lumen of the cannula 562 axially aligns with the through-lumen 576 of the handle 560.

In operation, the dilator 554 is inserted at the distal end 564 first through an incision, for example, in the vaginal wall of a patient until the distal tip 564 reaches a location at or near to the anatomical site at which the anchor 582 of the sling assembly 552 is to be implanted. The guide member 558, optionally a guide wire, is inserted axially into the proximal aperture 566 of the dilator 554 and advanced through the dilator lumen 570 and out the distal aperture 562. Optionally, the distal end 584 of the guide member 558 may be extended into the tissue of the patient past the anatomical site at which the anchor 582 is to be implanted. The dilator 554 is then slid proximally along the guide member 558 to remove it from the patient's body. The hollow anchor 582 of a sling assembly 552 is then slid distal end first over a proximal end 586 of the guide member 558, and slid distally along the guide member 558. The distal end 578 of the cannula 562 of the pusher 556 is then slid over the proximal end 586 of the guide member 558, and slid distally along the guide member 558 to abut the distal end 578 of the cannula 562 against a proximal end of the anchor 582. The pusher 556 is then slid farther distally along the guide member 558 to advance the tissue anchor 582 along the guide member 558 until it reaches the desired implantation location within the body of the patient. The pusher 556 and the guide member 558 may then be removed to leave the tissue anchor 582 and the corresponding end of the sling assembly 552 in place. The delivery system 550 is discussed further below with reference to FIGS. 23A-23C, 25A-25C, and 26A-26B.

FIGS. 19A-19B show a delivery system 600 for implanting a sling assembly 602 including a soft tissue anchor/dilator to an anatomical site in the body of a patient according to another illustrative embodiment of the invention. As shown, the delivery system 600 includes a hollow insertion shaft 606 and a push wire 608. The insertion shaft 606 may be configured similarly to the dilator 554 of FIG. 18 and includes a distal aperture 610, a proximal aperture 612 and a through-lumen extending there between. The push wire 608 has proximal 614 and distal 616 ends and may be of any suitable length.

The push wire 608 may be configured as a substantially rigid rod or may be flexible enough to accommodate any curves in the insertion shaft 606.

In operation and as shown in FIG. 19B, the tissue anchor 604 of the sling assembly 602 interfits over a distal end 618 of the insertion shaft 606. The distal end 618 of the shaft 606, with the anchor 604 so interfitted, is inserted into the body of the patient, for example via a vaginal wall incision, and advanced distally until the anchor 604 is positioned at the desired implantation site. The push wire 608 is then inserted at distal end 614 first into the proximal aperture 612 of the shaft 606 and advanced distally through the shaft 606 until the distal end 614 of the push wire 608 abuts the tissue anchor 604 and pushes it off the insertion shaft 606 to implant the anchor 604 and the associated sling assembly end at the desired anatomical location. The insertion shaft 606 and the push wire 608 may then removed from the patient.

Figure 20:
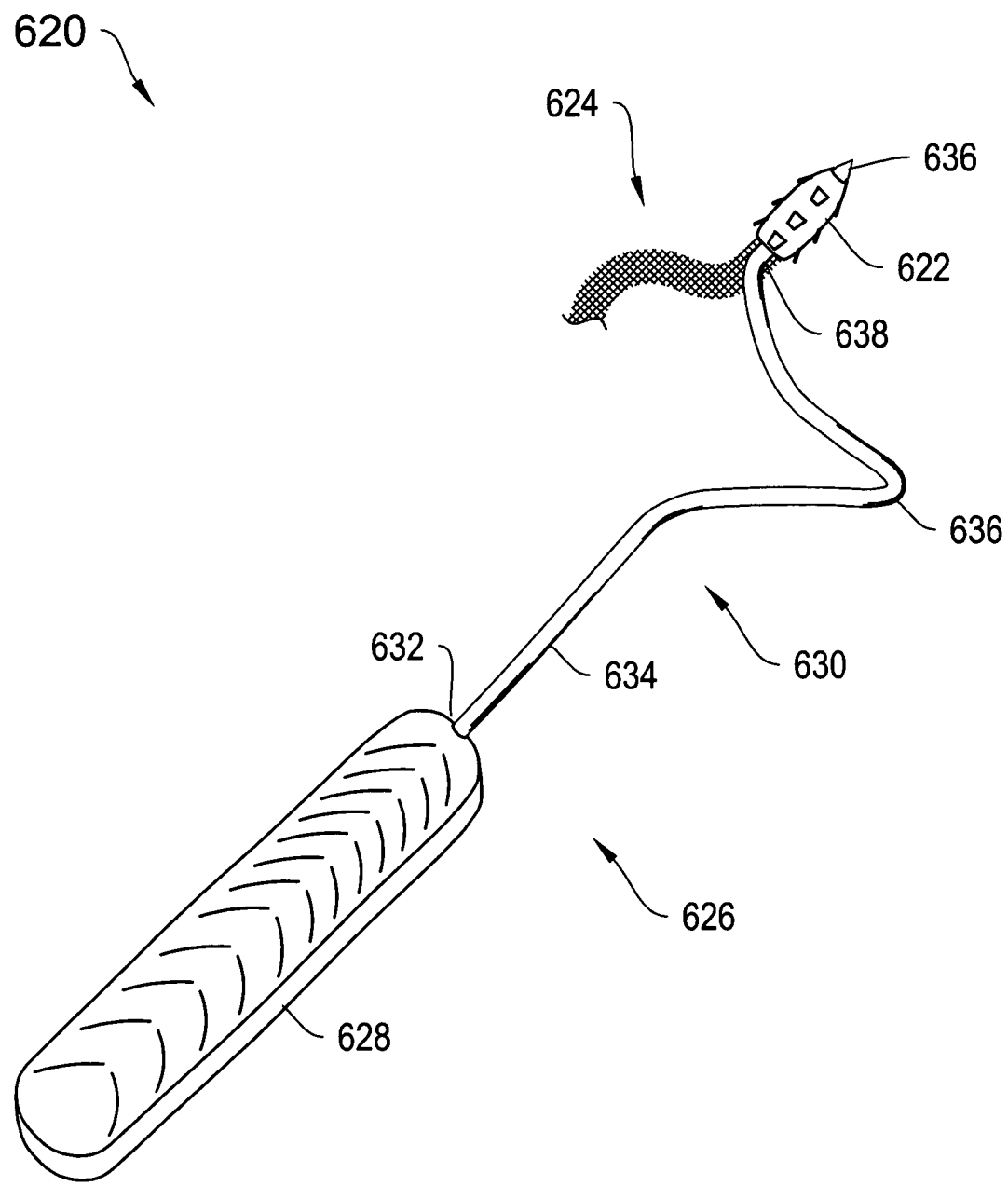
FIG. 20 shows a delivery system employing a delivery device having a spiral shaft according to an illustrative embodiment of the invention.

FIG. 20 shows a delivery system 620 for delivering a tissue anchor/dilator of a sling assembly 624 to an anatomical location in the body of a patient according to a further illustrative embodiment of the invention. The delivery system 620 includes a delivery device 626 having a handle 628 and a shaft 630 extending distally from a distal end 632 of the handle 628. According to this illustrative embodiment, the shaft 630 includes a first straight section 634 extending distally from the distal end 632 of the handle 628 and a spiral section 636 extending and spiraling away from the first straight section 634. The spiral section 636 extends into more than two planes and terminates distally in a second straight section, the tip 636 of which is shown extending from the hollow anchor 622. Although not shown, the illustrative shaft 630 forms a shoulder between the second straight section and the spiral section 636 near the proximal end 638 of the 622. This shoulder is similar to the shoulder 494 of the device 460 of FIGS. 15A and 15B. The system 620, with the shaft 630 inserted into the anchor 636 may be employed, for example, to deliver the anchor, and thus the associated sling assembly end, to or through a obturator membrane via an inside out (e.g., insert through an incision in the vaginal wall rather than an incision in the inner thigh) transobtural procedure.

Figure 21:
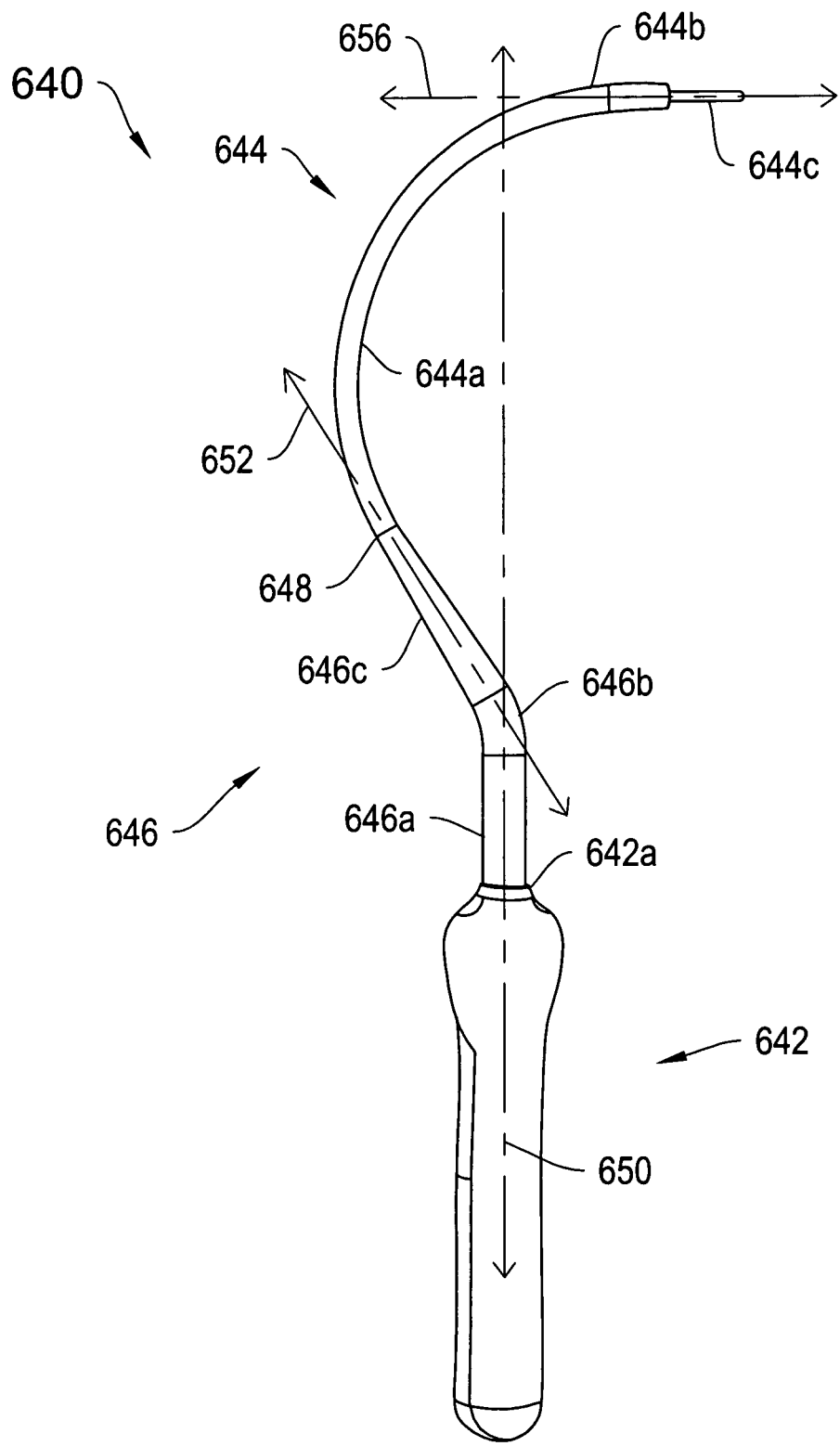
FIG. 21 shows a delivery device having a curved shaft for delivering a sling assembly, for example, transobturally according to an illustrative embodiment of the invention.

FIG. 21 shows another illustrative delivery 640 device particularly sized and shaped for transobtural placement of an implantable sling employing a soft tissue anchor/dilator, such as the anchors/dilators described above. The delivery device 640 includes a handle 642, a shaft 644, and a transitional portion 646 extending distally between a distal end 642a of the handle 642 and a proximal end 648 of the shaft 644. The transitional portion 646 includes a first straight section 646a, a curved section 646b, and a second straight section 646c, all lying substantially in a single plane, and may be formed as either part of the shaft 644 or as part of the handle 642. The shaft 644 includes a curved section 644a, a straight section 644b and a reduced diameter section 644c, all lying substantially in the same plane as the transitional portion 646. In the illustrative embodiment, the first straight section 646a of the transitional portion 646 attaches to the distal end 642a of the handle 642, extends distally along a first axis 650, and preferably has a substantially constant diameter. The curved section 646b of the transitional portion 646 extends from a distal end of the first straight section 646a, curves away from the first axis 650, and also preferably has a substantially constant diameter. The second straight section 646c extends from a distal end of the curved section 646b along a second axis 652, and preferably has a diameter that decreases from its proximal end to its distal end to provide increased structural stability to the shaft 644. The curved section 644a, preferably, has a substantially constant diameter, smaller than the diameter of the curved section 646b of the transitional portion 646, and extends from the distal end of the second straight section 646c of the transitional portion 646, curves back toward the first axis 650, and terminates at a distal end approximately at an intersection with the first axis 650. The straight section 644b, preferably, has a substantially constant diameter and extends from the distal end of the curved section 644a along a third axis 656, which crosses the first axis 650. According to the illustrative embodiment, the reduced diameter section 644c extends distally from the straight section 644b. In various illustrative embodiments, the dimensions for the shaft 644 may be the same or similar to those discussed with regard to the shaft 464 of FIGS. 15A and 15B. For example, the outside diameters of the second straight section 644b and the reduced diameter section 644c may be the same or similar to the dimensions given for the shaft section 480 and reduced diameter shaft section 488, respectively. Similarly, the length of the section 644c may also be the same or similar to the length ranges given for the shaft section 488.

FIGS. 22A-22C shows another illustrative delivery device 660 particularly sized and shaped for transobtural placement of an implantable sling, and employable, without limitation, with any of the illustrative embodiments described herein. More particularly, the delivery devices 660 includes a handle 662 with first 662a and second 662b substantially straight sections located substantially in a first plane and angled relative to each other, a transitional portion 665 extending out of a distal end 663 of the handle 662, and a shaft 664 extending from a distal end of the transitional portion 665. The shaft 664 includes curved section 664a, a straight section 664b, and terminates in a reduced diameter section 604c, comparable to the reduced diameter sections 488 and 644c of FIGS. 15B and 21, respectively.

The transitional portion 665 interfits and extends axially out of the distal end 663 of the second straight handle section 662b to affix the shaft 664 to the handle 662. As a result, the transitional portion 665 is substantially co-planer with the handle 662 in the first plane. The curved section 664a of the shaft 664 extends from a distal end of the transitional portion 665. The straight section 664b of the shaft 664 extend from a distal end of the curved section 664a. The curved section 664a and the straight section 664b are substantially coplanar in a second plane. According to the illustrative embodiment of FIGS. 22A-22C, the first and second planes are substantially orthogonal to each other. However, the first and second planes may be at any suitable angle (e.g., about 10, 20, 30, 45, 60, 70 or 80 degrees) to each other.

To provide structural reinforcement, the sections 662a and 662b have a cross sectional diameter that tapers to be smaller at the distal end 603 of the handle 602. Additionally, rather than having a tapered transitional portion 665, the transitional portion 655 is formed as part of the shaft 604, as shown in FIG. 22A, the tapered portions 662b and 662b of the embodiment of FIGS. 22A-22C are formed as part of the handle 662. According to one feature, this configuration reduces the length of the transitional portion 665 and thus, provides improved structural support for the curved section 664a. Preferably, in operation, neither the handle 662 nor the intermediate/transitional portion 665 extends into the body of the patient, and provides a positive stop against this occurring.

Figure 23A:
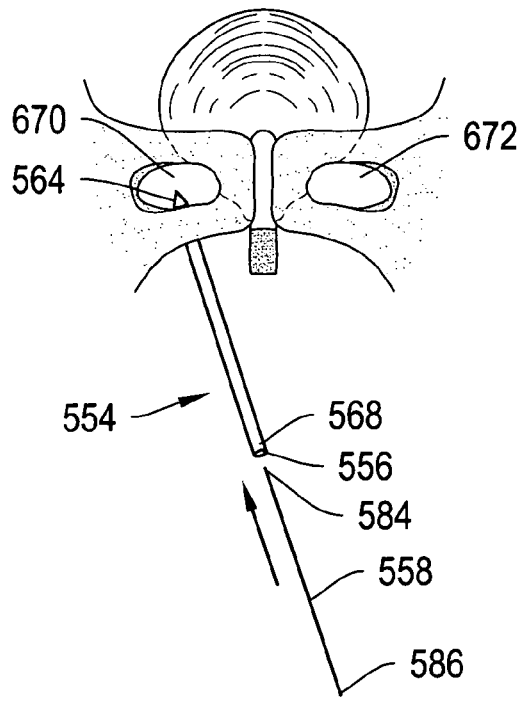
FIGS. 23A-23C depict an approach for delivering a sling assembly transobturally using the delivery system of FIG. 18 according to an illustrative embodiment of the invention.
Figure 23B:
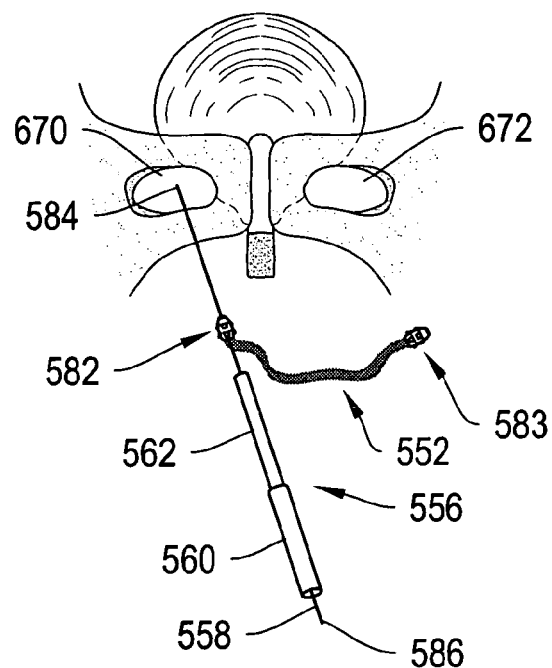
Figure 23C:
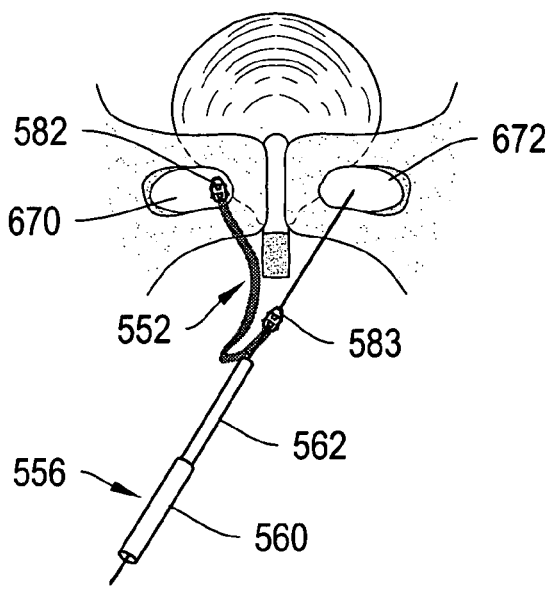

FIGS. 23A-23C illustrate an approach for delivering a sling assembly transobturally using the delivery system 550 of FIG. 18 according to an illustrative embodiment of the invention. Referring also to FIG. 18, as shown in FIG. 23A, the dilator 554 is inserted distal end 564 first through an incision, for example, in the vaginal wall of a patient until the distal tip 564 reaches an obturator foramen 670. With reference to FIGS. 23A and 23B, the guide member 558 is then inserted axially into the proximal aperture 566 of the dilator 554 and advanced through the dilator lumen 570 and out the distal aperture 562 into the obturator foramen 670. The dilator 554 is then slid proximally along the guide member 558 to remove it from the patient's body. As shown in FIG. 23B, the hollow anchor 582 of the sling assembly 552 is then slid, distal end first, over a proximal end 586 of the guide member 558, and slid distally along the guide member 558. The distal end 578 of the cannula 562 of the pusher 556 is then slid over the proximal end 586 of the guide member 558, and slid distally along the guide member 558 to abut the distal end 578 of the cannula 562 against a proximal end of the anchor 582. The pusher 556 is then further slid distally along the guide member 558 to advance the tissue anchor 582 along the guide member 558 until it enters the obturator foramen 670. As shown in FIG. 23C, the pusher 556 and the guide member 558 are then removed to leave the tissue anchor 582 and the corresponding end of the sling assembly 552 in place in the obturator foramen 670. As shown in FIG. 23C, the procedure is repeated on the other side of the body to implant the second anchor 583 and its associated sling assembly end in the obturator foramen 672.

According to the illustrative embodiment of FIGS. 23A-23C, the anchors 582 and 583 are delivered through respective obturator membranes to about 2.5 cm into the obturator foramen. However, in other illustrative embodiments, the anchors 582 and 583 are delivered through the respective obturator membranes about 1 centimeter to about 2.5 centimeters into the obturator formen. The anchors 582 and 583 may also be fixed to the obturator membrane.

Figure 24A:
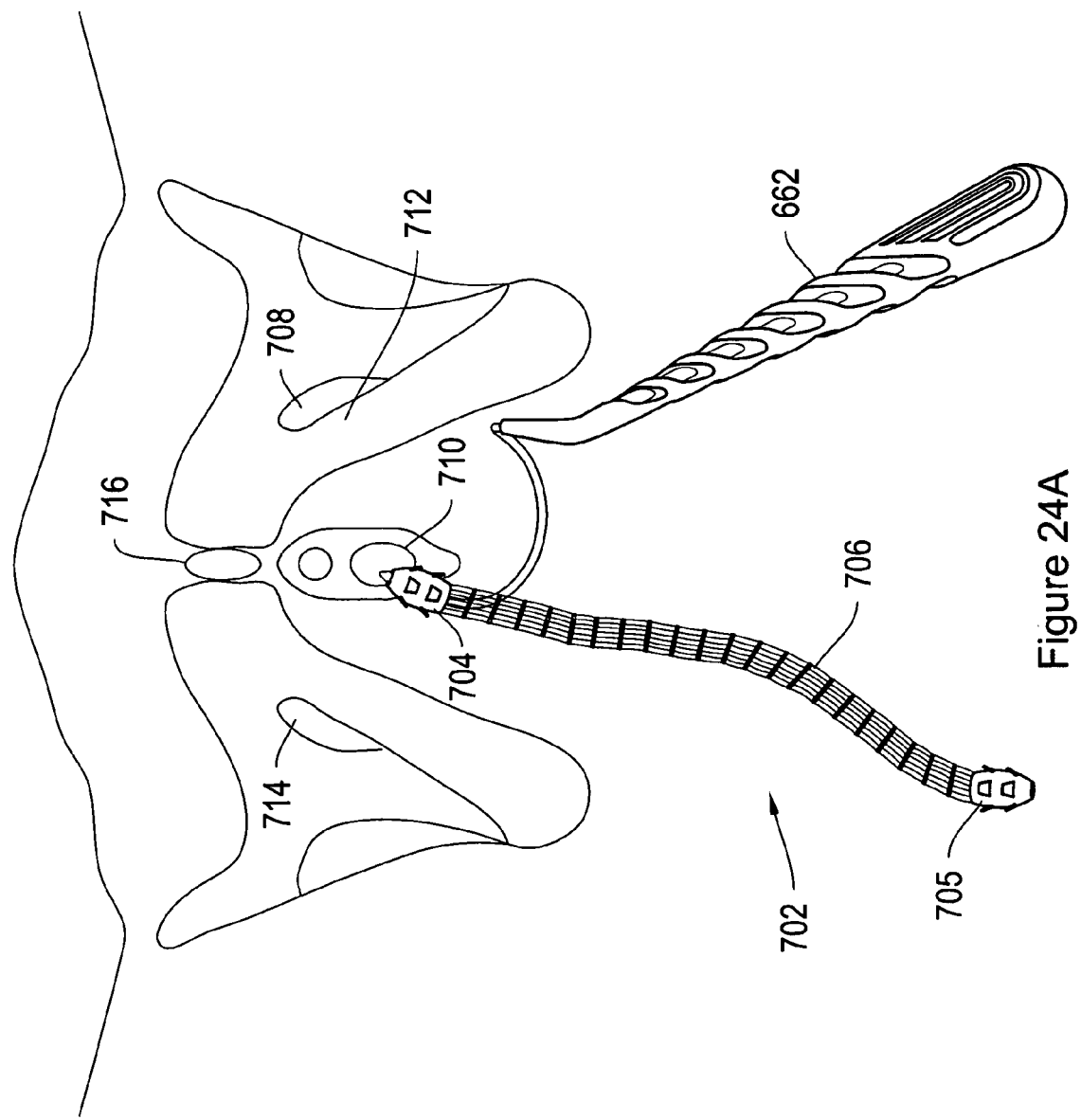
FIGS. 24A-24C depict an approach for delivering a sling assembly transobturally using the delivery system of FIGS. 22A-22C according to an illustrative embodiment of the invention.
Figure 24B:
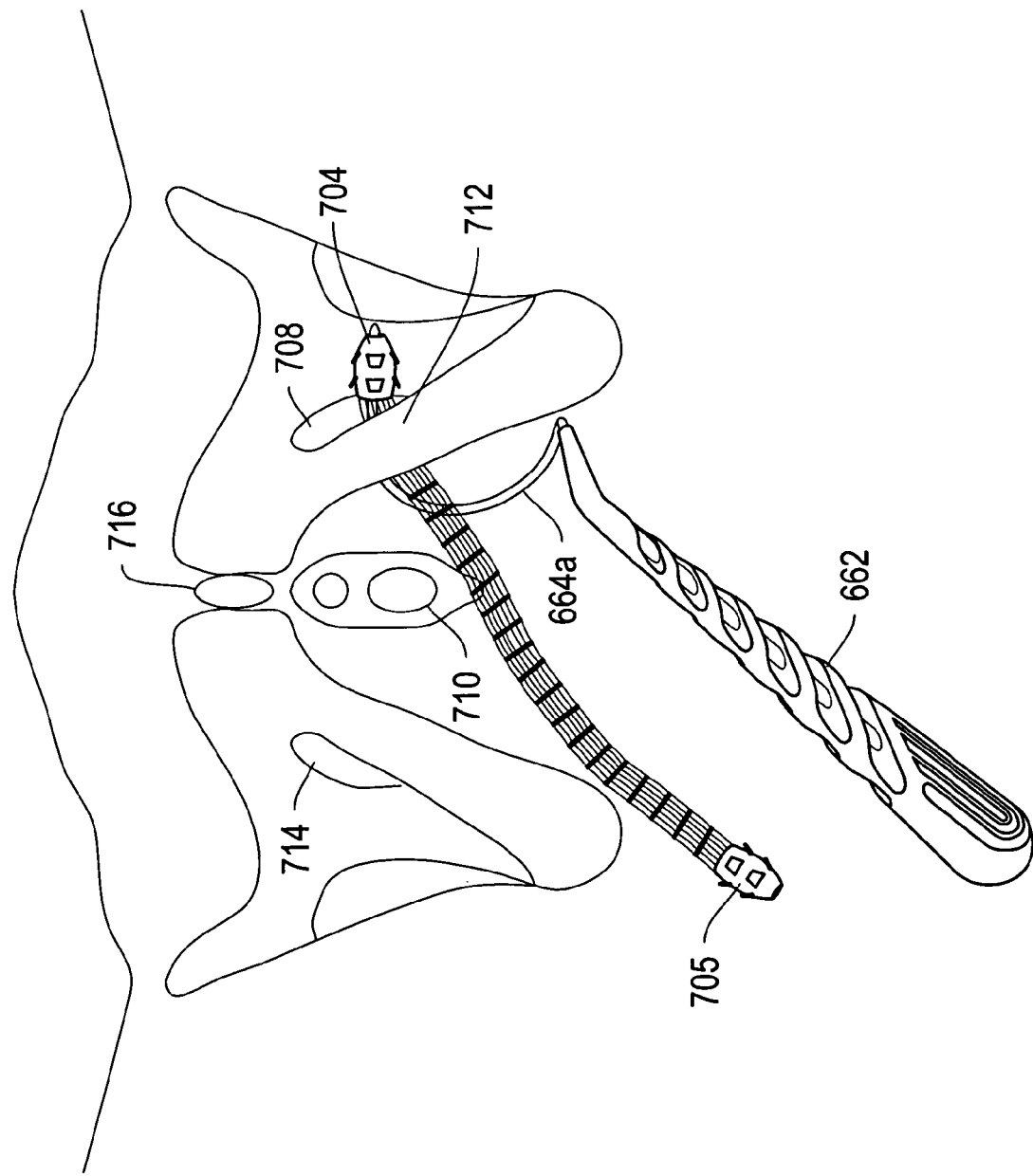
Figure 24C:
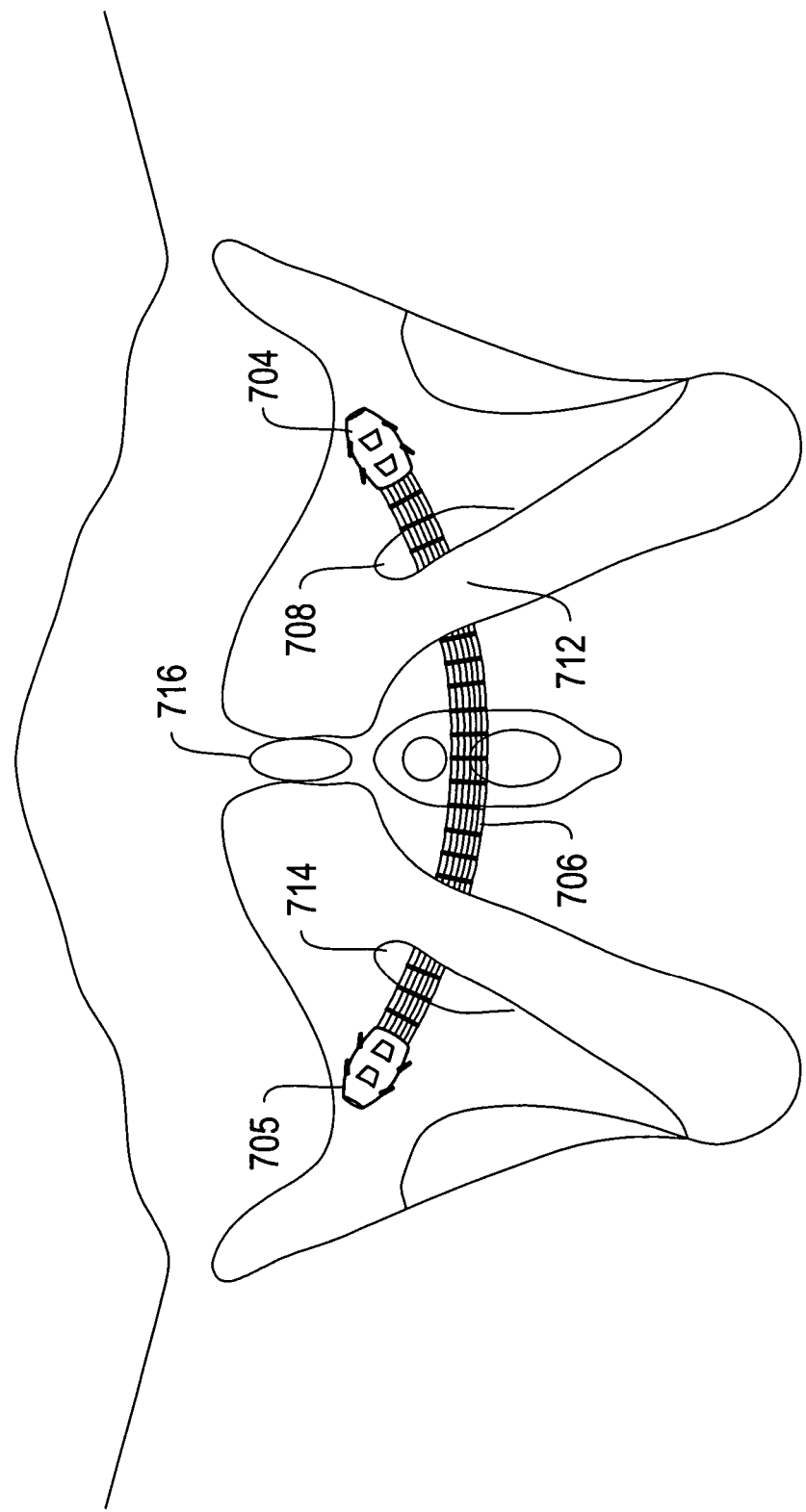

FIGS. 24A-24C depict an approach for delivering a sling assembly 702 transobturally using the delivery system of FIGS. 22A-22C according to an illustrative embodiment of the invention. The delivery device 664 is employed to describe this embodiment. However, the delivery device 640 may be employed in a similar fashion. Additionally, as in the previously described embodiment, the barbed tissue anchor, may be replaced with a relative smooth tissue anchor and/or with a anchor-sized tissue dilator. To begin, an incision is made in the anterior vaginal wall and dissected bilaterally to the interior portion of the inferior pubic ramus. The soft tissue anchor 704 attached to an end of the sling 706 is interfitted over the reduced diameter portion 664c of the delivery device shaft 664. Referring to FIGS. 24A and 24B, a medical operator grasps the handle 662 and inserts the delivery device shaft portion 664c with the anchor 102 installed through the vaginal incision. With a lateral motion, the medical operator passes the curved portion 664a of the shaft 664 behind the ischiopubic ramus 712 and pierces the obturator membrane 708. The delivery device shaft 664 can then be withdrawn from the body leaving the anchor 704 implanted in or through the obturator membrane 708 and, optionally, fixed to the obturator membrane 708. As indicated in FIG. 24C, this process is repeated with the same or a second delivery device having an opposite curvature and the second soft tissue anchor 705 to implant the second soft tissue anchor 705 in or through the obturator membrane 714 on the contralateral side of the body. As shown in FIG. 24C the sling 706 forms a supportive platform under the urethra 716.

Figure 25A:
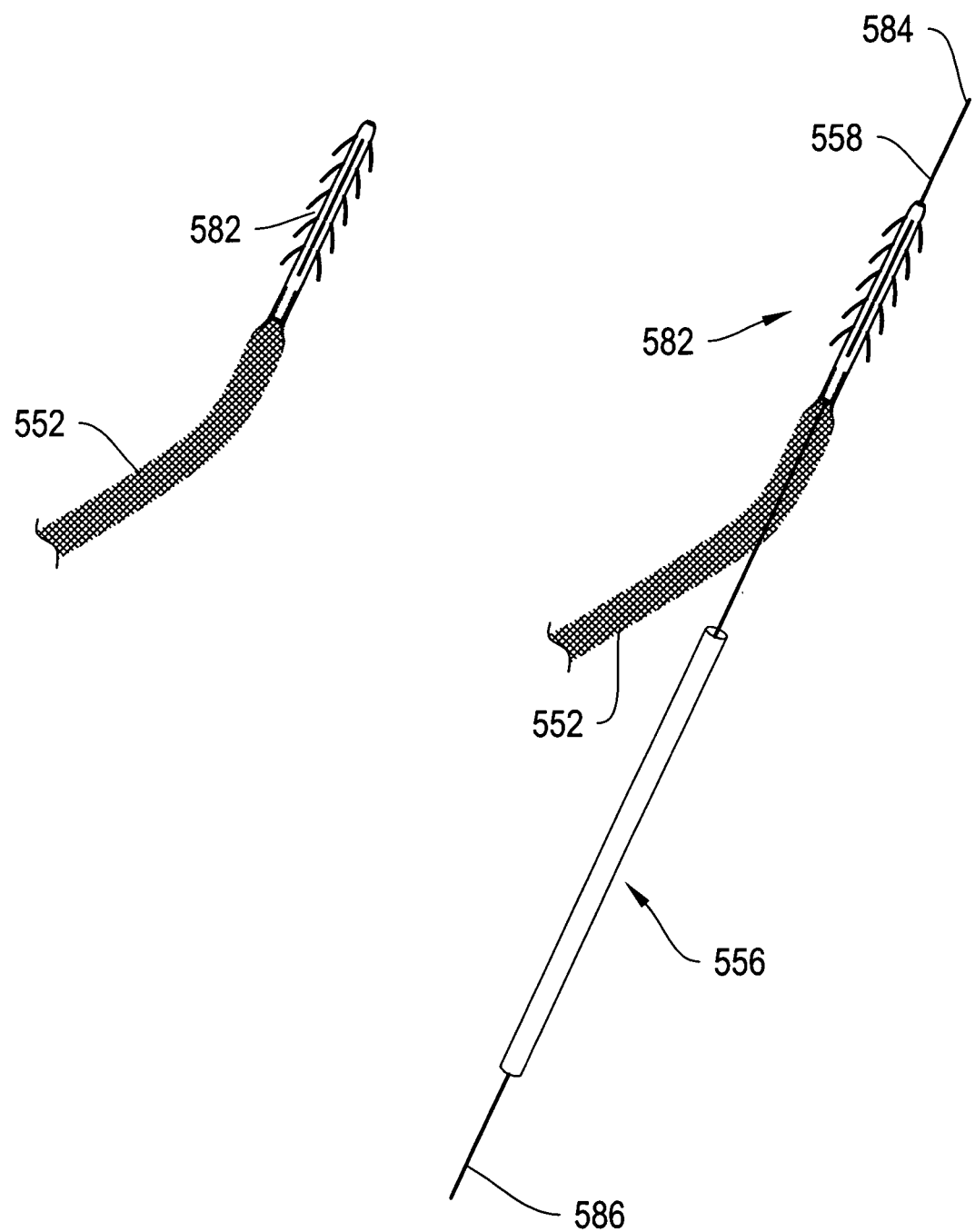
FIGS. 25A-25C show a detailed view of placing a soft tissue anchor/dilator of a sling assembly according to an illustrative embodiment of the invention.
Figure 25B:
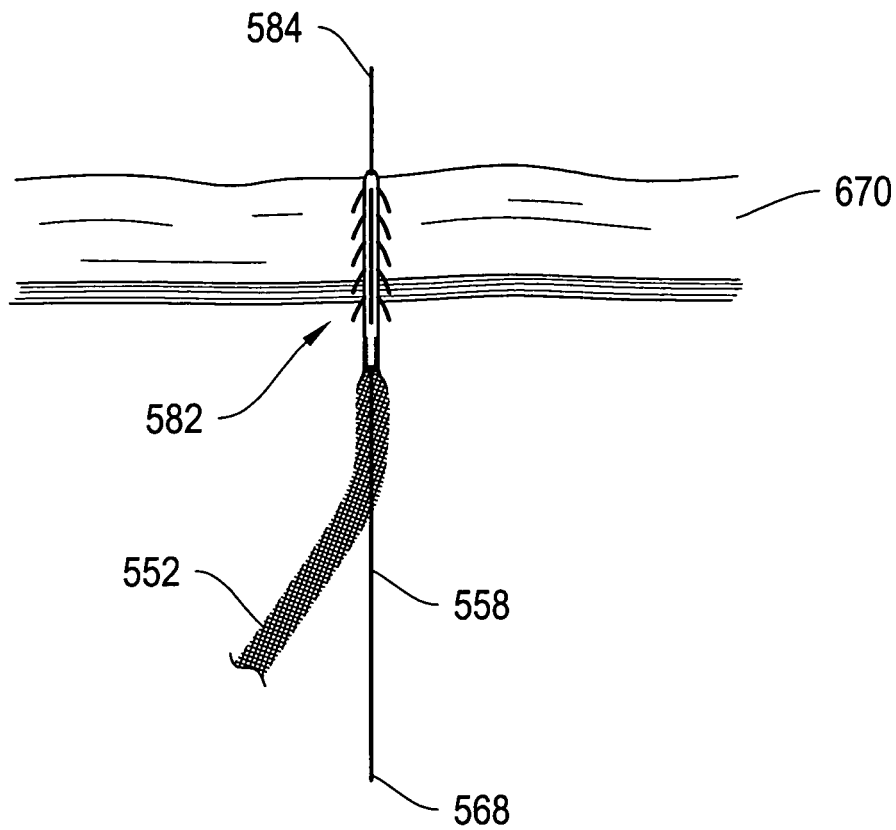
Figure 25C:
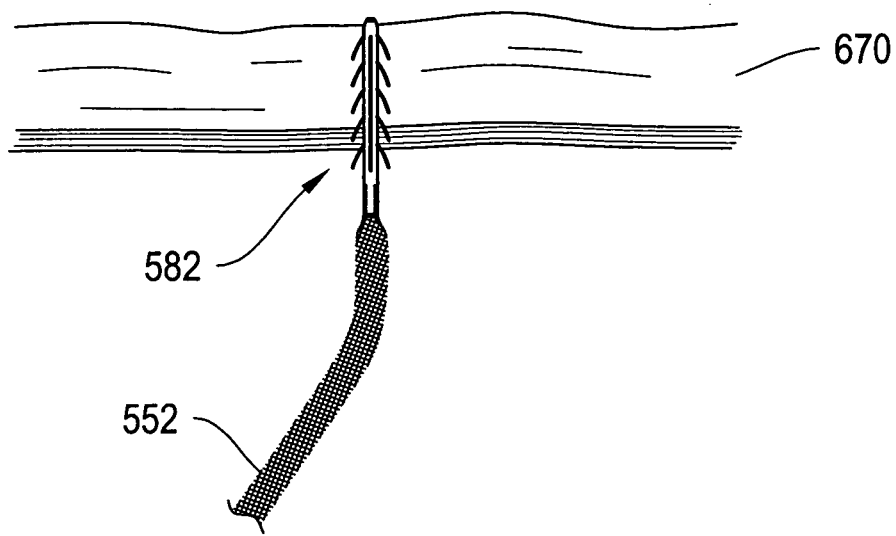

FIGS. 25A-25C show a more detailed view of how an anchor/dilator may be placed in the obturator membrane 670 using the procedure of FIGS. 23A-23C according to an illustrative embodiment of the invention. As shown in FIGS. 23A-23C, the anchor 582 is placed over the guide member 558, which has been previously inserted through the obturator membrane 670. Then, the pusher 556 is advanced behind it to advance the anchor 582 distally along the guide member 558.

As seen in the illustrative embodiment of FIG. 23C, the anchor 552 may be advanced into the obturator membrane 670. The radial projections on the anchor 582 inhibit the anchor 582 from being retracted out of the membrane 670 once inserted. Regardless of the procedure employed, the anchor 582 may be advanced into the membrane until the desired sling tension is achieved under the urethra. Alternatively, any of the above described approaches may be employed to adjust sling tension.

Figure 26A:
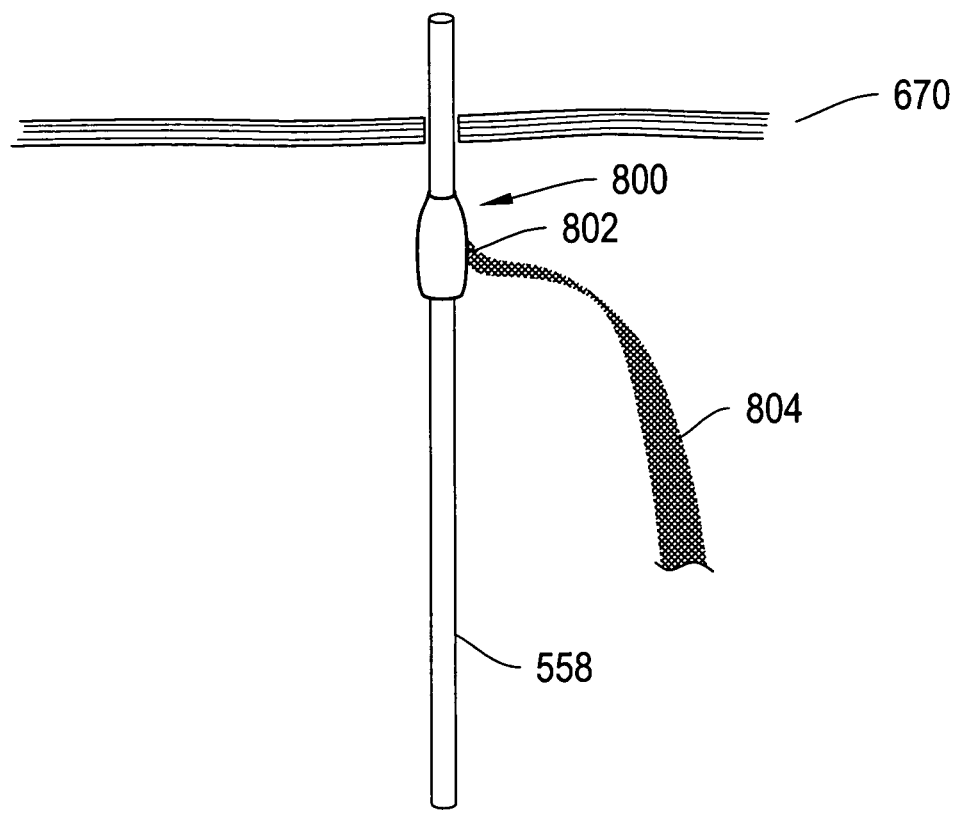
FIGS. 26A-26B show a detailed view of an alternative placement of a soft tissue anchor/dilator of a sling assembly according to another illustrative embodiment of the invention.
Figure 26B:
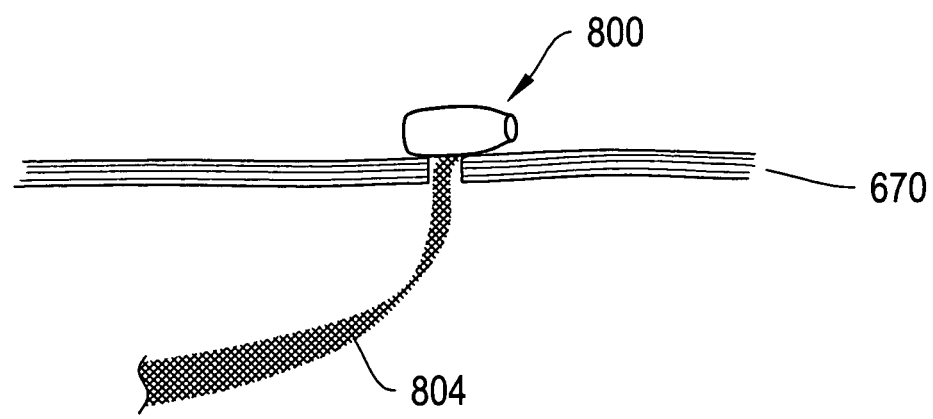

FIGS. 26A-26B show a detailed view of an alternative placement of a soft tissue anchor/dilator of a sling assembly according to another illustrative embodiment of the invention. In this embodiment, an anchor/dilator 800 includes aperture 802 in its side wall about midway along its length, for example, similar to the buckle arrangement of FIGS. 13A and 13B. As shown in FIG. 26B, subsequent to being advanced along the guide member 558 through the obturator membrane 670 and the guide member 558 being removed, tension applied to the sling 804 causes the anchor 800 to pivot horizontally until braced against the obturator membrane 670. The lengthwise orientation of the anchor 800 further prevents withdrawal of the anchor 800 and ensures that the sling 804 will be held securely in place. As mentioned above, in some implementations, the anchor/dilator 800 may dissolve to leave only the sling end embedded in the obturator membrane to hold the sling in place.

Variations, modifications, and other implementations of what is described may occur without departing from the spirit and the scope of the invention. By way of example, and without limitation, examples of slings, sling assemblies, sling delivery devices and approaches, sling assembly-to-delivery device association mechanisms, and sling anchoring mechanisms including features that may be employed with the above described invention are disclosed in U.S. Pat. No. 6,042,534, entitled "Stabilization sling for use in minimally invasive pelvic surgery," U.S. Pat. No. 6,755,781, entitled "Medical slings," U.S. Pat. No. 6,666,817, entitled "Expandable surgical implants and methods of using them," U.S. Pat. No. 6,042,592, entitled "Thin soft tissue surgical support mesh," U.S. Pat. No. 6,375,662, entitled "Thin soft tissue surgical support mesh," U.S. Pat. No. 6,669,706, entitled "Thin soft tissue surgical support mesh," U.S. Pat. No. 6,752,814, entitled "Devices for minimally invasive pelvic surgery," U.S. Ser. No. 10/918,123, entitled "Surgical Slings," U.S. patent application Ser. No. 10/641,376, entitled "Spacer for sling delivery system," U.S. patent application Ser. No. 10/641,192, entitled "Medical slings," U.S. Ser. No. 10/641,170, entitled "Medical slings," U.S. Ser. No. 10/640,838, entitled "Medical implant," U.S. patent application Ser. No. 10/460,112, entitled "Medical slings," U.S. patent application Ser. No. 10/631,364, entitled "Bioabsorbable casing for surgical sling assembly," U.S. Ser. No. 10/092,872, entitled "Medical slings," U.S. patent application Ser. No. 10/939,191, entitled "Devices for minimally invasive pelvic surgery," U.S. patent application Ser. No. 10/774,842, entitled "Devices for minimally invasive pelvic surgery," U.S. patent application Ser. No. 10/774,826, entitled "Devices for minimally invasive pelvic surgery," U.S. Ser. No. 10/015,114, entitled "Devices for minimally invasive pelvic surgery," U.S. patent application Ser. No. 10/973,010, entitled "Systems and methods for sling delivery and placement," U.S. patent application Ser. No. 10/957,926, entitled "Systems and methods for delivering a medical implant to an anatomical location in a patient," U.S. patent application Ser. No. 10/939,191, entitled "Devices for minimally invasive pelvic surgery," U.S. patent application Ser. No. 10/918,123, entitled "Surgical slings," U.S. patent application Ser. No. 10/832,653, entitled "Systems and methods for sling delivery and placement," U.S. patent application Ser. No. 10/642,397, entitled "Systems, methods and devices relating to delivery of medical implants," U.S. patent application Ser. No. 10/642,395, entitled "Systems, methods and devices relating to delivery of medical implants," U.S. patent application Ser. No. 10/642,365, entitled "Systems, methods and devices relating to delivery of medical implants," U.S. patent application Ser. No. 10/641,487, entitled "Systems, methods and devices relating to delivery of medical implants," U.S. patent application Ser. No. 10/094,352, entitled "System for implanting an implant and method thereof," U.S. patent application Ser. No. 10/093,498, entitled "System for implanting an implant and method thereof," U.S. patent application Ser. No. 10/093,450, entitled "System for implanting an implant and method thereof," U.S. patent application Ser. No. 10/093,424, entitled "System for implanting an implant and method thereof," U.S. patent application Ser. No. 10/093,398, entitled "System for implanting an implant and method thereof," and U.S. patent application Ser. No. 10/093,371, entitled "System for implanting an implant and method thereof," the entire contents of all of which are incorporated herein by reference.

What is claimed is:

1. A system for the treatment of urinary incontinence, comprising:
   a sling having first and second ends;
   first and second anchors, wherein the first end of the sling interfits within a slot in the first anchor, and the second end of the sling interfits within a slot in the second anchor,
      each of said first and second anchors comprising a body having a proximal end, a distal end, and a through lumen extending therebetween, each of said first and second anchors further comprising at least one barb projecting radially therefrom; and
   a delivery device for delivering said sling within the body of a patient, said delivery device comprising a shaft comprising a distal section that has an outer diameter that is less than a diameter of said shaft at a location immediately proximal to the distal section, wherein the distal section of said shaft is configured to extend through the through lumen of each of said first and second anchors.

2. The system of claim 1, wherein said first and second anchors are soft tissue anchors.

3. The system of claim 1, wherein said first and second anchors consist of a polymer material.

4. The system of claim 1, wherein said at least one barb has a pointed tip.

5. The system of claim 1, wherein said sling comprises tanged edges.

6. The system of claim 5, wherein said shaft is formed substantially in a single plane.

7. The system of claim 1, wherein said shaft comprises a straight section and a curved section distal to said straight section.

8. The system of claim 7, wherein said straight section of said shaft has an outside diameter that is substantially constant.

9. The system of claim 1, further comprising a shoulder at the intersection between said distal section and said location immediately proximal to said distal section.

10. The system of claim 9, wherein each of said first and second anchors are configured to abut said shoulder during delivery thereof into the patient.

11. The system of claim 1, wherein said sling comprises polypropylene.

12. The system of claim 1, wherein said sling has a mesh configuration.

13. The system of claim 1, wherein said delivery device further comprises a handle proximal to said shaft.

14. The system of claim 1, wherein said delivery device is configured to deliver each of said first and second anchors within the patient.

15. A system for the treatment of urinary incontinence, comprising:
   a mesh sling comprising polypropylene and having first and second ends;
   first and second soft tissue anchors, wherein the first end of the sling interfits within a slot in the first anchor and the second end of the sling interfits within a slot in the second anchor,
      each of said first and second soft tissue anchors consisting of a polymer material and comprising a body having a proximal end, a distal end, and a through lumen extending therebetween, each of said first and second soft tissue anchors further comprising at least one barb projecting radially therefrom, each of said barbs having a pointed tip; and
   a delivery device for delivering said sling within the body of a patient, said delivery device comprising a shaft comprising a distal section that has an outer diameter that is less than a diameter of said shaft at a location immediately proximal to the distal section, wherein the distal section of said shaft is configured to extend through the through lumen of each of said first and second soft tissue anchors, said shaft being formed substantially in a single plane and comprising a straight section and a curved section distal to said straight section.

* * * * *